US010463418B2

(12) United States Patent
Suslov

(10) Patent No.: US 10,463,418 B2
(45) Date of Patent: Nov. 5, 2019

(54) VOLUMETRICALLY OSCILLATING PLASMA FLOWS

(71) Applicant: Plasma Surgical Investments Limited, Tortula (VG)

(72) Inventor: Nikolay Suslov, Atlanta, GA (US)

(73) Assignee: Plasma Surgical Investments Limited, Tortola (VG)

(*) Notice: Subject to any disclaimer, the term of this patent is extended or adjusted under 35 U.S.C. 154(b) by 876 days.

(21) Appl. No.: 14/809,865

(22) Filed: Jul. 27, 2015

(65) Prior Publication Data

US 2015/0327906 A1    Nov. 19, 2015

Related U.S. Application Data

(62) Division of application No. 12/841,361, filed on Jul. 22, 2010, now Pat. No. 9,089,319.

(51) Int. Cl.
*A61B 18/04*     (2006.01)
*A61B 18/12*     (2006.01)
(Continued)

(52) U.S. Cl.
CPC ........ *A61B 18/042* (2013.01); *A61B 18/1206* (2013.01); *A61B 2017/00181* (2013.01);
(Continued)

(58) Field of Classification Search
CPC ........... A61B 2018/00011; A61B 2018/00589; A61B 2018/00601; A61B 2018/00607; A61B 2018/00625; A61B 2018/00702; A61B 2018/122; A61B 18/042; A61B 18/1206
See application file for complete search history.

(56) References Cited

U.S. PATENT DOCUMENTS 3,077,108 A    2/1963   Gage et al.
3,082,314 A    3/1963   Yoshiaki et al.
(Continued)

FOREIGN PATENT DOCUMENTS

AU    2000250426    6/2005
AU    2006252145    1/2007
(Continued)

OTHER PUBLICATIONS

U.S. Appl. No. 12/696,411, filed Jan. 29, 2010, Suslov.
(Continued)

*Primary Examiner* — Michael F Peffley
*Assistant Examiner* — Samantha M Good

(57) ABSTRACT

Volumetrically oscillating plasma flows, the volume of which controllably expands and contracts with time, are disclosed. Volumetrically oscillating plasma flows are generated by providing an energy with a power density that changes with time to the plasma-generating gas to form a plasma flow. The changes in the energy power density result in plasma flow volumetric oscillations. Volumetric oscillations with a frequency of above 20,000 Hz results in ultrasonic acoustic waves, which are known to be beneficial for various medical applications. System for providing volumetrically oscillating plasma flows and a variety of surgical non-surgical applications of such flows are also disclosed.

20 Claims, 53 Drawing Sheets

(51) Int. Cl.
    *A61B 18/00*         (2006.01)
    *A61B 17/00*         (2006.01)
    *A61N 7/02*          (2006.01)
    *A61N 7/00*          (2006.01)
    *H05H 1/48*         (2006.01)

(52) U.S. Cl.
    CPC ............ *A61B 2018/00011* (2013.01); *A61B 2018/0091* (2013.01); *A61B 2018/00589* (2013.01); *A61B 2018/00601* (2013.01); *A61B 2018/00607* (2013.01); *A61B 2018/00625* (2013.01); *A61B 2018/00702* (2013.01); *A61B 2018/00994* (2013.01); *A61N 7/02* (2013.01); *A61N 2007/0039* (2013.01); *H05H 1/48* (2013.01)

(56) References Cited

U.S. PATENT DOCUMENTS

| | | |
|---|---|---|
| 3,145,287 A | 8/1964 | Seibein et al. |
| 3,153,133 A | 10/1964 | Ducati |
| 3,360,988 A | 1/1968 | Stein et al. |
| 3,413,509 A | 11/1968 | Cann et al. |
| 3,433,991 A | 3/1969 | Whyman |
| 3,434,476 A | 3/1969 | Shaw et al. |
| 3,534,388 A | 10/1970 | Takakiyo et al. |
| 3,628,079 A | 12/1971 | Dobbs et al. |
| 3,676,638 A | 7/1972 | Stand |
| 3,775,825 A | 12/1973 | Wood et al. |
| 3,803,380 A | 4/1974 | Ragaller |
| 3,838,242 A | 9/1974 | Goucher |
| 3,851,140 A | 11/1974 | Goucher |
| 3,866,089 A | 2/1975 | Hengartner |
| 3,903,891 A | 9/1975 | Brayshaw |
| 3,914,573 A | 10/1975 | Muehlberger |
| 3,938,525 A | 2/1976 | Goucher |
| 3,991,764 A | 11/1976 | Incropera et al. |
| 3,995,138 A | 11/1976 | Kalev et al. |
| 4,029,930 A | 6/1977 | Sagara et al. |
| 4,035,684 A | 7/1977 | Svoboda et al. |
| 4,041,952 A | 8/1977 | Morrison, Jr. et al. |
| 4,201,314 A | 5/1980 | Samuel et al. |
| 4,256,779 A | 3/1981 | Sokol et al. |
| 4,317,984 A | 3/1982 | Fridlyand |
| 4,397,312 A | 8/1983 | Molko |
| 4,445,021 A | 4/1984 | Irons et al. |
| 4,620,080 A | 10/1986 | Arata et al. |
| 4,661,682 A | 4/1987 | Gruner et al. |
| 4,672,163 A | 6/1987 | Matsui et al. |
| 4,674,683 A | 6/1987 | Fabel |
| 4,682,598 A | 7/1987 | Beraha |
| 4,696,855 A | 9/1987 | Pettit et al. |
| 4,711,627 A | 12/1987 | Oeschsle et al. |
| 4,713,170 A | 12/1987 | Saibic |
| 4,743,734 A | 5/1988 | Garlanov et al. |
| 4,764,656 A | 8/1988 | Browning |
| 4,777,949 A | 10/1988 | Perlin |
| 4,780,591 A | 10/1988 | Bernecki et al. |
| 4,781,175 A | 11/1988 | McGreevy et al. |
| 4,784,321 A | 11/1988 | Delaplace |
| 4,785,220 A | 11/1988 | Brown et al. |
| 4,839,492 A | 6/1989 | Bouchier et al. |
| 4,841,114 A | 6/1989 | Browning |
| 4,853,515 A | 8/1989 | Willen et al. |
| 4,855,563 A | 8/1989 | Beresnev et al. |
| 4,866,240 A | 9/1989 | Webber |
| 4,869,936 A | 9/1989 | Moskowitz et al. |
| 4,874,988 A | 10/1989 | English |
| 4,877,937 A | 10/1989 | Muller |
| 4,916,273 A | 4/1990 | Browning |
| 4,924,059 A | 5/1990 | Rotolico et al. |
| 5,008,511 A | 4/1991 | Ross |
| 5,013,883 A | 5/1991 | Fuimefreddo et al. |
| 5,100,402 A | 3/1992 | Fan |
| 5,144,110 A | 9/1992 | Marantz et al. |
| 5,151,102 A | 9/1992 | Kamiyama et al. |
| 5,201,900 A | 4/1993 | Nardella |
| 5,207,691 A | 5/1993 | Nardella |
| 5,211,646 A | 5/1993 | Alperovich et al. |
| 5,217,460 A | 6/1993 | Knoepfler |
| 5,225,652 A | 6/1993 | Landes |
| 5,227,603 A | 7/1993 | Doolette et al. |
| 5,261,905 A | 11/1993 | Doressey |
| 5,285,967 A | 2/1994 | Weidman |
| 5,332,885 A | 7/1994 | Landes |
| 5,352,219 A | 10/1994 | Reddy |
| 5,396,882 A | 3/1995 | Zapol |
| 5,403,312 A | 4/1995 | Yates et al. |
| 5,406,046 A | 4/1995 | Landes |
| 5,408,066 A | 4/1995 | Trapani et al. |
| 5,412,173 A | 5/1995 | Muehlberger |
| 5,445,638 A | 8/1995 | Rydell et al. |
| 5,452,854 A | 9/1995 | Keller |
| 5,460,629 A | 10/1995 | Shlain et al. |
| 5,485,721 A | 1/1996 | Steenborg |
| 5,514,848 A | 5/1996 | Ross et al. |
| 5,519,183 A | 5/1996 | Mueller |
| 5,527,313 A | 6/1996 | Scott et al. |
| 5,573,682 A | 11/1996 | Beason et al. |
| 5,582,611 A | 12/1996 | Tsuruta et al. |
| 5,620,616 A | 4/1997 | Anderson et al. |
| 5,629,585 A | 5/1997 | Altmann |
| 5,637,242 A | 6/1997 | Muehlberger |
| 5,640,843 A | 6/1997 | Aston |
| 5,662,680 A | 9/1997 | Desai |
| 5,665,085 A | 9/1997 | Nardella |
| 5,679,167 A | 10/1997 | Muehlberger |
| 5,680,014 A | 10/1997 | Miyamoto et al. |
| 5,688,270 A | 11/1997 | Yates et al. |
| 5,697,281 A | 12/1997 | Eggers et al. |
| 5,697,882 A | 12/1997 | Eggers et al. |
| 5,702,390 A | 12/1997 | Austin et al. |
| 5,720,745 A | 2/1998 | Farin et al. |
| 5,733,662 A | 3/1998 | Bogachek |
| 5,797,941 A | 8/1998 | Schulze et al. |
| 5,827,271 A | 10/1998 | Buysse et al. |
| 5,833,690 A | 11/1998 | Yates et al. |
| 5,837,959 A | 11/1998 | Muehlberger et al. |
| 5,843,079 A | 12/1998 | Suslov |
| 5,858,469 A | 1/1999 | Sahoo et al. |
| 5,858,470 A | 1/1999 | Bernecki et al. |
| 5,897,059 A | 4/1999 | Muller |
| 5,906,757 A | 5/1999 | Kong et al. |
| 5,932,293 A | 8/1999 | Belashchenko et al. |
| 6,003,788 A | 12/1999 | Sedov |
| 6,042,019 A | 3/2000 | Rusch |
| 6,099,523 A | 8/2000 | Kim et al. |
| 6,135,998 A | 10/2000 | Palanker |
| 6,137,078 A | 10/2000 | Keller |
| 6,137,231 A | 10/2000 | Anders et al. |
| 6,114,649 A | 11/2000 | Delcea |
| 6,162,220 A | 12/2000 | Nezhat |
| 6,169,370 B1 | 1/2001 | Platzer |
| 6,181,053 B1 | 1/2001 | Roberts |
| 6,202,939 B1 | 3/2001 | Delcea |
| 6,206,878 B1 | 3/2001 | Bishop |
| 6,273,789 B1 | 8/2001 | Lasalle et al. |
| 6,283,386 B1 | 9/2001 | Van Steenkiste et al. |
| 6,329,628 B1 | 12/2001 | Kuo |
| 6,352,533 B1 | 3/2002 | Ellman et al. |
| 6,386,140 B1 | 5/2002 | Muller et al. |
| 6,392,189 B1 | 5/2002 | Delcea |
| 6,443,948 B1 | 9/2002 | Suslov et al. |
| 6,475,212 B2 | 11/2002 | Tanrisever |
| 6,475,215 B1 * | 11/2002 | Tanrisever ............ A61B 18/042 606/32 |
| 6,514,252 B2 | 2/2003 | Nezhat et al. |
| 6,515,252 B1 | 2/2003 | Girold |
| 6,528,947 B1 | 3/2003 | Chen et al. |
| 6,548,817 B1 | 4/2003 | Anders |
| 6,558,383 B2 | 5/2003 | Cunningham |
| 6,562,037 B2 | 5/2003 | Paton et al. |
| 6,629,974 B2 | 10/2003 | Penny et al. |
| 6,657,152 B2 | 12/2003 | Shimazu |

(56) References Cited

U.S. PATENT DOCUMENTS

| | | | |
|---|---|---|---|
| 6,669,106 | B2 | 12/2003 | Delcea |
| 6,676,655 | B2 | 1/2004 | McDaniel et al. |
| 6,780,184 | B2 | 8/2004 | Tanrisever |
| 6,845,929 | B2 | 1/2005 | Dolatabadi et al. |
| 6,886,757 | B2 | 5/2005 | Byrnes et al. |
| 6,958,063 | B1 | 10/2005 | Solt et al. |
| 6,972,138 | B2 | 12/2005 | Heinrich et al. |
| 6,986,471 | B1 | 1/2006 | Kowalsky et al. |
| 7,025,764 | B2 | 4/2006 | Paton et al. |
| 7,030,336 | B1 | 4/2006 | Hawley |
| 7,118,570 | B2 | 10/2006 | Tetzlaff et al. |
| 7,589,473 | B2 | 9/2009 | Suslov |
| 8,043,286 | B2 | 10/2011 | Palanker |
| 8,226,644 | B2 | 7/2012 | Sartor |
| 2001/0041227 | A1 | 11/2001 | Hislop |
| 2002/0013583 | A1 | 1/2002 | Camran et al. |
| 2002/0071906 | A1 | 6/2002 | Rusch |
| 2002/0091385 | A1 | 7/2002 | Paton et al. |
| 2002/0097767 | A1 | 7/2002 | Krasnov |
| 2003/0030014 | A1 | 2/2003 | Wieland et al. |
| 2003/0040744 | A1 | 2/2003 | Latterell et al. |
| 2003/0075618 | A1 | 4/2003 | Shimazu |
| 2003/0114845 | A1 | 6/2003 | Paton et al. |
| 2003/0125728 | A1 | 7/2003 | Nezhat et al. |
| 2003/0178511 | A1 | 9/2003 | Dolatabadi et al. |
| 2003/0190414 | A1 | 10/2003 | Van Steenkiste |
| 2004/0018317 | A1 | 1/2004 | Heinrich et al. |
| 2004/0064139 | A1 | 4/2004 | Yossepowitch |
| 2004/0068304 | A1 | 4/2004 | Paton et al. |
| 2004/0116918 | A1 | 6/2004 | Konesky |
| 2004/0124256 | A1 | 7/2004 | Itsukaichi et al. |
| 2004/0129222 | A1 | 7/2004 | Nylen et al. |
| 2004/0195219 | A1 | 10/2004 | Conway |
| 2005/0082395 | A1 | 4/2005 | Gardega |
| 2005/0120957 | A1 | 6/2005 | Kowalsky et al. |
| 2005/0192610 | A1 | 9/2005 | Houser et al. |
| 2005/0192611 | A1 | 9/2005 | Houser |
| 2005/0192612 | A1 | 9/2005 | Houser et al. |
| 2005/0234447 | A1 | 10/2005 | Paton et al. |
| 2005/0255419 | A1 | 11/2005 | Belashchenko et al. |
| 2006/0004354 | A1 | 1/2006 | Suslov |
| 2006/0037533 | A1 | 2/2006 | Belashchenko et al. |
| 2006/0049149 | A1 | 3/2006 | Shimazu |
| 2006/0090699 | A1 | 5/2006 | Muller |
| 2006/0091116 | A1 | 5/2006 | Suslov |
| 2006/0091117 | A1 | 5/2006 | Blankenship et al. |
| 2006/0091119 | A1 | 5/2006 | Zajchowski et al. |
| 2006/0108332 | A1 | 5/2006 | Belashchenko |
| 2006/0189976 | A1 | 8/2006 | Karni et al. |
| 2006/0217706 | A1 | 9/2006 | Lau et al. |
| 2006/0287651 | A1 | 12/2006 | Bayat |
| 2007/0021747 | A1 | 1/2007 | Suslov |
| 2007/0021748 | A1 | 1/2007 | Suslov |
| 2007/0029292 | A1 | 2/2007 | Suslov |
| 2007/0038214 | A1 | 2/2007 | Morley et al. |
| 2007/0138147 | A1 | 6/2007 | Molz et al. |
| 2007/0173871 | A1 | 7/2007 | Houser et al. |
| 2007/0173872 | A1 | 7/2007 | Neuenfeldt |
| 2007/0191828 | A1 | 8/2007 | Houser et al. |
| 2008/0015566 | A1 | 1/2008 | Livneh |
| 2008/0071206 | A1 | 3/2008 | Peters |
| 2008/0114352 | A1 | 5/2008 | Long et al. |
| 2008/0185366 | A1 | 8/2008 | Suslov |
| 2008/0246385 | A1 | 10/2008 | Schamiloglu et al. |
| 2009/0039789 | A1 | 2/2009 | Suslov |
| 2009/0039790 | A1* | 2/2009 | Suslov ............... A61B 18/042 315/111.21 |
| 2009/0089742 | A1 | 9/2009 | Suslov |
| 2010/0089742 | A1 | 4/2010 | Suslov |

FOREIGN PATENT DOCUMENTS

| | | |
|---|---|---|
| CA | 983586 | 2/1979 |
| CA | 1144104 | 4/1983 |
| CA | 1308772 | 10/1992 |
| CA | 2594515 | 7/2006 |
| CN | 85107499 B | 4/1987 |
| CN | 1331836 A | 1/2002 |
| CN | 1557731 | 12/2004 |
| CN | 1682578 | 10/2005 |
| DE | 2033072 | 2/1971 |
| DE | 10127261 | 9/1993 |
| DE | 4209005 | 12/2002 |
| DE | 10 2007 040434 A1 | 3/2009 |
| EP | 0282677 | 12/1987 |
| EP | 0411170 | 2/1991 |
| EP | 0748149 | 12/1996 |
| EP | 0851040 | 7/1998 |
| EP | 1293169 | 3/2003 |
| EP | 1570798 | 9/2005 |
| ES | 2026344 | 4/1992 |
| FR | 2193299 | 2/1974 |
| FR | 2567747 | 1/1986 |
| GB | 0751735 | 7/1956 |
| GB | 0921016 | 3/1963 |
| GB | 1125806 | 9/1968 |
| GB | 1176333 | 1/1970 |
| GB | 1268843 | 3/1972 |
| GB | 2407050 | 4/2005 |
| JP | 47009252 | 3/1972 |
| JP | 54120545 | 2/1979 |
| JP | 57001580 | 1/1982 |
| JP | 57068269 | 4/1982 |
| JP | 6113600 A | 1/1986 |
| JP | 62123004 | 6/1987 |
| JP | 1319297 | 12/1989 |
| JP | 06262367 | 9/1994 |
| JP | 52-117255 A | 10/1997 |
| JP | 09299380 | 11/1997 |
| JP | 10024050 | 1/1998 |
| JP | 10234744 | 9/1998 |
| JP | 10504751 | 12/1998 |
| JP | 2002541902 | 12/2002 |
| JP | 2009541902 | 12/2002 |
| JP | 2008036001 | 2/2008 |
| JP | 2008-284580 | 11/2008 |
| MX | PA 04010281 | 6/2005 |
| RU | 2178684 | 1/2002 |
| RU | 2183480 | 6/2002 |
| RU | 2183946 | 6/2002 |
| WO | WO 92/019166 | 11/1992 |
| WO | WO 96/006572 | 3/1996 |
| WO | WO 97/011647 | 4/1997 |
| WO | WO 01/062169 | 8/2001 |
| WO | WO 02/030308 | 4/2002 |
| WO | WO 2003/028805 | 4/2003 |
| WO | WO 04/028221 | 4/2004 |
| WO | WO 04/030551 | 4/2004 |
| WO | WO 04/105450 | 12/2004 |
| WO | WO 05/099595 | 10/2005 |
| WO | WO 06/012165 | 2/2006 |
| WO | WO 07/006516 | 1/2007 |
| WO | WO 07/006517 | 1/2007 |
| WO | WO 2007/003157 | 1/2007 |
| WO | WO 07/040702 | 4/2007 |
| WO | WO 09/018837 | 2/2009 |

OTHER PUBLICATIONS

Office Action of U.S. Appl. No. 12/696,411, dated Dec. 5, 2012.
Chinese Office Action of application No. 200780052471.5, dated Dec. 5, 2012.
Japanese Office Action of application No. 2009-547536, dated Feb. 15, 2012.
Office Action of U.S. Appl. No. 13/357,895, dated Mar. 29, 2012.
Chinese Office Action of application No. 200780100857.9, dated Nov. 28, 2011 (with translation).
Office Action of U.S. Appl. No. 11/482,580, dated Apr. 11, 2012.
Office Action of U.S. Appl. No. 13/358,934, dated Apr. 24, 2012.
Office Action of U.S. Appl. No. 11/890,937, dated Apr. 3, 2013.
Notice of Allowance and Fees Due of U.S. Appl. No. 13/357,895, dated Feb. 21, 2013.

(56) References Cited

OTHER PUBLICATIONS

International Search Report of application No. PCT/EP2010/060641, dated Apr. 14, 2011.
Written Opinion of International application No. PCT/EP2010/060641, dated Apr. 14, 2011.
Japanese Office Action of application No. 2010-519340, dated Mar. 13, 2012 (with translation).
Chinese Office Action of application No. 200780100858.3, dated Apr. 27, 2012 (with translation).
Japanese Office Action of application No. 2010-519339, dated Apr. 3, 2012 (with translation).
Office Action of U.S. Appl. No. 11/482,582, dated May 23, 2011.
Notice of Allowance of U.S. Appl. No. 12/557,645, dated May 26, 2011.
Chinese Office Action of application No. 200780100857.9, dated May 30, 2013 (with translation).
Canadian Office Action of Canadian Appl. No. 2,695,650, dated Jun. 18, 2013.
Canadian Office Action of Canadian Appln. No. 2,695,902, dated Jun. 12, 2013.
Examiner's Answer to Applicant's Appeal Brief in U.S. Appl. No. 11/482,58, dated Jun. 18, 2013.
Chinese Office Action of application No. 200780052471.5, dated May 25, 2012 (with translation).
Chinese Office Action of application No. 200780100857.9, dated May 25, 2012 (with translation).
510(k) Summary, dated Jun. 2, 2008.
510(k) Summary, dated Oct. 30, 2003.
510(k) Notification (21 CFR 807.90(e)) for the Plasma Surgical Ltd. PlasmaJet® Neutral Plasma Surgery System, Section 10—Executive Summary—K080197.
Aptekman, 2007, "Spectroscopic analysis of the PlasmaJet argon plasma with 5mm-0.5 coag-cut handpieces", Document PSSRP-106—K080197.
Asawanonda et al., 2000, "308-nm excimer laser for the treatment of psoriasis: a dose-response study." Arach. Deitnatol. 136:619-24.
Branson, M.D., 2005, "Preliminary experience with neutral plasma, a new coagulation technology, in plastic surgery", Fayetteville, NY.
Charpentier et al., 2008, "Multicentric medical registry on the use of the Plasma Surgical PlasmaJet System in thoracic surgery", Club Thorax.
Chen et al., 2006, "What do we know about long laminar plasma jets?", Pure Appl Chem; 78(6):1253-1264.
Cheng et al., 2006, "Comparison of laminar and turbulent thermal plasma jet characteristics—a modeling study", Plasma Chem Plasma Process; 26:211-235.
CoagSafe™ Neutral Plasma Coagulator Operator Manual, Part No. OMC-2100-1, Revision 1.1, dated Mar. 2003—Appendix 1of K030819.
Coven et al., 1999, "PUVA-induced lymphocyte apoptosis: mechanism of action in psoriasis." Photodeitnatol. Photoimmunol. Photomed. 15:22-7.
Dabringhausen et al., 2002, "Determination of HID electrode falls in a model lamp I: Pyrometric measurements." J. Phys. D. Appl. Phys. 35:1621-1630.
Davis (ed), 2004, ASM Thermal Spray Society, Handbook of Thermal Spray Technology, U.S. 42-168.
Deb et al., "Histological quantification of the tissue damage caused in vivo by neutral PlasmaJet coagulator", Nottingham University Hospitals, Queen's medical Centre, Nottingham NG7 2UH—Poster, dated Oct. 2009.
Electrosurgical Generators Force FX™ Electrosurgical Generators by ValleyLab—K080197, dated Sep. 2002.
ERBE APC 300 Argon Plasma Coagulation Unit for Endoscopic Applications, Brochure—Appendix 4 of K030819.
Feldman et al., 2002, "Efficacy of the 308-nm excimer laser for treatment of psoriasis: results of a multicenter study." J. Am Acad. Dermatol. 46:900-6.
Force Argon™ II System, Improved precision and control in electrosurgery, by Valleylab—K080197.

Gerber et al., 2003, "Ultraviolet B 308-nm excimer laser treatment of psoriasis: a new phototherapeutic approach." Br. J. Dermatol. 149:1250-8.
Gugenheim et al., 2006, "Open, muliticentric, clinical evaluation of the technical efficacy, reliability, safety, and clinical tolerance of the plasma surgical PlasmaJet System for intra-operative coagulation in open and laparoscopic general surgery", Department of Digestive Surgery, University Hospital, Nice, France.
Haemmerich et al., 2003, "Hepatic radiofrequency ablation with internally cooled probes: effect of coolant temperature on lesion size", IEEE Transactions of Biomedical Engineering; 50(4):493-500.
Haines et al., "Argon neutral plasma energy for laparoscopy and open surgery recommended power settings and applications", Royal Surrey County Hospital, Guildford Surrey, UK.
Honigsmann, 2001, "Phototherapy for psoriasis." Clin. Exp. Dermatol. 26:343-50.
Huang et al., 2008, "Laminar/turbulent plasma jets generated at reduced pressure", IEEE Transaction on Plasma Science; 36(4):1052-1053.
Iannelli et al., 2005, "Neutral plasma coagulation (NPC)—A preliminary report on a new technique for post-bariatric corrective abdominoplasty", Department of Digestive Surgery, University Hospital, Nice, France.
International Preliminary Report on Patentability of International application No. PCT/EP2007/006939, dated Feb. 9, 2010.
International Preliminary Report on Patentability of International application No. PCT/EP2007/006940, dated Feb. 9, 2010.
International Preliminary Report on Patentability of International application No. PCT/EP2007/000919, dated Aug. 4, 2009.
International-type Search report dated Jan. 18, 2006, Swedish App. No. 0501603-5.
International-type Search report dated Jan. 18, 2006, Swedish App. No. 0501602-7.
International-type Search Report, dated Jan. 18, 2006, Swedish App. No. 0501604-3.
Letter to FDA re: 501(k) Notification (21 CFR 807.90(e)) for the PlasmaJet® Neutral Plasma Surgery System, dated Jun. 2, 2008—K080197.
Lichtenberg et al., 2002, "Observation of different modes of cathodic arc attachment to HID electrodes in a model lamp." J. Phys. D. Appl. Phys. 35:1648-1656.
Marino, M.D., "A new option for patients facing liver resection surgery", Thomas Jefferson University Hospital.
McClurken et al., "Collagen shrinkage and vessel sealing", TissueLink Medical, Inc., Dover, NH; Technical Brief #300.
McClurken et al., "Histologic characteristics of the TissueLink Floating Ball device coagulation on porcine liver", TissueLink Medical, Inc., Dover, NH; Pre-Clinical Study #204.
Merloz, 2007, "Clinical evaluation of the Plasma Surgical PlasmaJet tissue sealing system in orthopedic surgery—Early report", Orthopedic Surgery Department, University Hospital, Grenoble, France.
News Release and Video—2009, New Sugical Technology Offers Better Outcomes for Women's Reproductive Disorders: Stanford First in Bay Area to Offer PlasmaJet, Stanford Hospital and Clinics.
Nezhat et al., 2009, "Use of neutral argon plasma in the laparoscopic treatment of endometriosis", Journal of the Society of Laparoendoscopic Surgeons.
Notice of Allowance dated May 15, 2009, of U.S. Appl. No. 11/890,938.
Office Action dated Apr. 17, 2008 of U.S. Appl. No. 11/701,911.
Office Action dated Feb. 1, 2008 of U.S. Appl. No. 11/482,580.
Office Action dated Mar. 13, 2009 of U.S. Appl. No. 11/701,911.
Office Action dated Mar. 19, 2009 of U.S. Appl. No. 11/482,580.
Office Action dated Oct. 18, 2007 of U.S. Appl. No. 11/701,911.
Office Action dated Oct. 19, 2009 of U.S. Appl. No. 11/482,580.
Office Action dated Sep. 17, 2009 of U.S. Appl. No. 11/890,937.
Office Action dated Sep. 29, 2009 of U.S. Appl. No. 11/701,911.
Office Action dated Apr. 2, 2010 of U.S. Appl. No. 11/701,911.
Office Action dated Apr. 9, 2010 of U.S. Appl. No. 11/890,937.
Office Action dated Jun. 23, 2010 of U.S. Appl. No. 11/482,582.
Office Action dated Jun. 24, 2010 of U.S. Appl. No. 11/482,581.

(56) References Cited

OTHER PUBLICATIONS

Palanker et al., 2008, "Electrosurgery with cellular precision", IEEE Transactions of Biomedical Engineering; 55(2):838-841.
Pan et al., 2001, "Generation of long, laminar plasma jets at atmospheric pressure and effects of low turbulence", Plasma Chem Plasma Process; 21(1):23-35.
Pan et al., 2002, "Characteristics of argon laminar DC Plasma Jet at atmospheric pressure", Plasma Chem and Plasma Proc; 22(2):271-283.
PCT International Preliminary Report on Patentability and Written Opinion of the International Searching Authority, dated Aug. 4, 2009, International App. No. PCT/EP2007/000919.
PCT International Search Report dated Feb. 14, 2007, International App. No. PCT/EP2006/006688.
PCT International Search Report dated Feb. 22, 2007, International App. No. PCT/EP2006/006689.
PCT International Search Report dated Feb. 22, 2007, of International appl. No. PCT/EP2006/006690.
PCT Written Opinion of the International Searching Authority dated Feb. 22, 2007, International App. No. PCT/EP2006/006690.
PCT International Search Report PCT/EP2007/006939, dated May 26, 2008.
PCT International Search Report PCT/EP2007/006940.
PCT International Search Report, dated Oct. 23, 2007, International App. No. PCT/EP2007/000919.
PCT Invitation to Pay Additional Fees PCT/EP2007/006940, dated May 20, 2008.
PCT Written Opinion of the International Searching Authority PCT/EP2007/006939, dated May 26, 2008.
PCT Written Opinion of the International Searching Authority dated Oct. 23, 2007, International App. No. PCT/EP2007/000919.
PCT Written Opinion of the International Searching Authority PCT/EP2007/006940.
PCT Written Opionin of the International Searching Authority dated Feb. 14, 2007, International App. No. PCT/EP2006/006688.
PCT Written Opionin of the International Searching Authority dated Feb. 22, 2007, International App. No. PCT/EP2006/006689.
Plasma Surgery: A Patient Safety Solution (Study Guide 002), dated Feb. 25, 2010.
Plasma Surgical Headlines Article: Atlanta, Feb. 2, 2010—"New Facilities Open in UK and US".
Plasma Surgical Headlines Article: Atlanta, Feb. 2, 2010—"PlasmaJet to be Featured in Live Case at Endometriosis 2010 in Milan, Italy".
Plasma Surgical Headlines Article: Chicago, Sep. 17, 2008—"PlasmaJet Named Innovation of the Year by the Society of Laparoendoscopic Surgeons".
PlasmaJet English Brochure.
Plasmajet Neutral Plasma Coagulator Operator Manual, Part No. OMC-2100-1 (Revision 1.7, dated May 2004)—K030819.
Plasmajet Neutral Plasma Coagulator Brochure mpb 2100—K080197.
Plasmajet Operator Manual Part No. OMC-2130-EN (Revision 3.1/Draft) dated May 2008—K080197.
Premarket Notification 510(k) Submission, Plasma Surgical Ltd.—PlasmaJet™ (formerly CoagSafe™) Neutral Plasma Coagulator, Additional information provided in response to the e-mail request dated Jul. 14, 2004—K030819.
Premarket Notification 510(k) Submission, Plasma Surgical Ltd. CoagSafe™, Section 4 Device Description—K030819, Mar. 14, 2003.
Premarket Notification 510(k) Submission, Plasma Surgical Ltd. PlasmaJet®, , Section 11 Device Description—K080197, Jan. 2, 2008
Premarket Notification 510(k) Submission, Plasma Surgical Ltd. CoagSafe™, Section 5 Substantial Equivalence—K030819, Mar. 14, 2003.
Report on the comparative analysis of morphological changes in tissue from different organs after using the PlasmaJet version 3 (including cutting handpieces), Aug. 2007—K080197.
Schmitz & Riemann, 2002, "Analysis of the cathode region of atmospheric pressure discharges." J. Phys. D. Appl. Phys. 35:1727-1735.
Severtsev et al., "Comparison of different equipment for final haemostasis of the wound surface of the liver following resection", Dept. of Surgery, Postgraduate and Research Centre, Medical Centre of the Directorate of Presidential Affairs of the Russian Federation, Moscow, Russia—K030819 Jun. 1997.
Sonoda et al., "Pathologic analysis of ex-vivo plasma energy tumor destruction in patients with ovarian or peritoneal cancer", Gynecology Service, Department of Surgery—Memorial Sloan-Kettering Cancer Center, New York, NY—Poster.
The Edge in Electrosurgery From Birtcher, Brochure—Appendix 4 of K030819.
The Valleylab FORCE GSU System, Brochure—Appendix 4 of K030819.
Treat, "A new thermal device for sealing and dividing blood vessels", Dept. of Surgery, Columbia University, New York, NY.
Trehan & Taylor, 2002, "Medium-dose 308-nm excimer laser for the treatment of psoriasis." J. Am. Acad. Dermatol. 47:701-8.
U.S. Appl. No. 12/557,645; Suslov, filed Sep. 11, 2009.
White Paper—A Tissue Study using the PlasmaJet for coagulation: A tissue study comparing the PlasmaJet with argon enhanced electrosurgery and fluid coupled electrosurgery, Oct. 23, 2007.
White Paper—Plasma Technology and its Clinical Application: An introduction to Plasma Surgery and the PlasmaJet—a new surgical technology, Oct. 23, 2010.
www.plasmasurgical.com, as of Feb. 18, 2010.
Zenker, 2008, "Argon plasma coagulation", German Medical Science; 3(1):1-5.
Device drawings submitted pursuant to MPEP §724.
European Office Action of application No. 07786583.0/1226, dated Jun. 29, 2010.
Office Action of U.S. Appl. No. 11/701,911 dated Jul. 19, 2010.
Notice of Allowance and Fees Due of U.S. Appl. No. 12/696,411, dated Aug. 12. 2013.
Final Office Action of U.S. Appl. No. 12/696,411, dated Jun. 10, 2013.
Chinese Office Action (translation) of application No. 200680030225.5, dated Jun. 11, 2010.
Chinese Office Action (translation) of application No. 200680030216.6, dated Oct. 26, 2010.
Chinese Office Action (translation) of application No. 200680030194.3, dated Jan. 31, 2011.
Chinese Office Action (translation) of application No. 200680030225.5, dated Mar. 9, 2011.
Japanese Office Action (translation) of application No. 2008-519873, dated Jun. 10, 2011.
Notice of Allowance and Fees Due of U.S. Appl. No. 13/358,934, dated Sep. 5, 2012.
Office Action of U.S. Appl. No. 13/357,895, dated Sep. 7, 2012.
Chinese Office Action of application No. 200780100858.3, dated Aug. 29, 2012.
Chinese Office Action of Chinese Appl. No. 2012220800745680, dated Nov. 13, 2012.
Office Action U.S. Appl. No. 11/482,580, dated Oct. 24, 2012.
Notice of Allowance and Fees Due of U.S. Appl. No. 11/482,581, Oct. 28, 2011.
Notice of Allowance and Fees Due of U.S. Appl. No. 11/482,582, Sep. 23, 2011.
Supplemental Notice of Allowability of U.S. Appl. No. 11/482,582, Oct. 12, 2011.
Supplemental Notice of Allowability of U.S. Appl. No. 11/482,582, Oct. 25, 2011.
U.S. Appl. No. 12/841,361, filed Jul. 22, 2010, Suslov.
International Search Report of International application No. PCT/EP2010/051130, dated Sep. 27, 2010.
Written Opinion of International application No. PCT/EP2010/051130, dated Sep. 27, 2010.
Severtsev et al. 1997, "Polycystic liver disease: sclerotherapy, surgery and sealing of cysts with fibrin sealant", European Congress of the International Hepatobiliary Association, Hamburg, Geiiiiany Jun. 8-12; p. 259-263.

(56) References Cited

OTHER PUBLICATIONS

Severtsev et al., "Comparison of different equipment for final haemostasis of the wound surface of the liver following resection", Dept. of Surgery, Postgraduate and Research Centre, Medical Centre of the Directorate of Presidential Affairs of the Russian Federation, Moscow, Russia—K030819.
Office Action of U.S. Appl. No. 12/557,645, dated Nov. 26, 2010.
Chinese Office Action of application No. 2007801008583, dated Oct. 19, 2011 (with translation).
Office Action of U.S. Appl. No. 11/482,582, dated Dec. 6, 2010.
Office Action of U.S. Appl. No. 11/482,581, dated Dec. 8, 2010.
Notice of Allowance of U.S. Appl. No. 11/701,911, dated Dec. 6, 2010.
European Office Action of Appl. No. 07/786 582.2-1551, dated Mar. 11, 2015.
European Office Action of Appl. No. 10/ 734 147.1-1551, dated Oct. 28, 2015.
Extended European Search Report dated Aug. 8, 2017 for European Application No. EP 16 20 3010, 5 pages.
Non-Final Office Action dated Feb. 8, 2018 for U.S. Appl. No. 14/810,032, 9 pages.
Non-Final Office Action dated Jan. 3, 2018 for U.S. Appl. No. 14/810,102, 8 pages.

\* cited by examiner

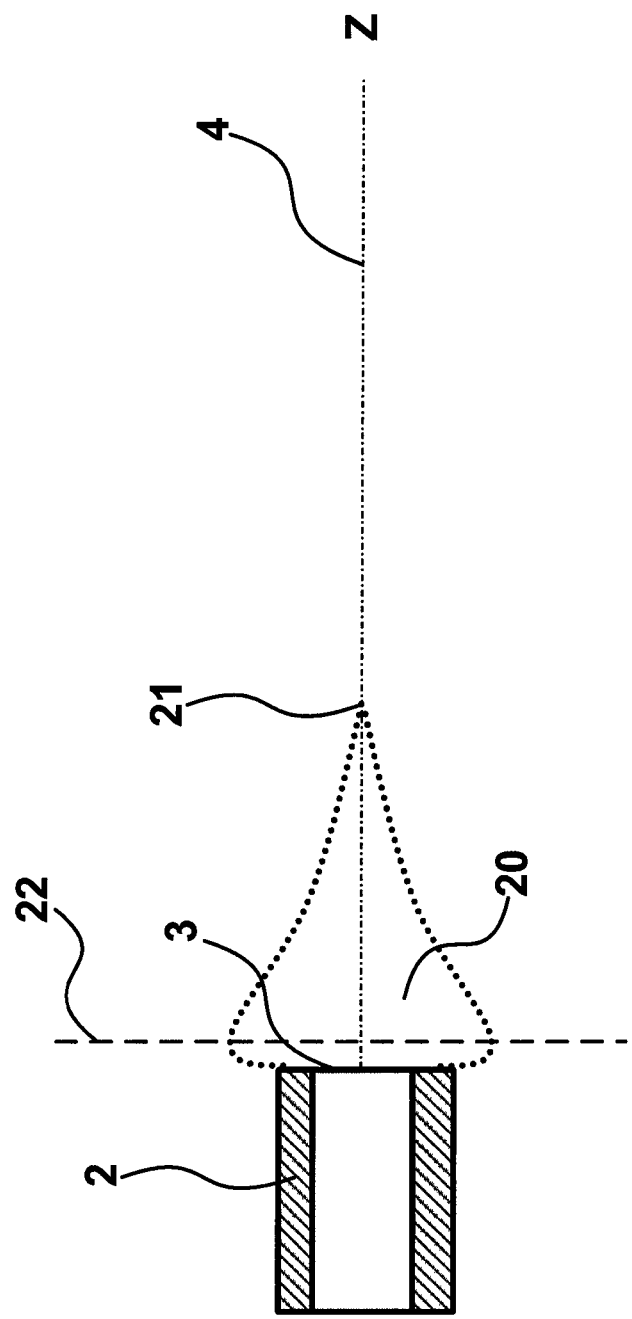

75

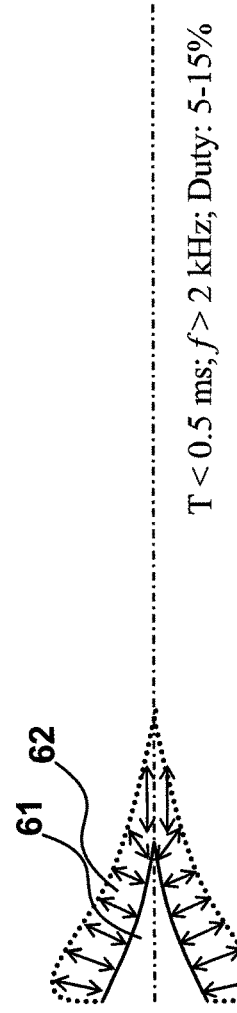
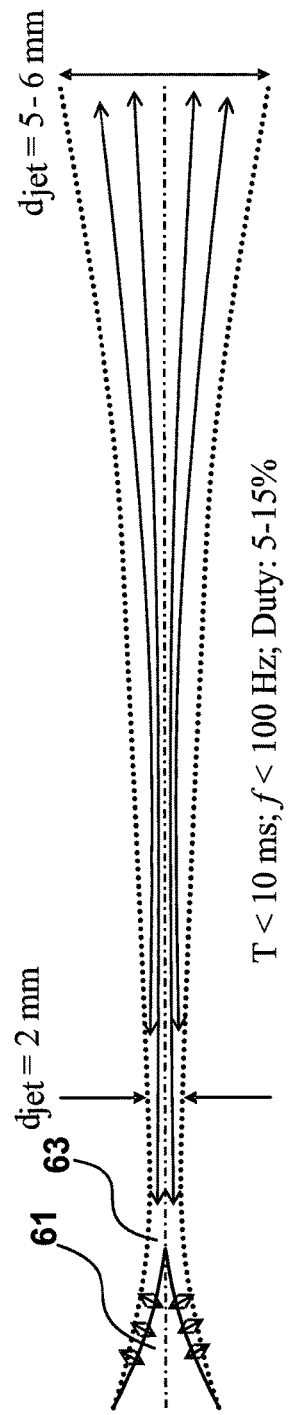
FIG. 18A
FIG. 18B
FIG. 18C

100

100

100

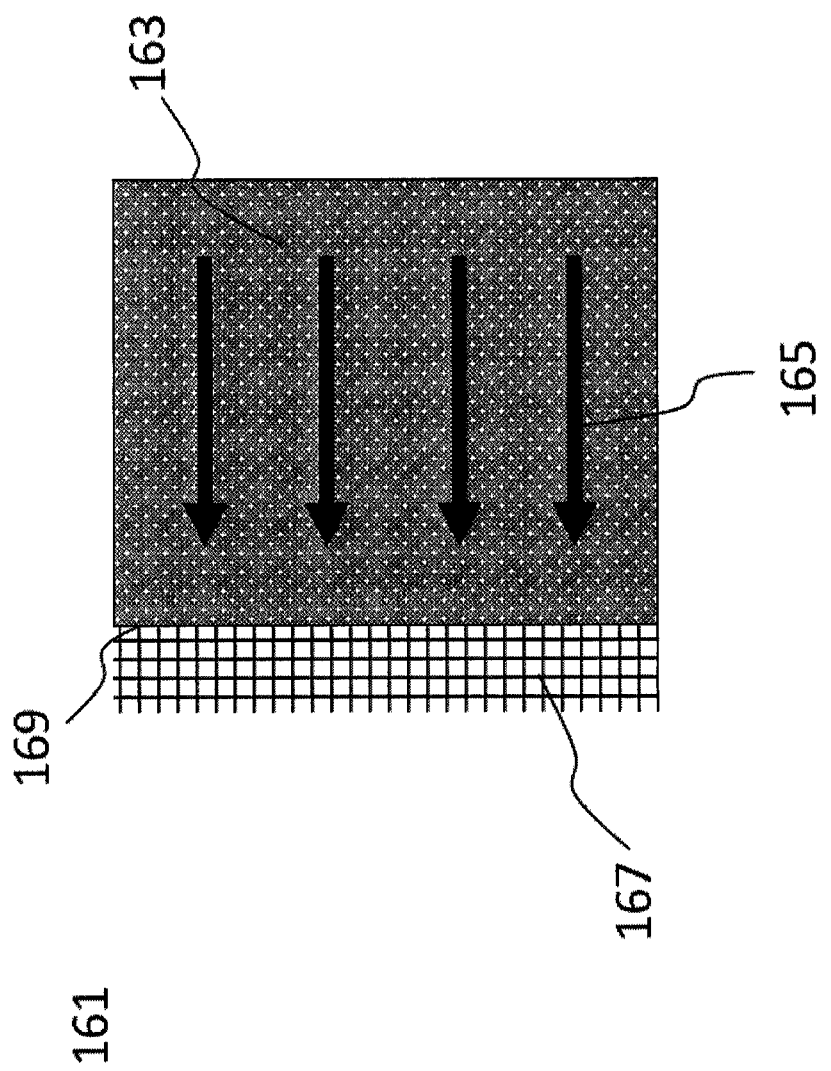

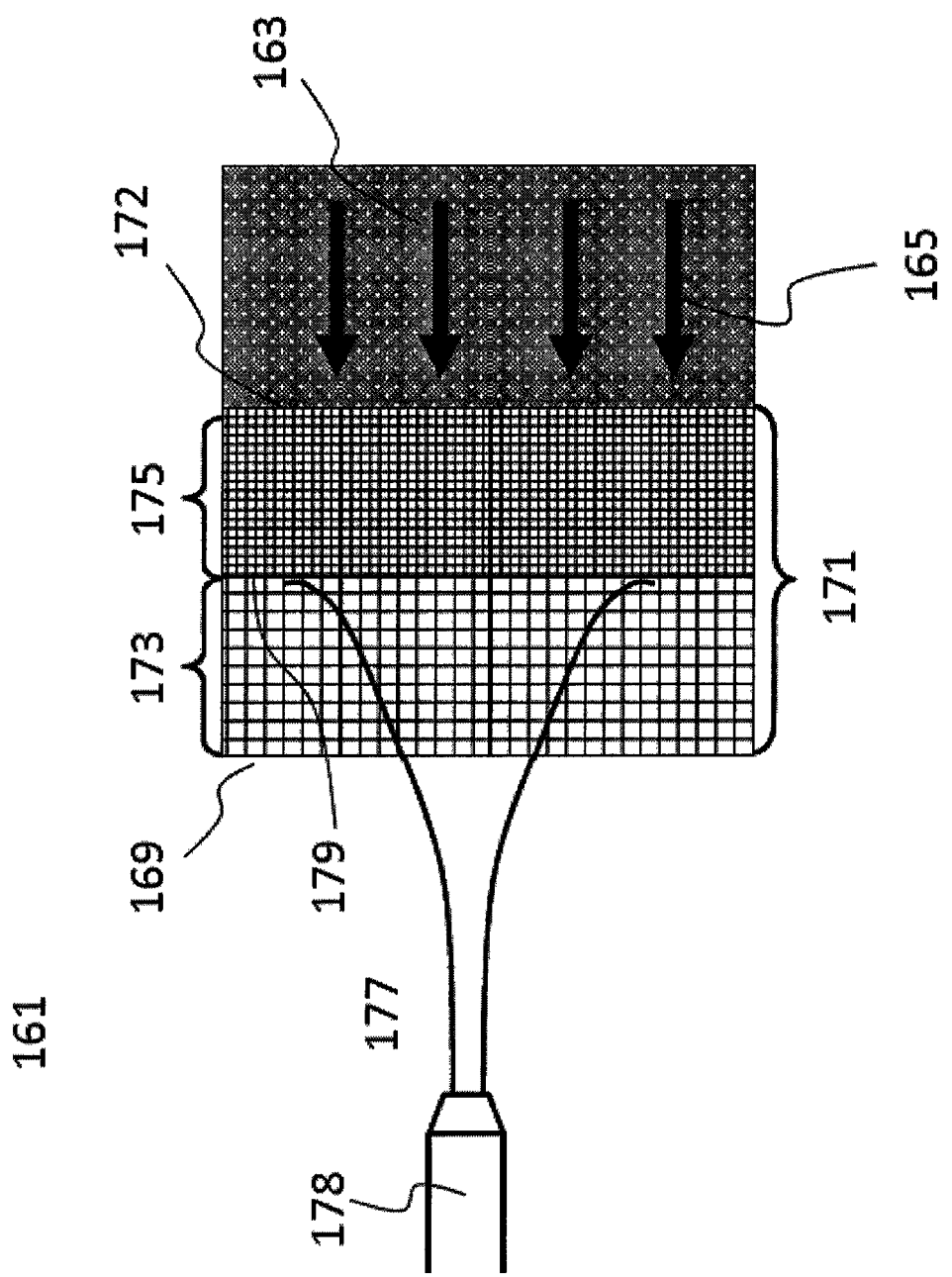

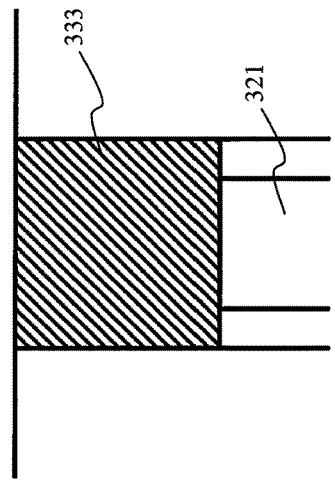
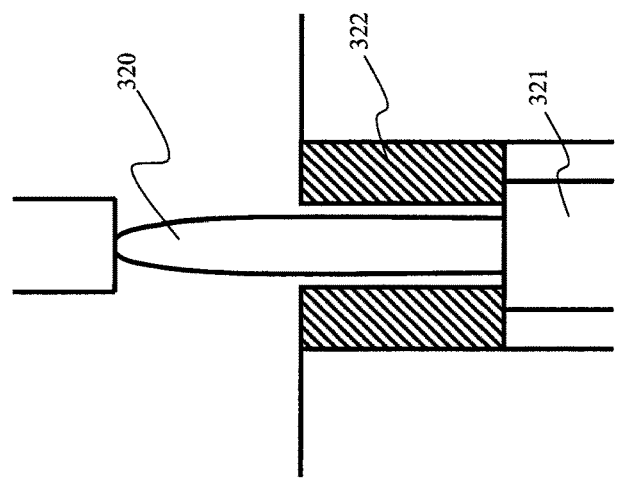
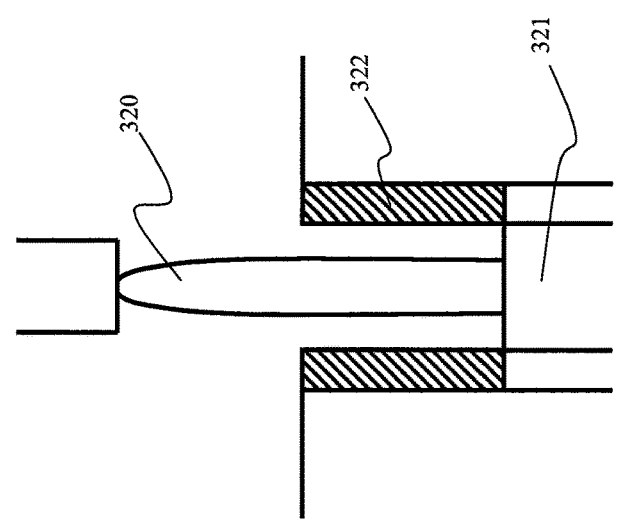
FIG. 43C
FIG. 43B
FIG. 43A

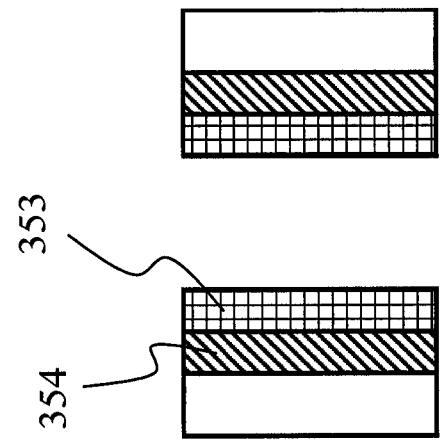
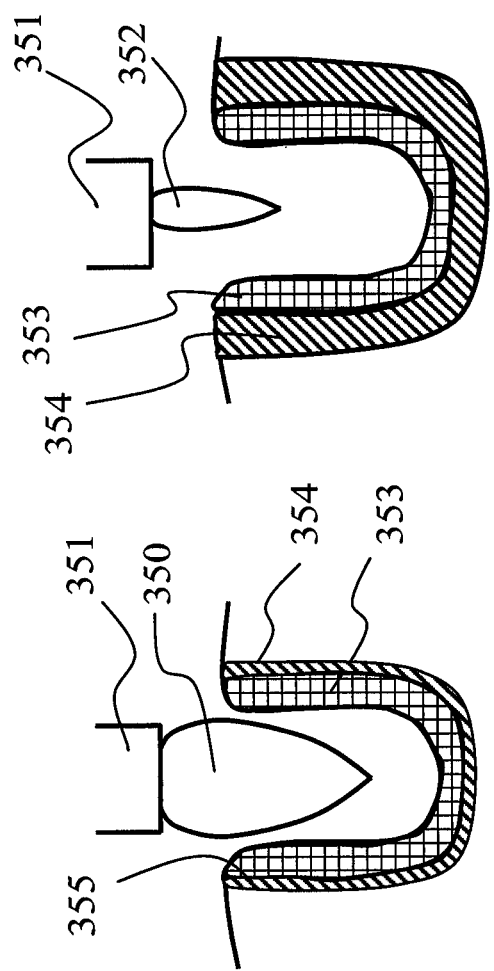
FIG. 46C
FIG. 46B
FIG. 46A

VOLUMETRICALLY OSCILLATING PLASMA FLOWS

This application is a divisional of U.S. patent application Ser. No. 12/841,361, filed Jul. 22, 2010, issuing as U.S. Pat. No. 9,089,319, the disclosure of which is incorporated by reference herein in its entirety for all purposes.

1 FIELD OF INVENTION

The present invention relates to volumetrically oscillating plasma flows. Additionally, the present invention relates to systems and methods for generating volumetrically oscillating plasma flows and to practical applications of the volumetrically oscillating plasma flows.

2 BACKGROUND

Plasma generating devices play an important role in many areas. For example, plasma is used in displays, such as television sets and computer monitors, spectrography, in spraying applications such as coating, and in medicine. In medicine, plasma is used for pain relief, prevention of infection spread, and surgery.

Three basic tasks that a surgeon performs during a surgery are cutting, vaporizing and coagulating tissue. Generally, cutting refers to the separation of the tissue; vaporization refers to the controlled destruction of tissue; and coagulation refers to the stopping of bleeding from the tissue or blood vessels in the tissue. Most open, and even laparoscopic, surgeries involve cutting and coagulating tissue. Some surgeries, such as the removal of tumor nodules, also involve vaporizing tissue.

The use of plasma to accomplish these three tasks is known in the art. In general, to accomplish these tasks, a plasma flow is directed at the treated tissue, which accomplishes certain thermal effects in the tissue. For cutting and vaporization these thermal effects are the sublimation and removal of tissue. For coagulation, the desired thermal effect is the creation of a sealing layer of necrotic tissue that prevents further bleeding. Although plasma is considered to be a superior way of accomplishing the three tasks, some problems with using plasma still remain.

Presently, a surgeon typically uses a dedicated device for each of the three surgical tasks. While this ensures that each device is well adapted to the function it is performing, switching from one task to another requires changing devices. In a typical procedure the surgeon will constantly need to switch from one function to the other, as cutting and vaporizing tissue exposes new bleeding tissue that must be coagulated. Changing devices during surgery adds to the duration and complexity of the procedure, and increases the risk to the patient. In laparoscopic surgery in particular, where the devices are miniaturized and are inserted into the patient's body cavities, changing devices frequently is problematic. Presently, there are no known devices capable of performing all three functions well enough for a surgeon to forgo the use of specialized devices in favor of a single, all-in-one, device.

Even the use of specialized plasma surgical devices has underlying problems. For example, a plasma device specifically adopted for cutting had to have a small outlet diameter that results in a turbulent plasma flow suitable for cutting. The small outlet diameter makes such devices unusable for coagulation that generally requires relatively large spot diameter. Further, cutting of the tissue with such a device results in bleeding that not only impairs the surgeon's visibility of the treated tissue, but, if not timely stopped, was dangerous to the patient. As another example, plasma devices adopted for coagulation could not stop high-rate bleedings. Stopping even medium-rate bleeding requires significant experience with the device.

Accordingly, there is a need in the art for systems and methods that allows improved control over the volumetric properties of plasma flows. In particular, there is a need for systems and methods that would accomplish the three surgical tasks of cutting, vaporization, and coagulation. Preferably, the system and method would perform the three surgical tasks at least as well as the presently known devices.

3 SUMMARY OF THE INVENTION

This need is fulfilled by volumetrically oscillating plasma flow as well as systems and methods for their generations. Specifically, a volumetrically oscillating plasma flow is a plasma flow in air, the flow having a directional axis and an active zone defined by plasma having a temperature above a threshold, wherein the active zone expands and contracts volumetrically over time according to a controlled pattern. The volumetric oscillations process comprises controllably expanding a zone of a plasma flow having a temperature above a threshold and controllably contracting the zone of a plasma flow having a temperature above the threshold the plasma flow.

A system for generating volumetrically oscillating plasma flow comprises a power supply capable of generating an electric current having a non-zero low current level and pulses reaching a high current level (up to 50 A), wherein the pulses have a ramp rate of at least 25 A per 10 µs, and a plasma-generating device capable of (1) heating a plasma-generating gas to a first temperature with the low current level of the electric current, wherein the first temperature is at least 10,000 K, (2) heating the plasma-generating gas to a second temperature with the high level of the electric current, wherein the second temperature is at least 10,000 K above the first temperature; and (3) discharging the heated plasma-generating gas as a plasma flow that expands in volume during the electric current pulses. The plasma-generating device comprises an anode forming a portion of a plasma channel having an outlet with a diameter 0.3-0.8 mm. The plasma-generating gas is supplied to the plasma-generating device at a flow rate of 0.1-0.6 L/min at room temperature. The plasma-generating device may contain a cooling channel with an outlet near the outlet of the plasma channel capable of discharging a coolant. Additionally, the plasma-generating device may comprise a cathode assembly comprising multiple cathodes.

A method for generating a plasma flow whose volume varies with time using a plasma-generating-device having an outlet is also provided. The method comprises: (1) supplying a plasma-generating gas to the plasma-generating device, (2) providing an energy with a power density to the plasma-generating gas to form a plasma flow, wherein the power density changes according to a controlled pattern having a low level and a high level, and (3) discharging from the outlet of the plasma-generating device the volumetrically variable plasma flow alternating between a low intensity plasma with a temperature at the outlet of at least 10,000 K, and a high intensity plasma with a temperature at the outlet of at least 10,000 K above the temperature of the low intensity plasma at the outlet, and wherein the low intensity plasma corresponds to the energy with the low level power density and the high intensity plasma corresponds to the energy with the high intensity power density level.

For medical applications the threshold defining the active plasma zone is about 10,000 K. A portion of the plasma when the active zone is contracted has a first temperature of at least 10,000 K, and the portion of the plasma when the active zone is expanded has a second temperature at least 10,000 K above the first temperature. The controlled pattern may be provided by a power supply capable of generating a current wave that has a low current level of 3-10 A and pulses reaching a high current level of 25-30 A. The ramp rate of the pulses is at least 25 A per 10 µs. Depending on the application, the current wave may be a high frequency biased pulse current wave with a frequency of above 2,000 Hz (preferably above 20,000 Hz) and a duty cycle of 0.05-0.15, a low frequency biased pulse current wave with a frequency of 20-100 Hz and a duty cycle of 0.05-0.15, or a modulated biased pulse current wave in which a high frequency wave is modulated by a low frequency wave with a duty cycle of the high frequency wave being 0.35-0.65 and the duty cycle of the low frequency wave being 0.05-0.15.

Applications of volumetrically oscillating plasma flows include surgical applications, such as the tasks of tissue cutting, coagulation and vaporization. For cutting, a high frequency biased pulse wave is used and the operator moves the device adjacent to the tissue to make a cut. For a frequency above 20,000 Hz, the dissected tissue is coagulated during cutting due to the cavitation effect in the tissue created by ultrasonic acoustic waves generated at this frequency. This cavitation effect also improves blood vessel sealing. For the task of vaporization, a high frequency biased pulse wave is used. The operator moves the device at a distance of about 2-5 mm from the tissue. For frequencies above 20,000 Hz, the tissue is immediately coagulated and the vessels are sealed as they become exposed. For the task of coagulation a low frequency biased pulse wave is used. The operator holds the device at the distance of about 10-30 mm from the tissue. For improved coagulation effect, a modulated biased pulse wave is used to create the cavitation effect from the improved coagulation and vessel sealing. The same system can be used for all three surgical tasks of cutting, vaporizing and coagulation.

Likewise volumetrically oscillating plasma flows may be used for non-surgical applications, such as pain management, cosmetics, waste disposal, surface cleaning and others.

4 BRIEF DESCRIPTION OF THE DRAWINGS

FIG. 3 illustrates the volume of active plasma for a typical plasma flow;

Figure 5:
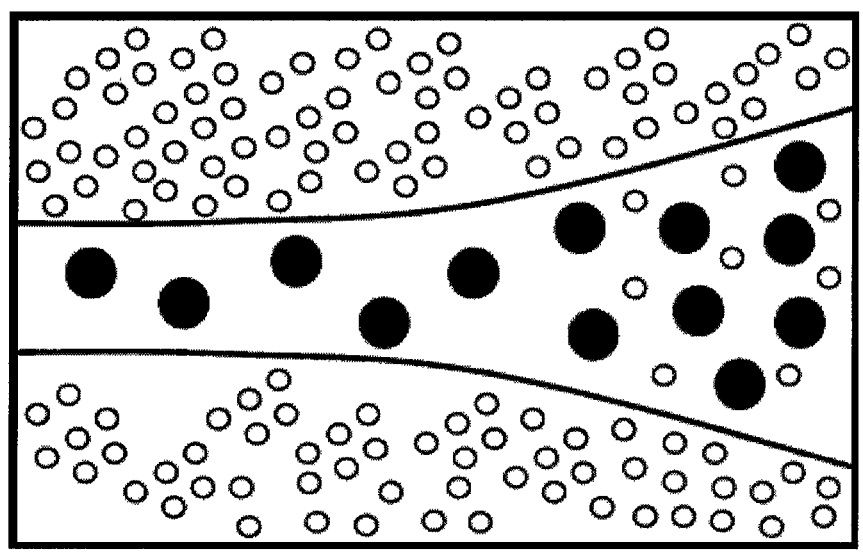
Figure 6:
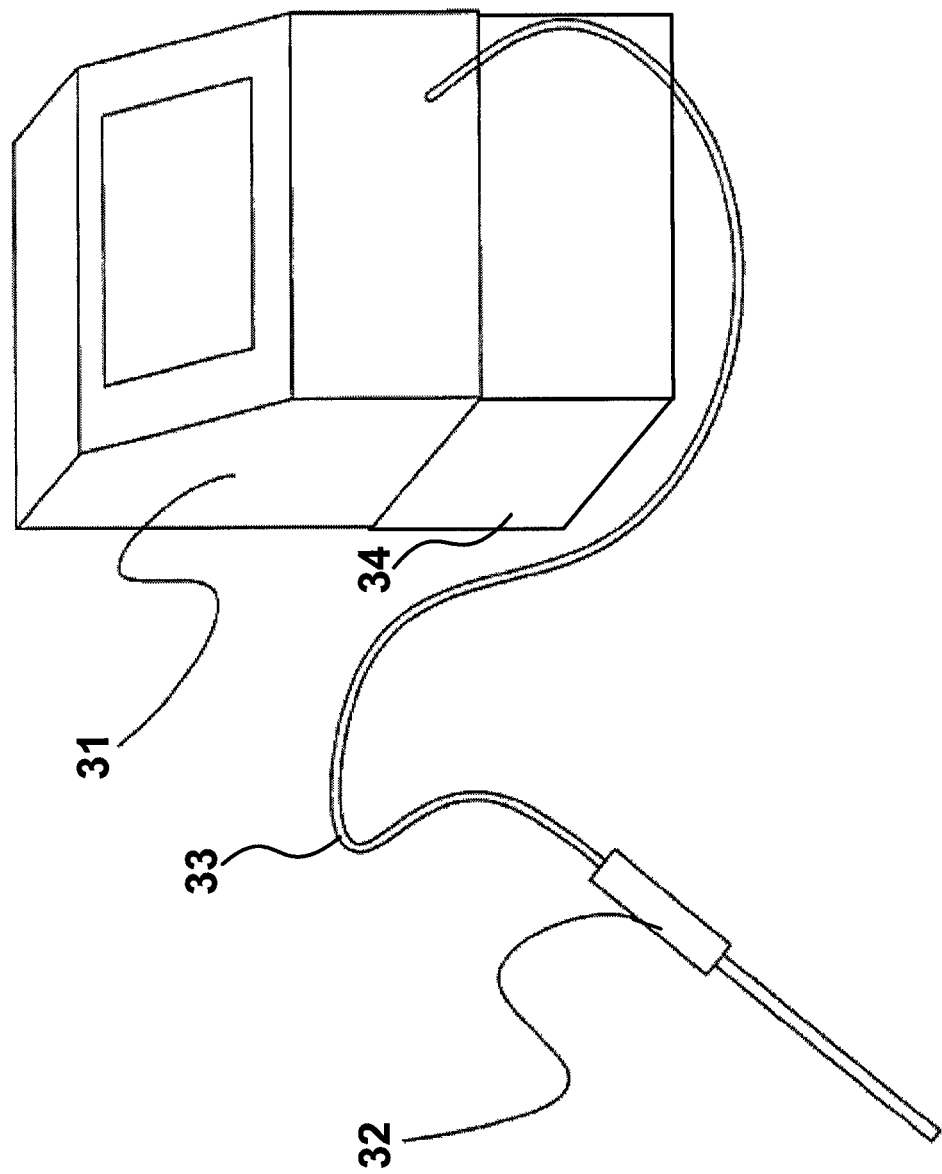
Figure 7:
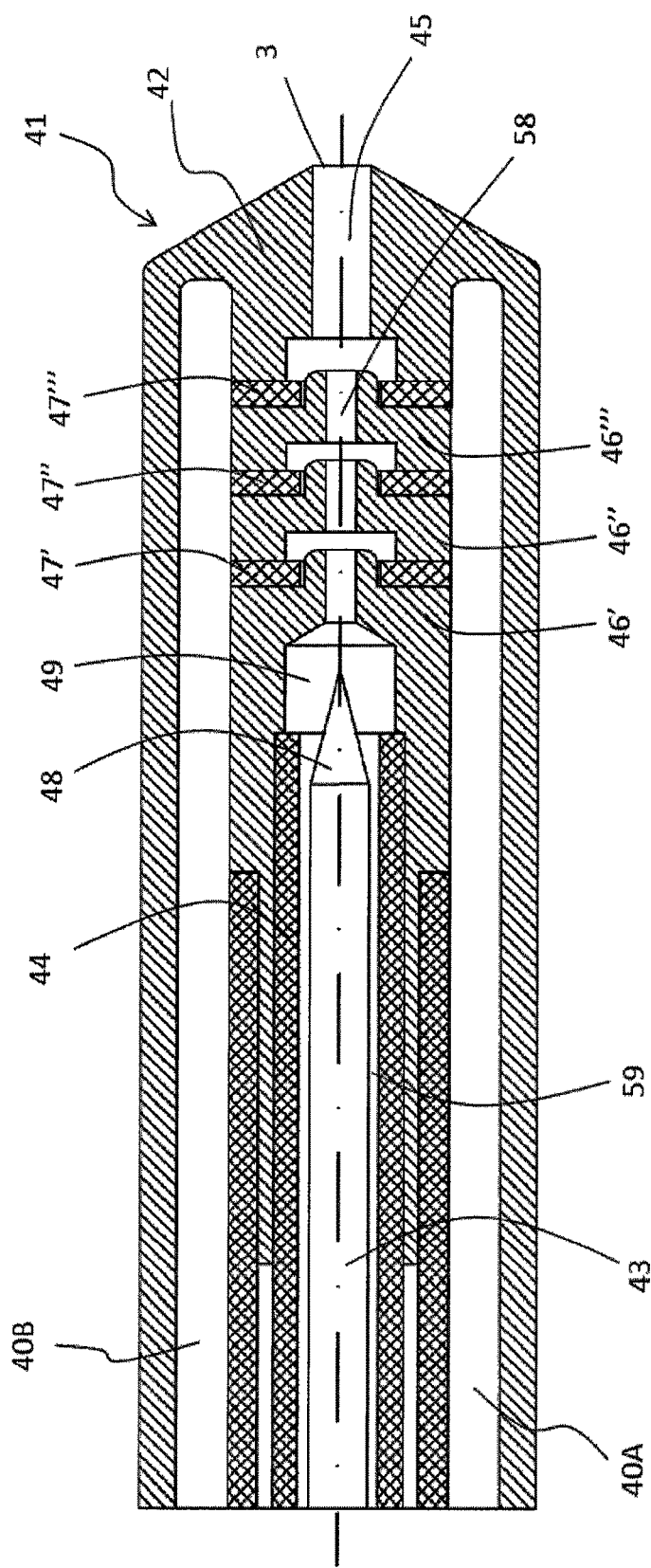
Figure 8:
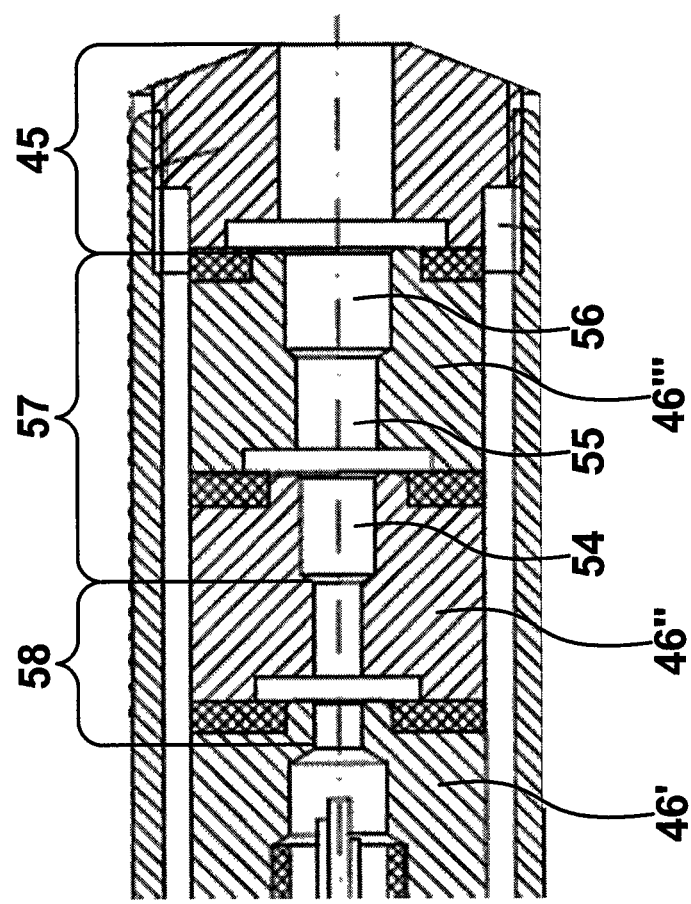
Figure 9:
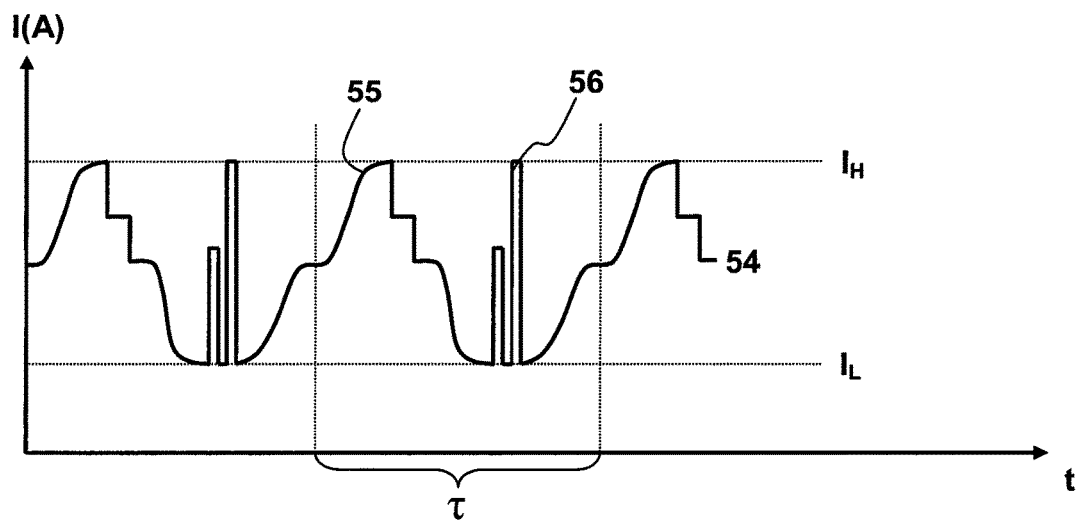
Figure 10:
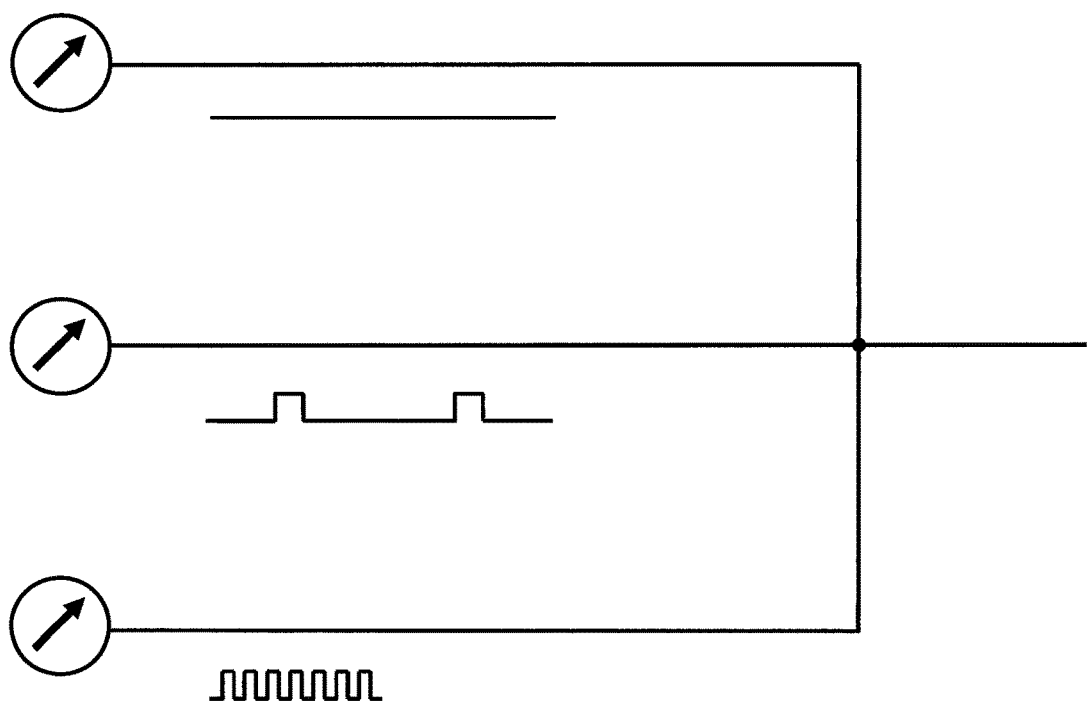
Figure 11:
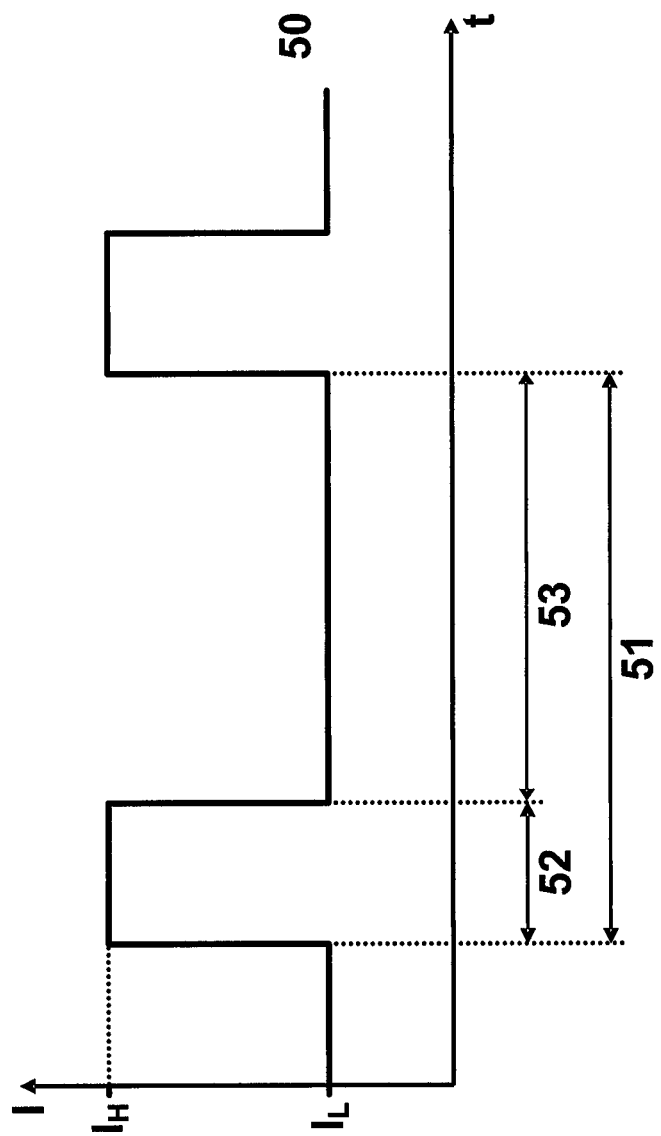
Figure 12:
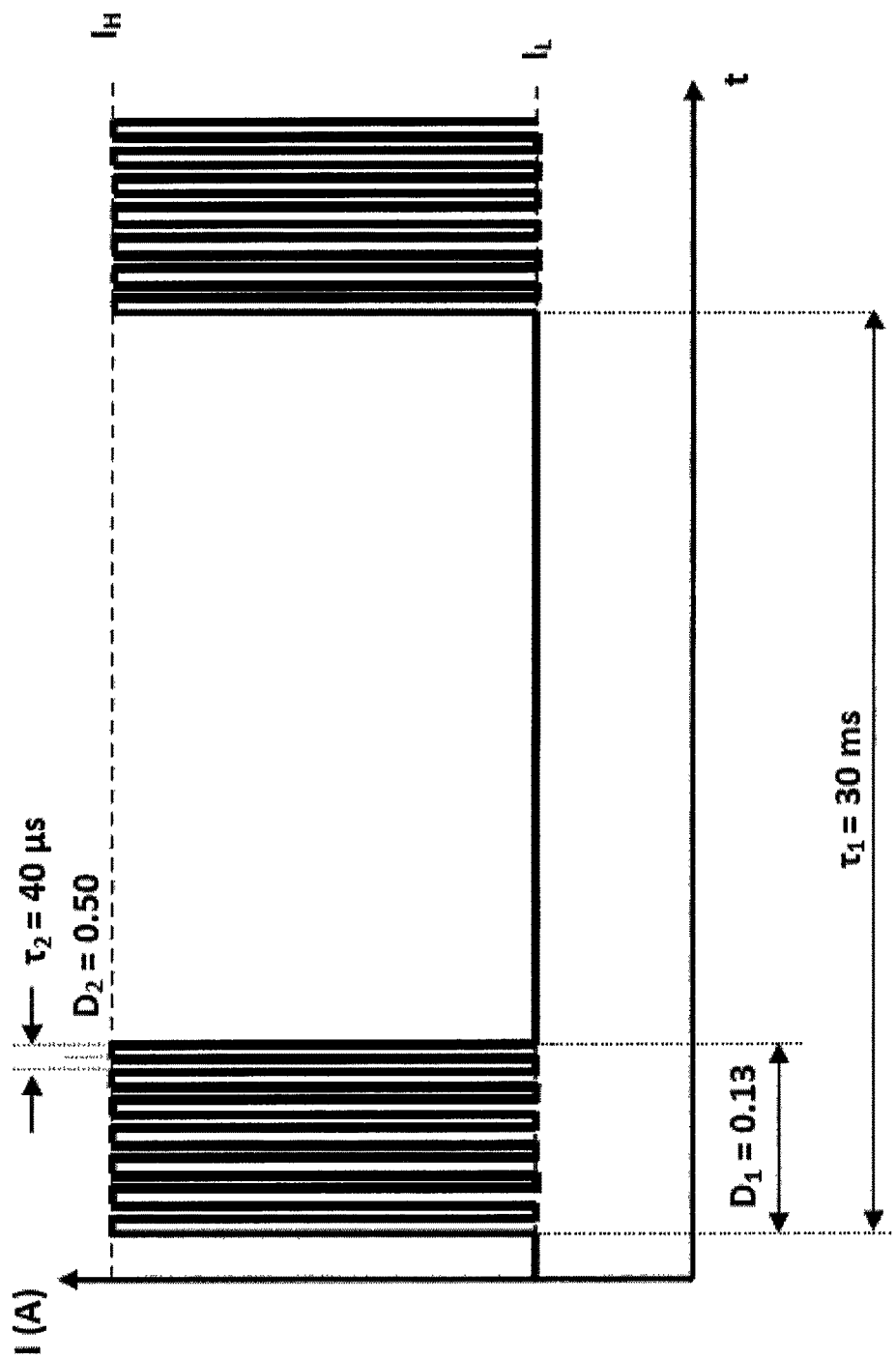
Figure 13A:
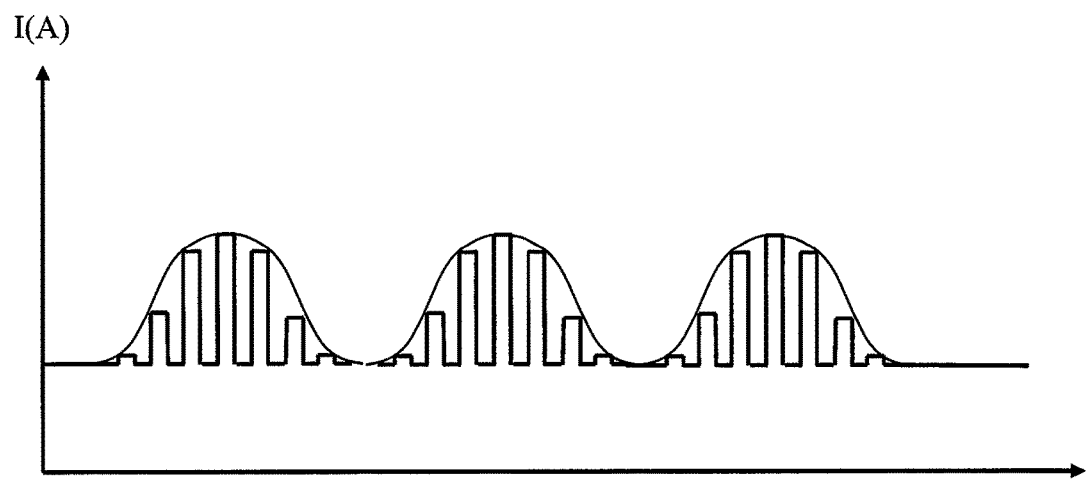
Figure 13B:
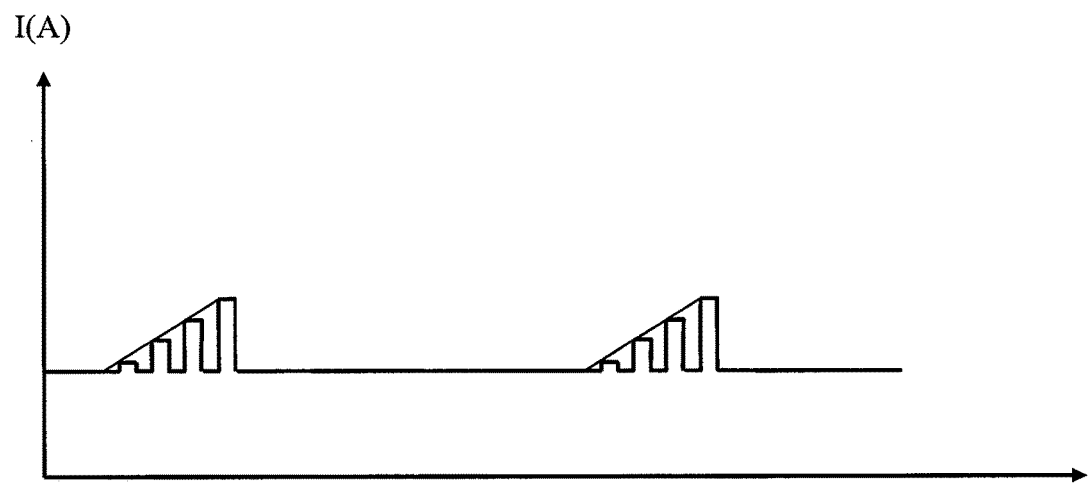
Figure 14A:
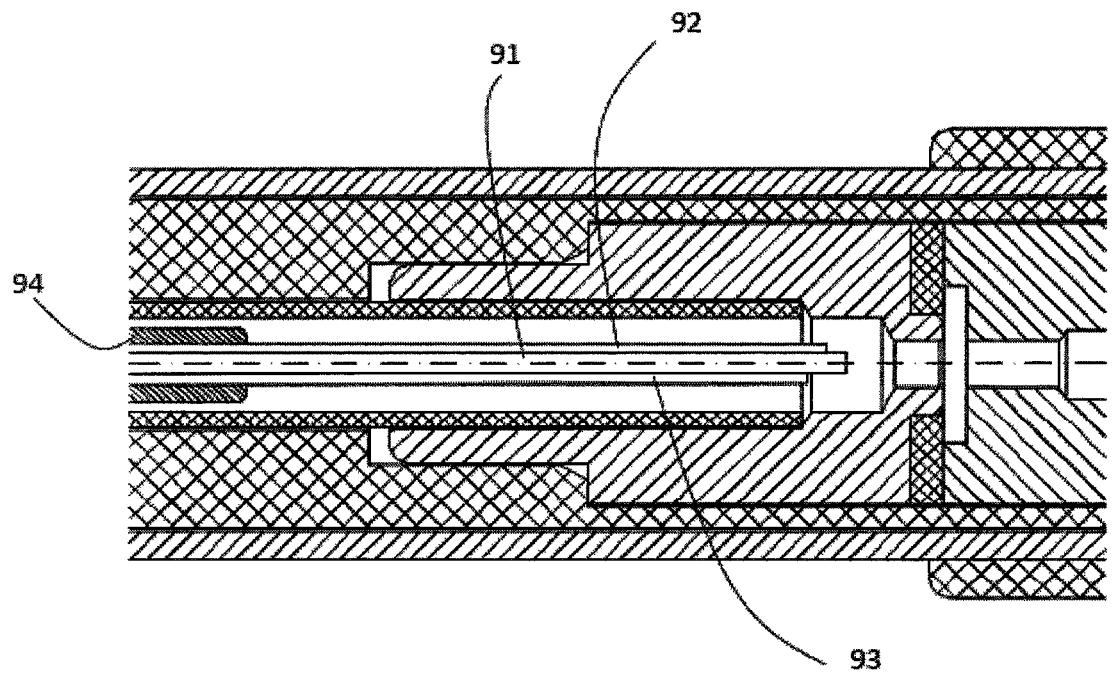
Figure 14B:
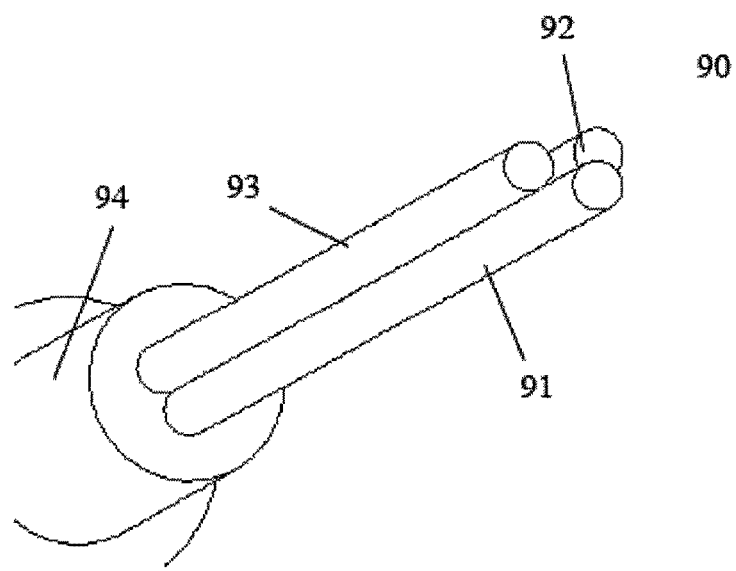
Figures 15A, 15B:
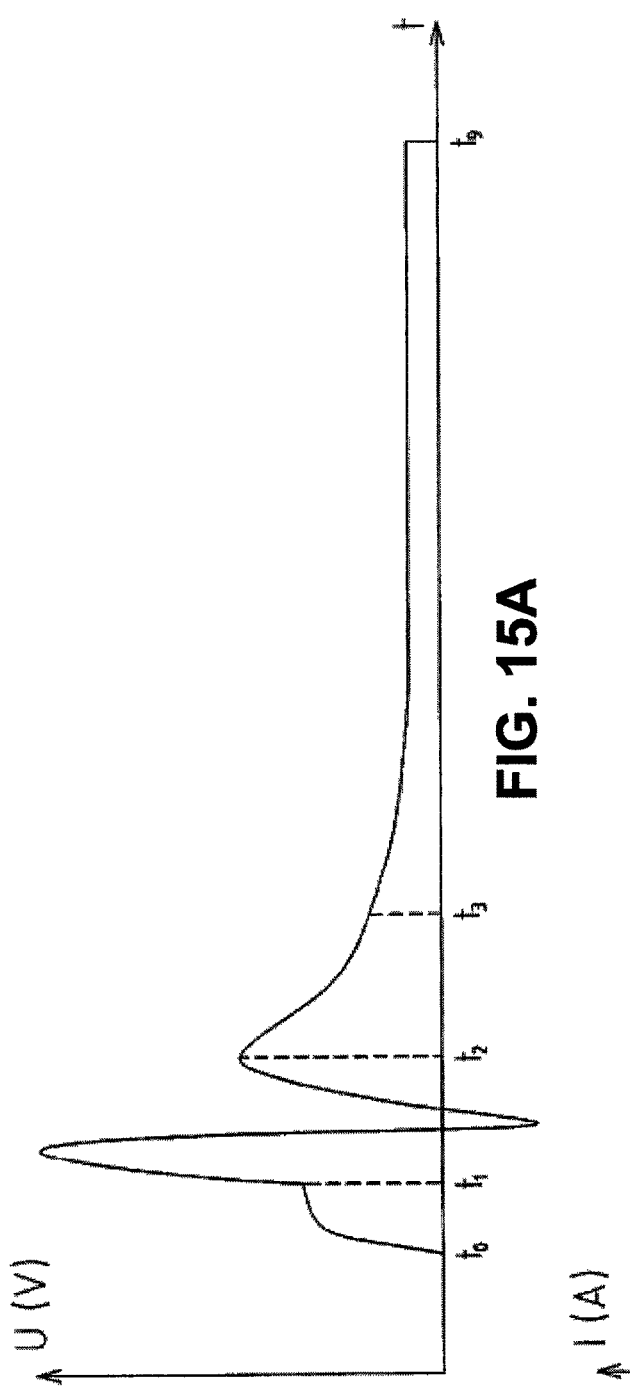
Figure 15C:
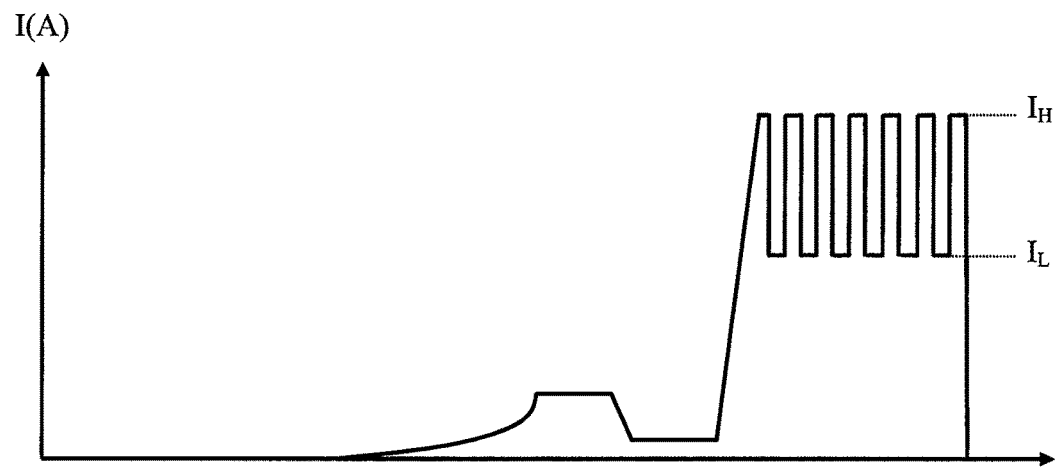
Figure 16:
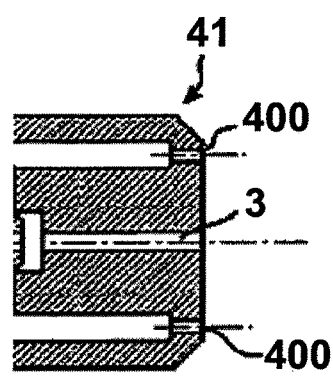
Figure 17A:
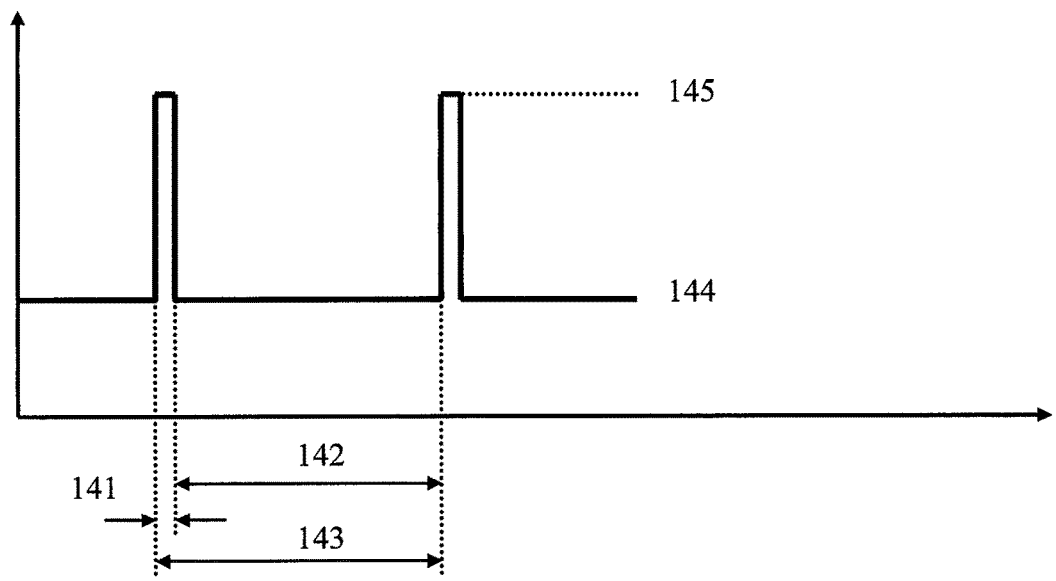
Figure 17B:
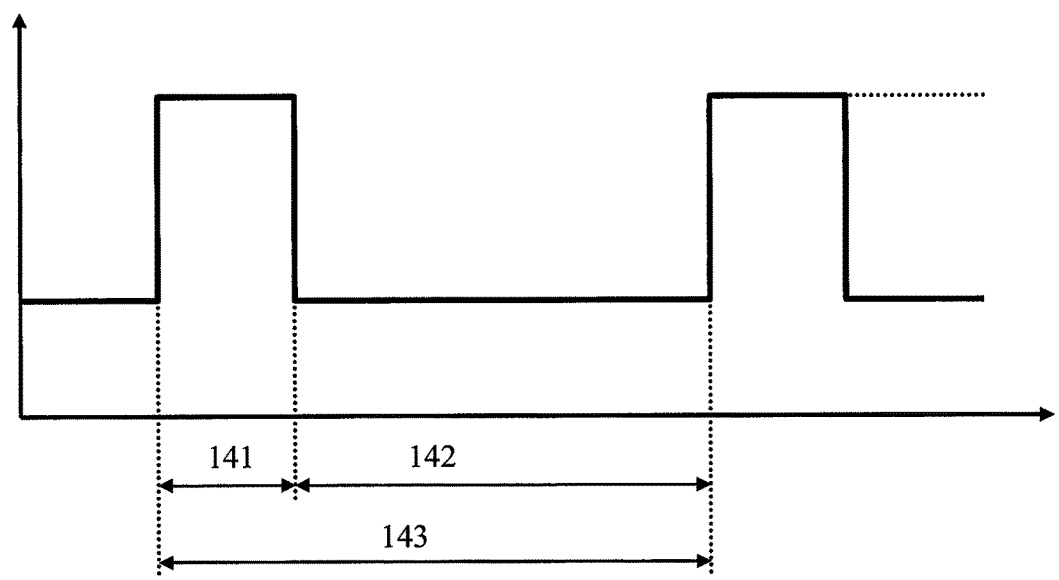
Figure 17C:
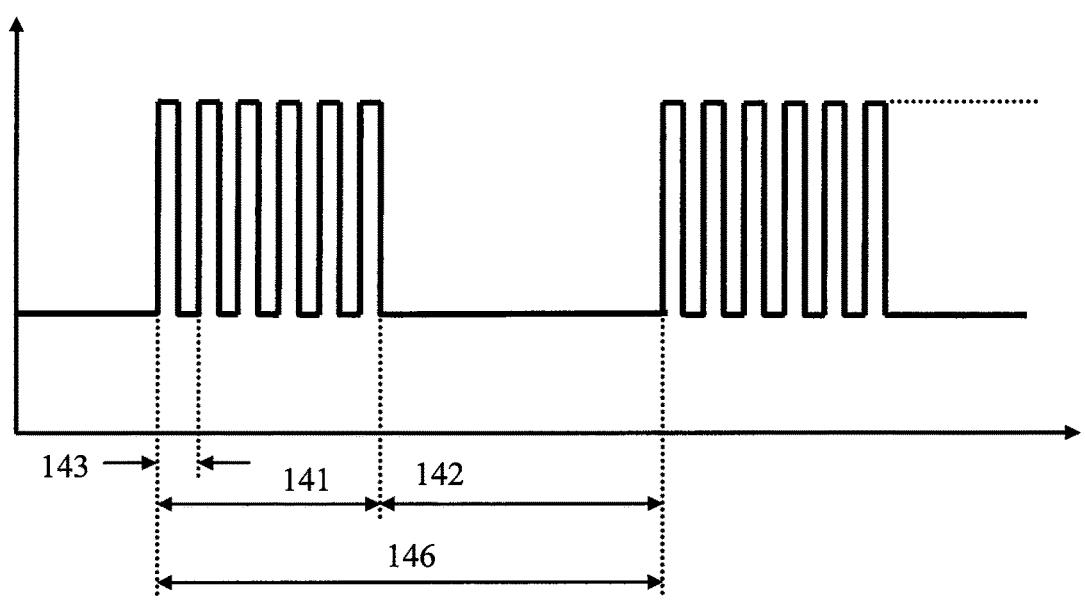
Figure 19A:
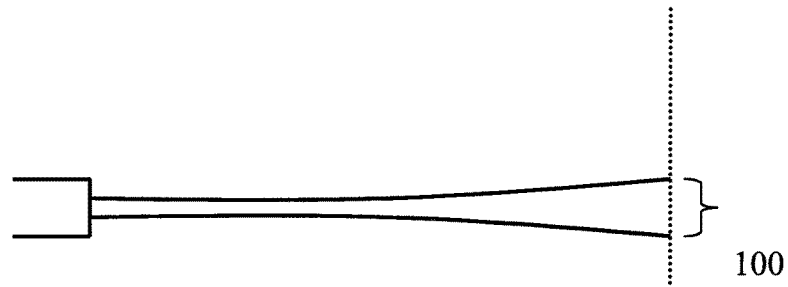
Figure 19B:
Figure 19C:
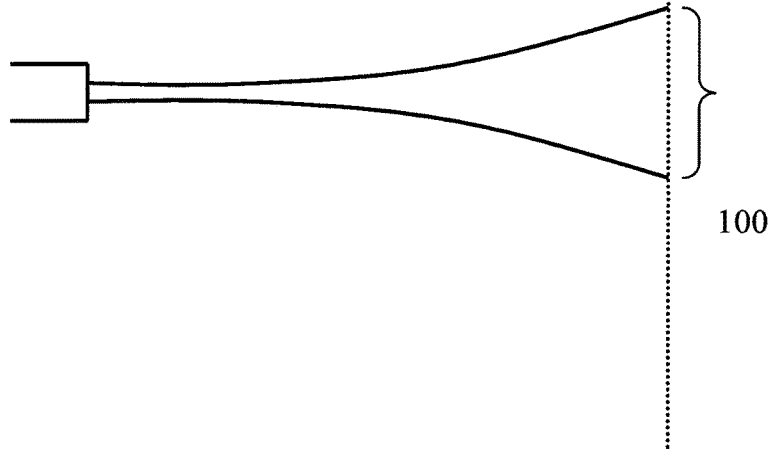
Figure 20A:
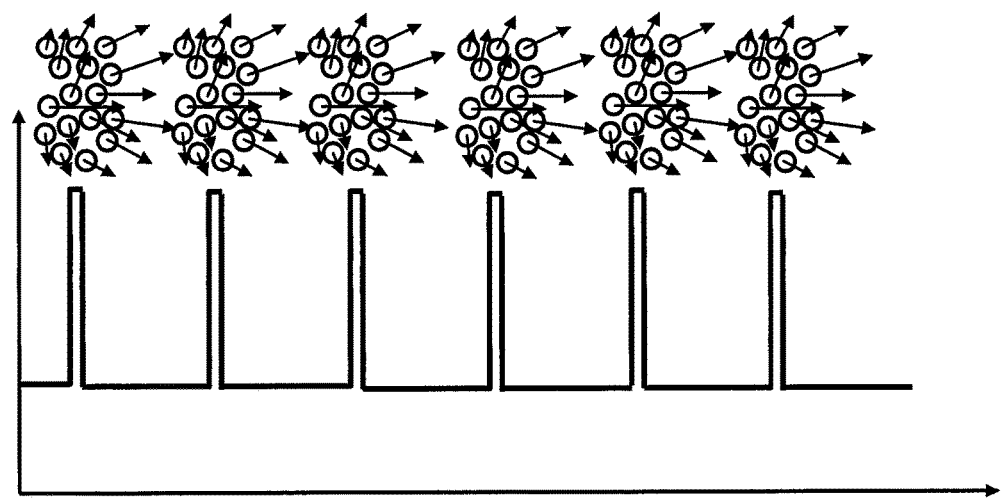
Figure 20B:
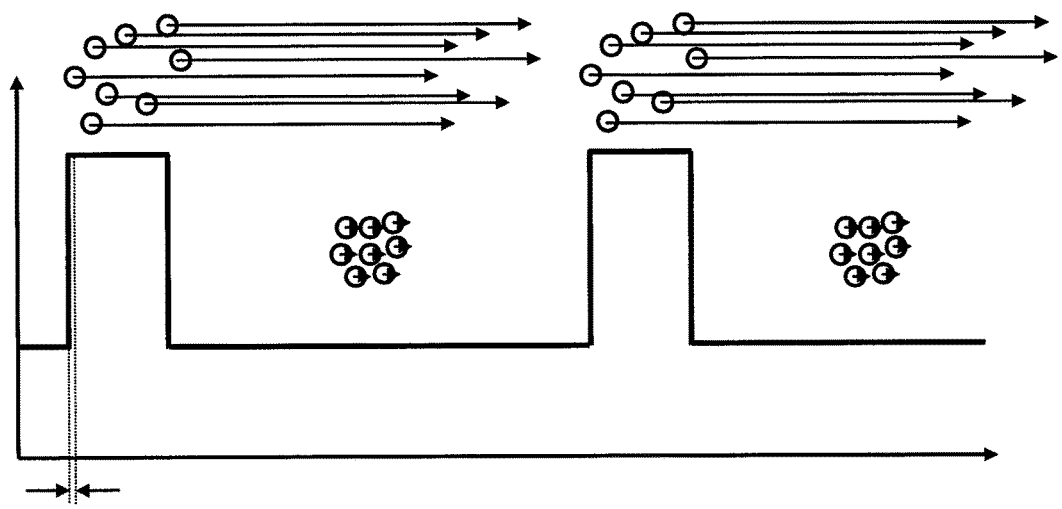
Figure 21A:
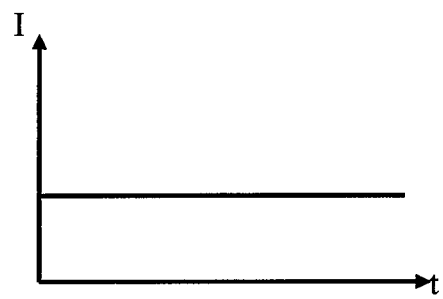
Figure 21D:
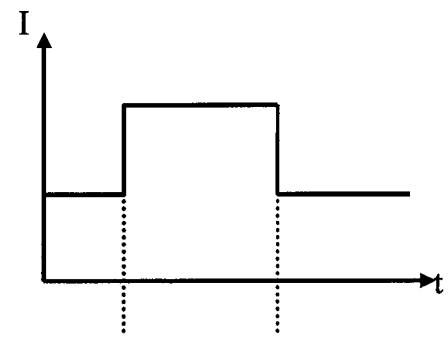
Figure 21B:
Figure 21E:
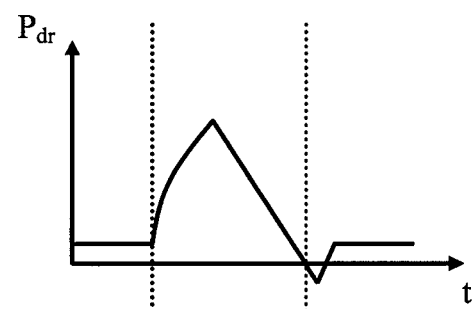
Figure 21C:
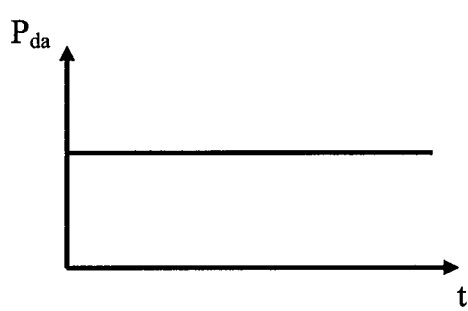
Figure 21F:
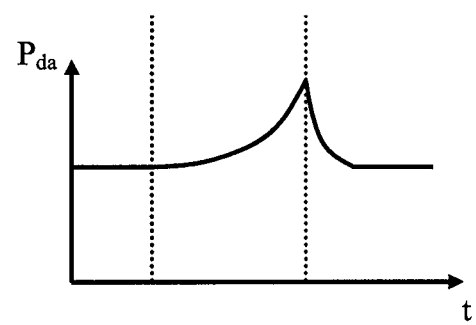
Figure 23:
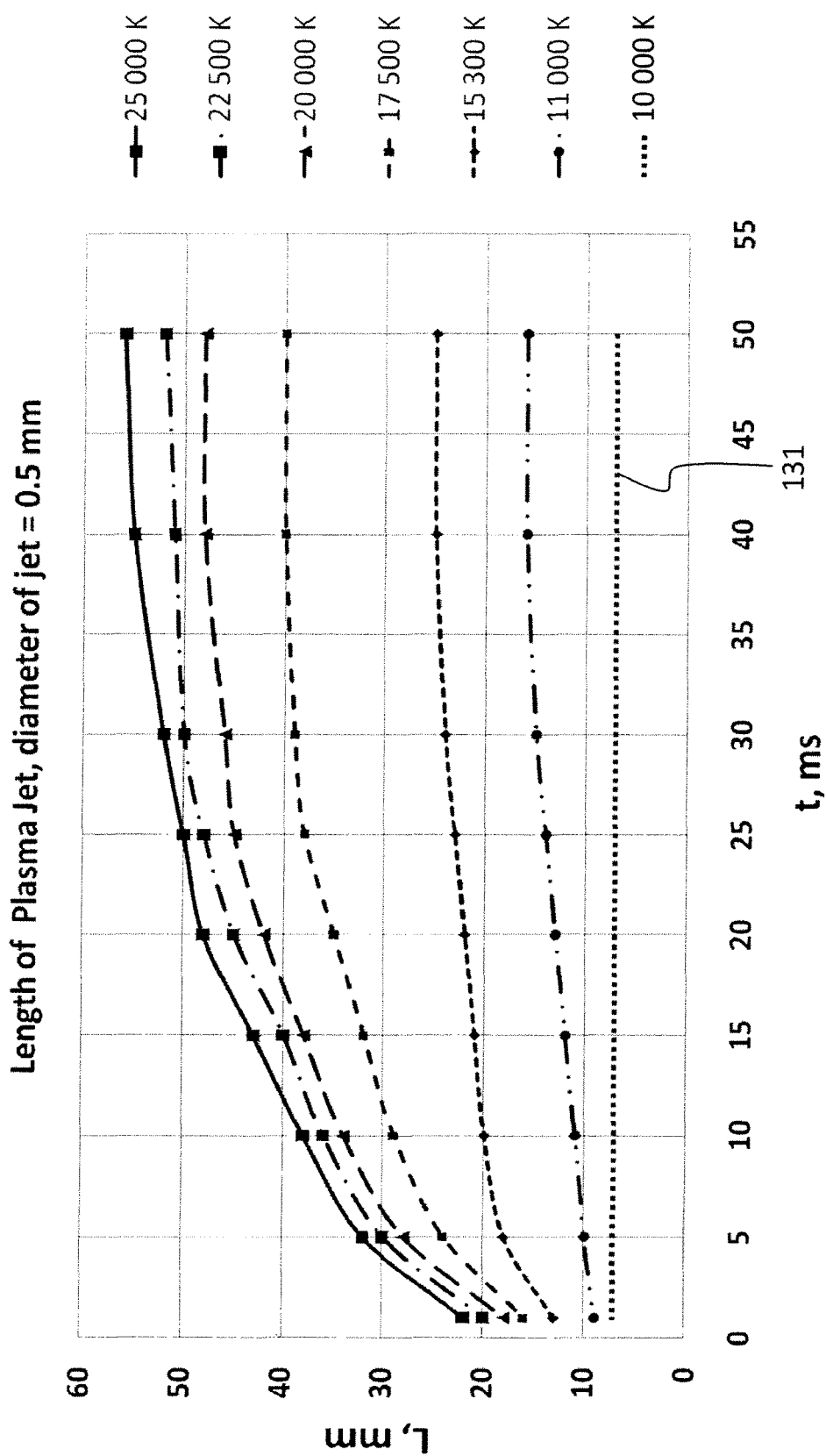
Figure 26A:
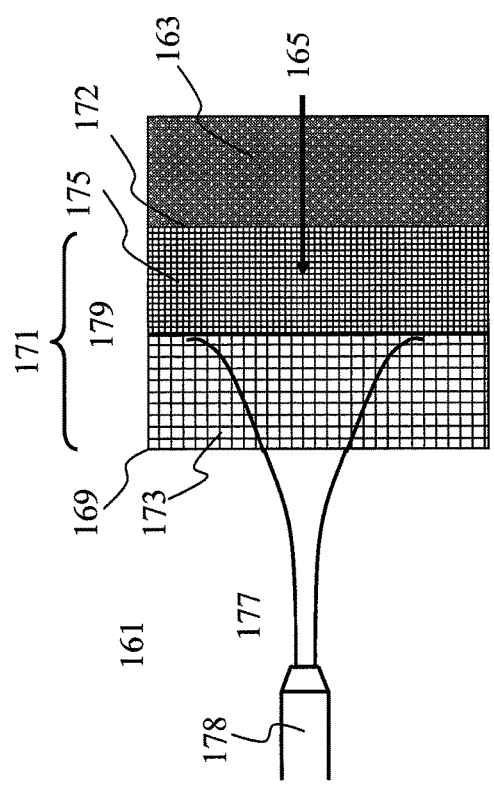
Figure 26B:
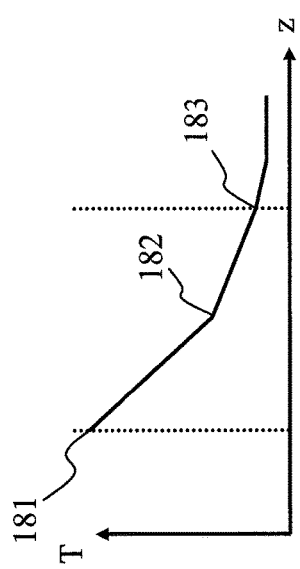
Figure 27A:
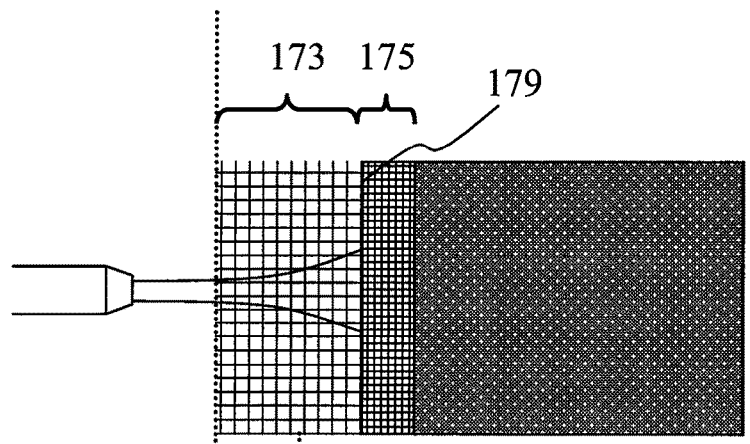
Figure 27B:
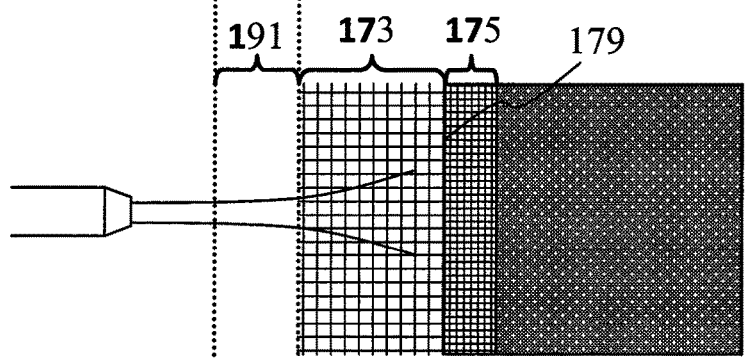
Figure 27C:
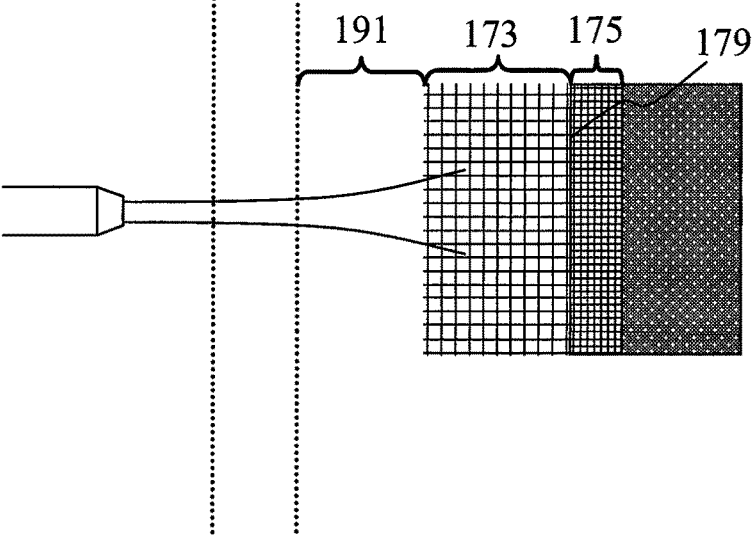
Figure 28:
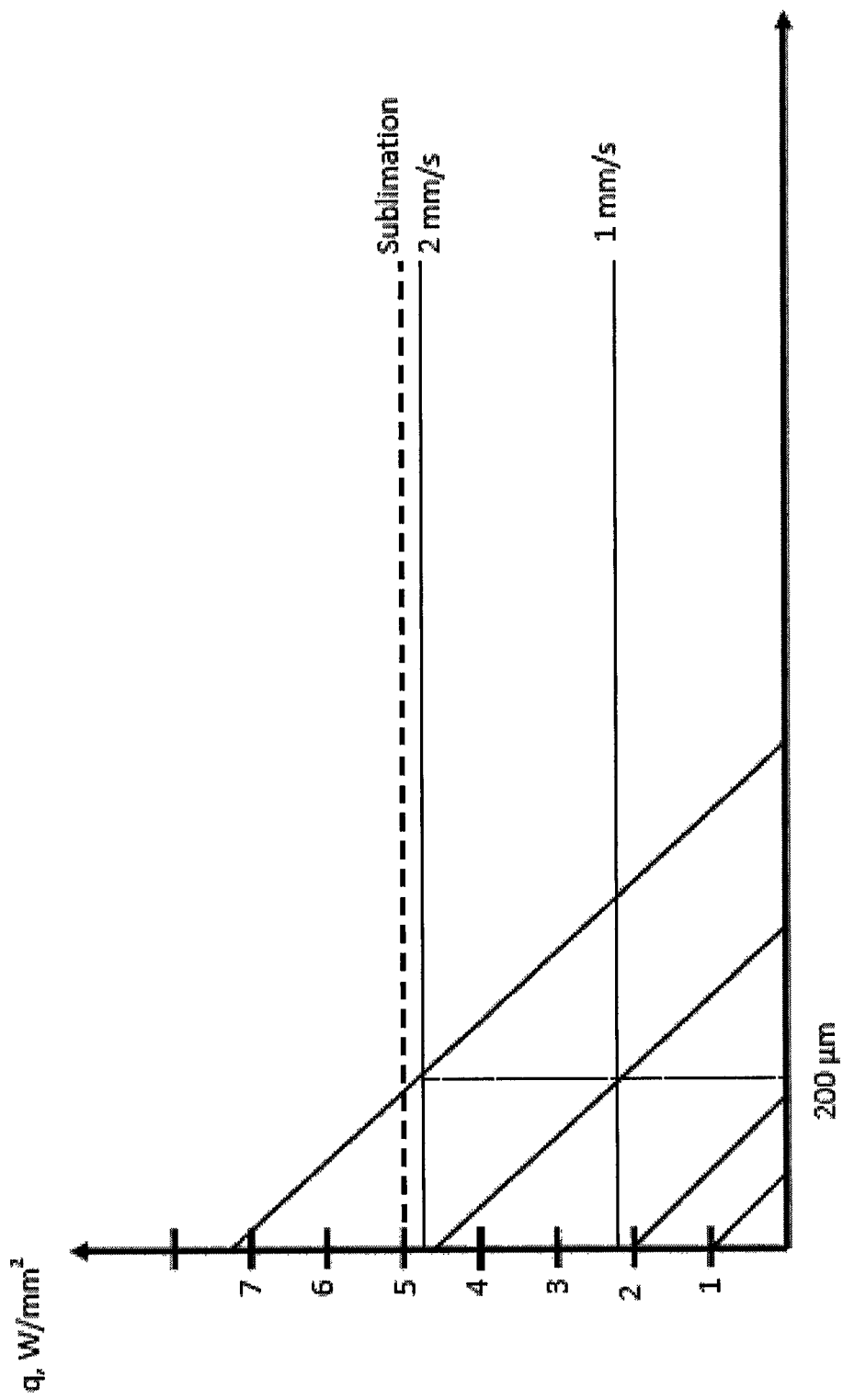
Figure 29A:
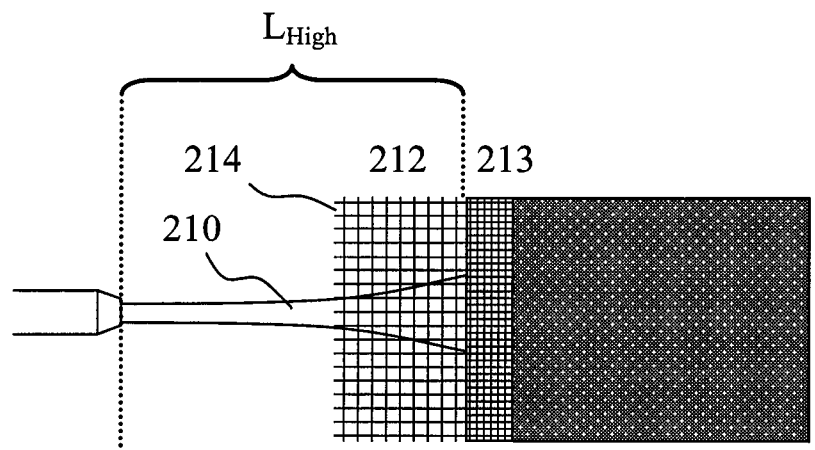
Figure 29B:
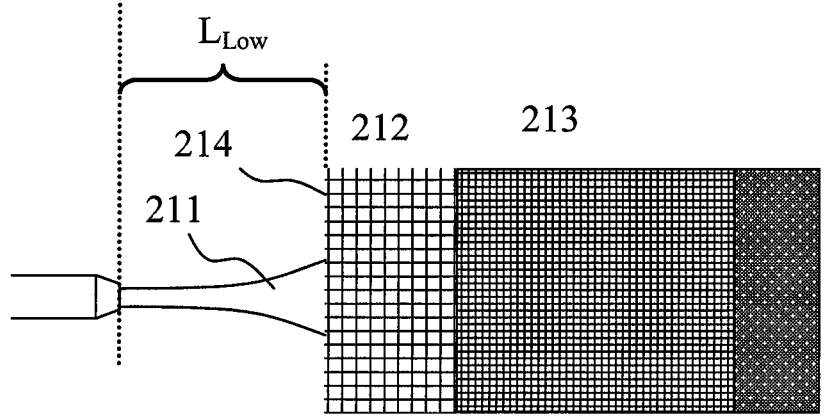
Figure 31A:
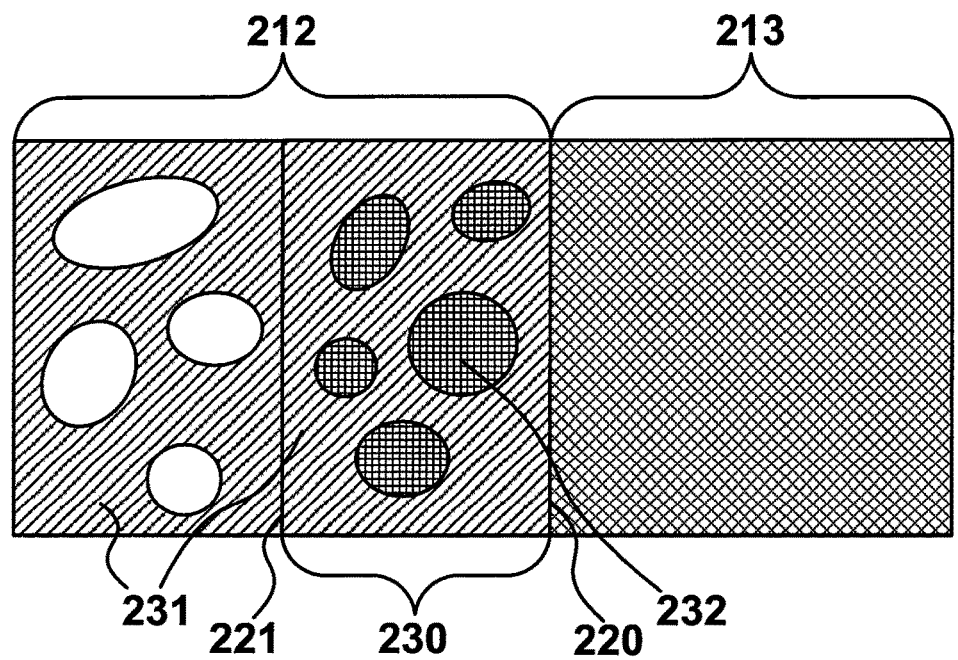
Figure 31B:
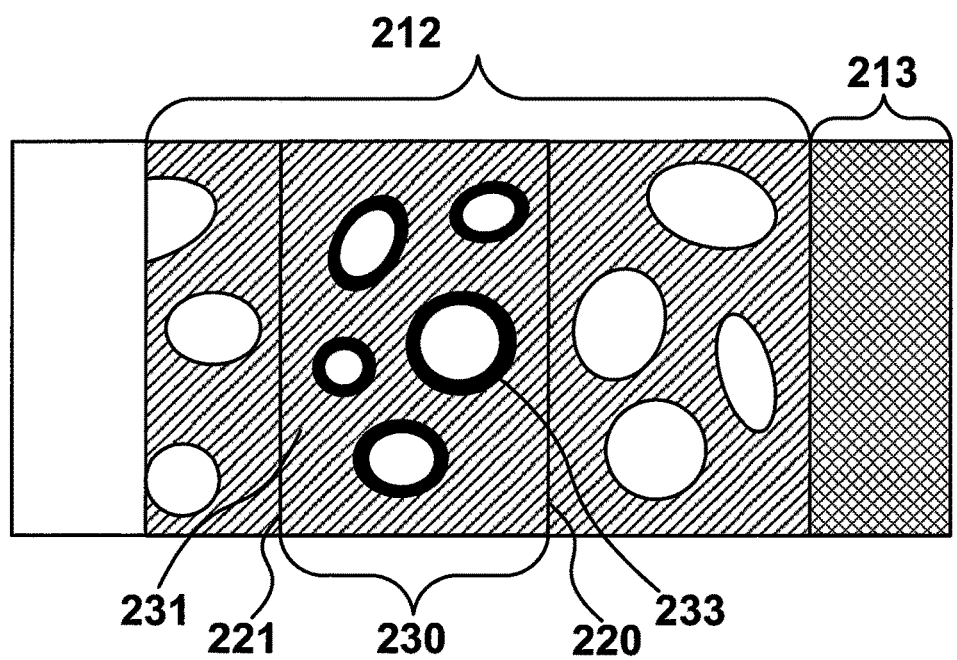
Figure 32:
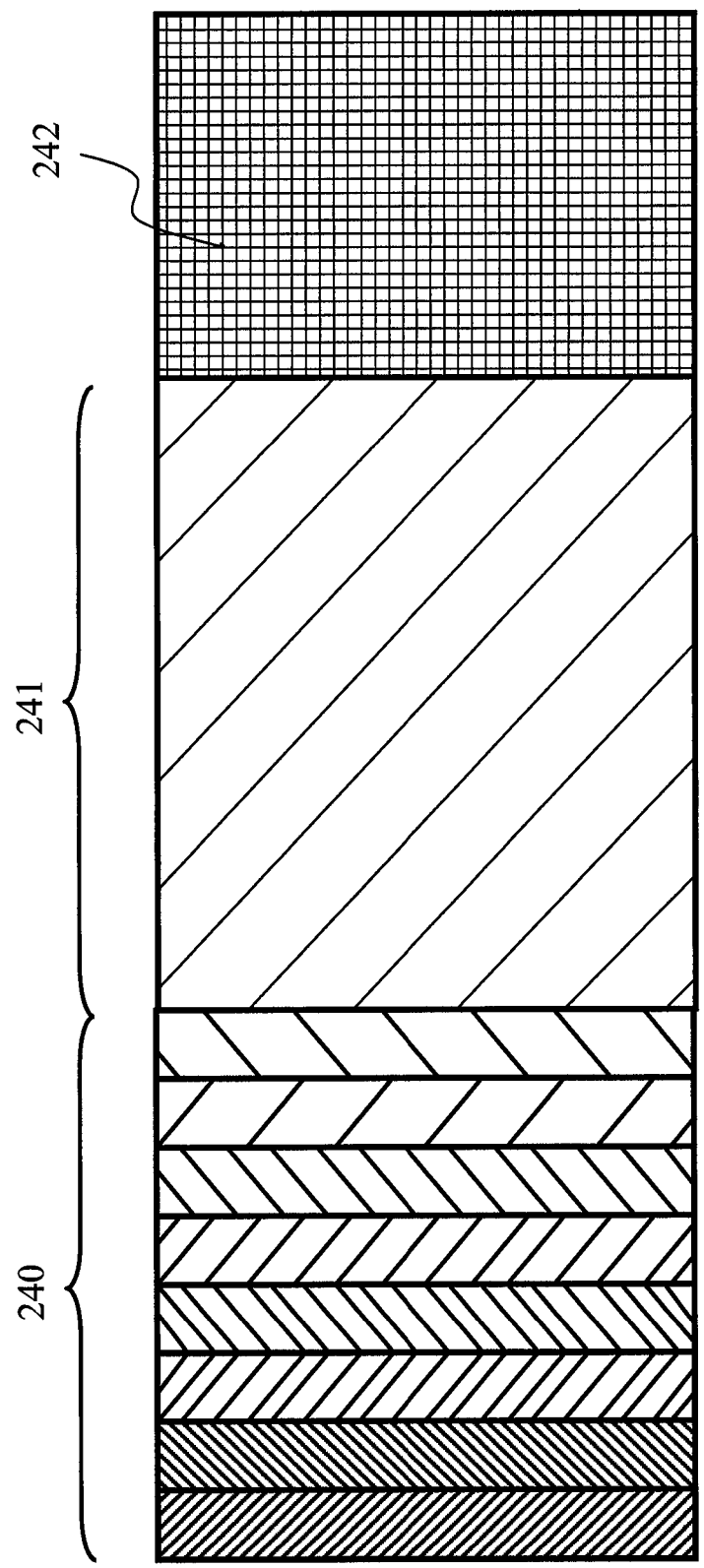
Figure 33B:
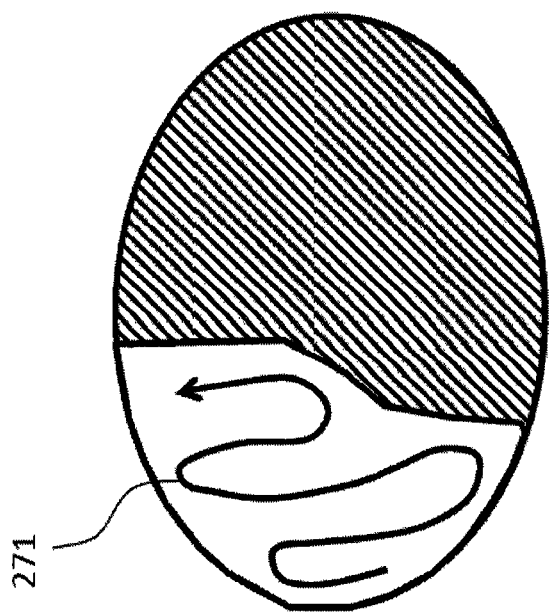
Figure 33A:
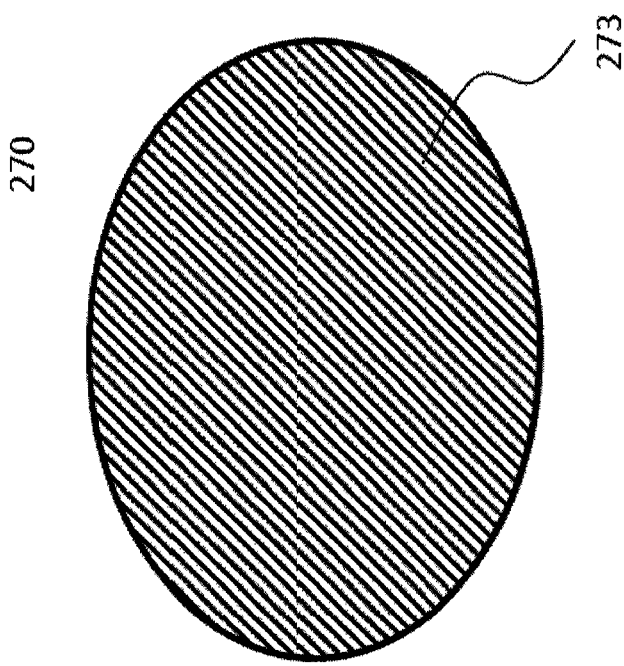
Figure 34A:
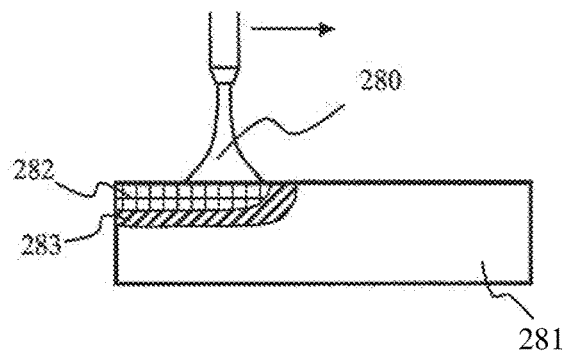
Figure 34B:
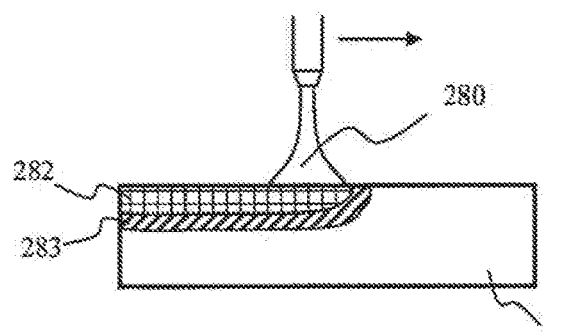
Figure 34C:
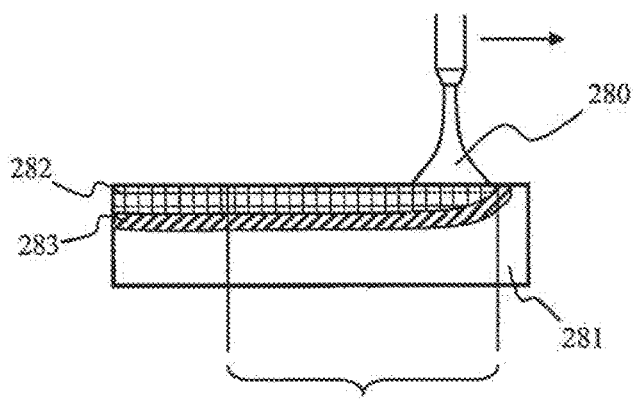
Figure 35:
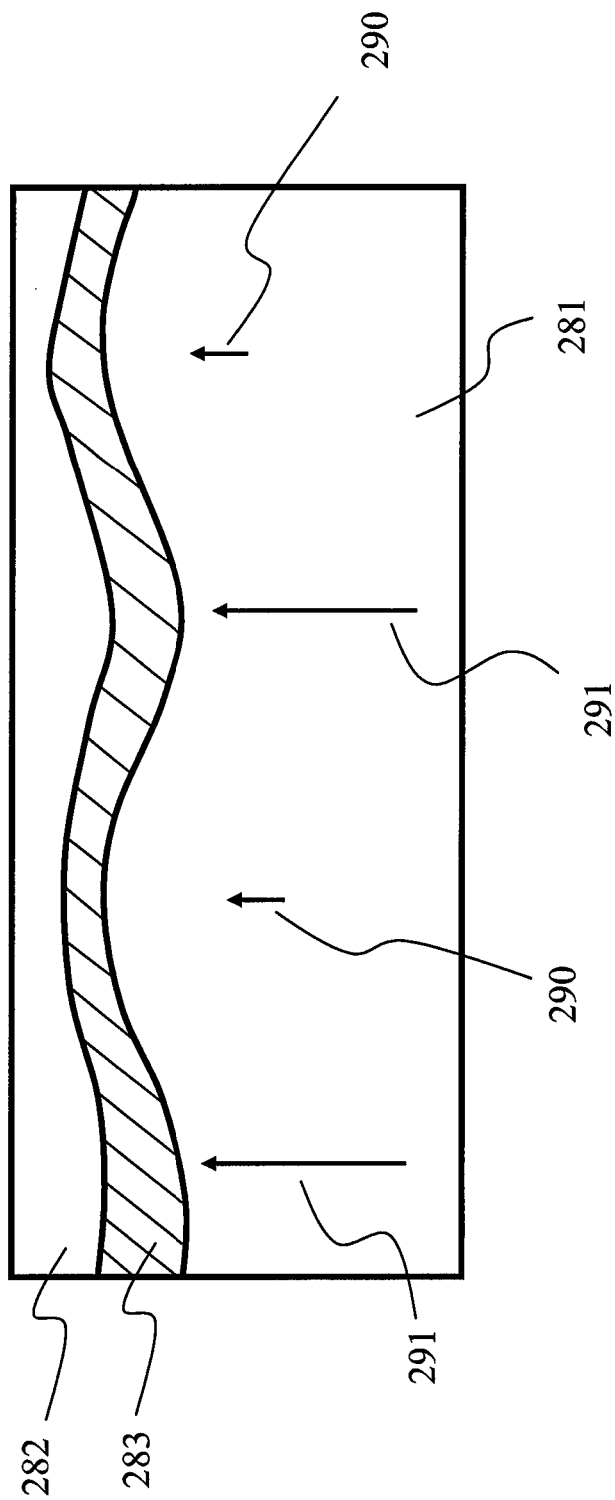
Figure 36:
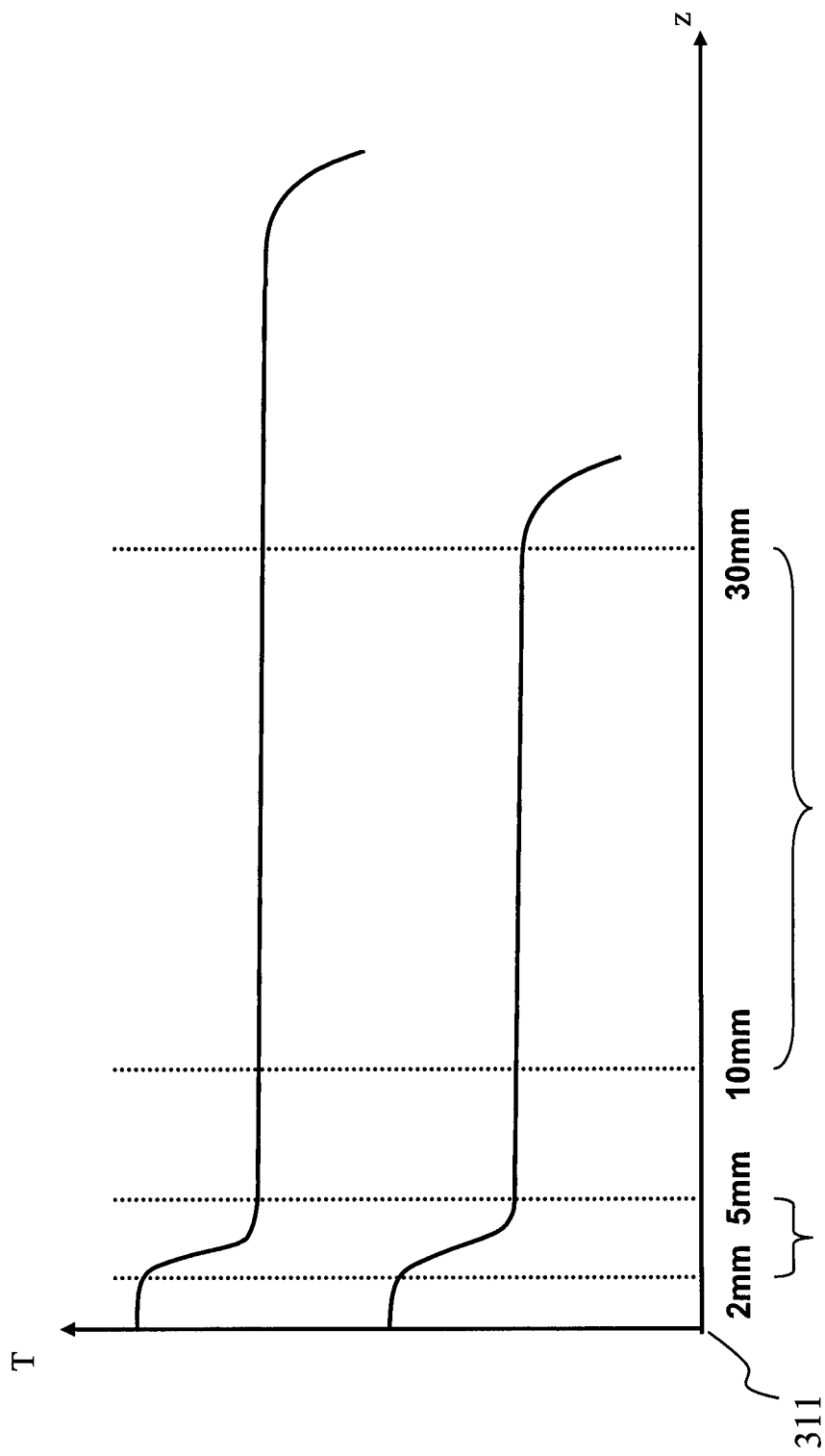
Figure 37:
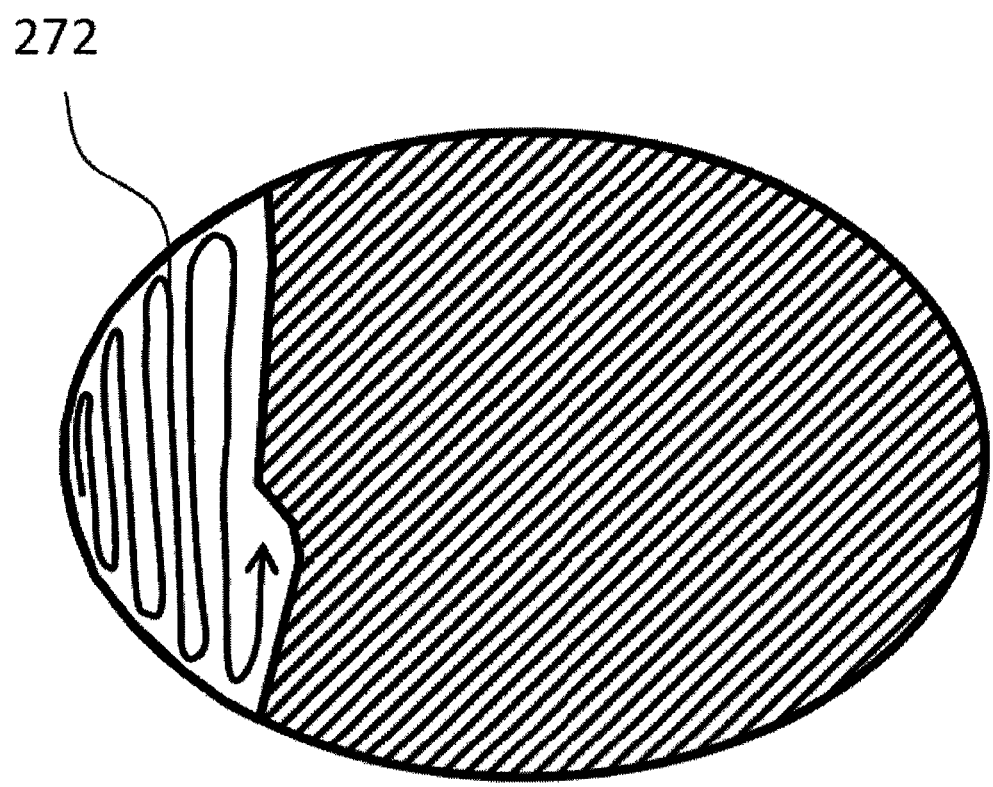
Figure 38:
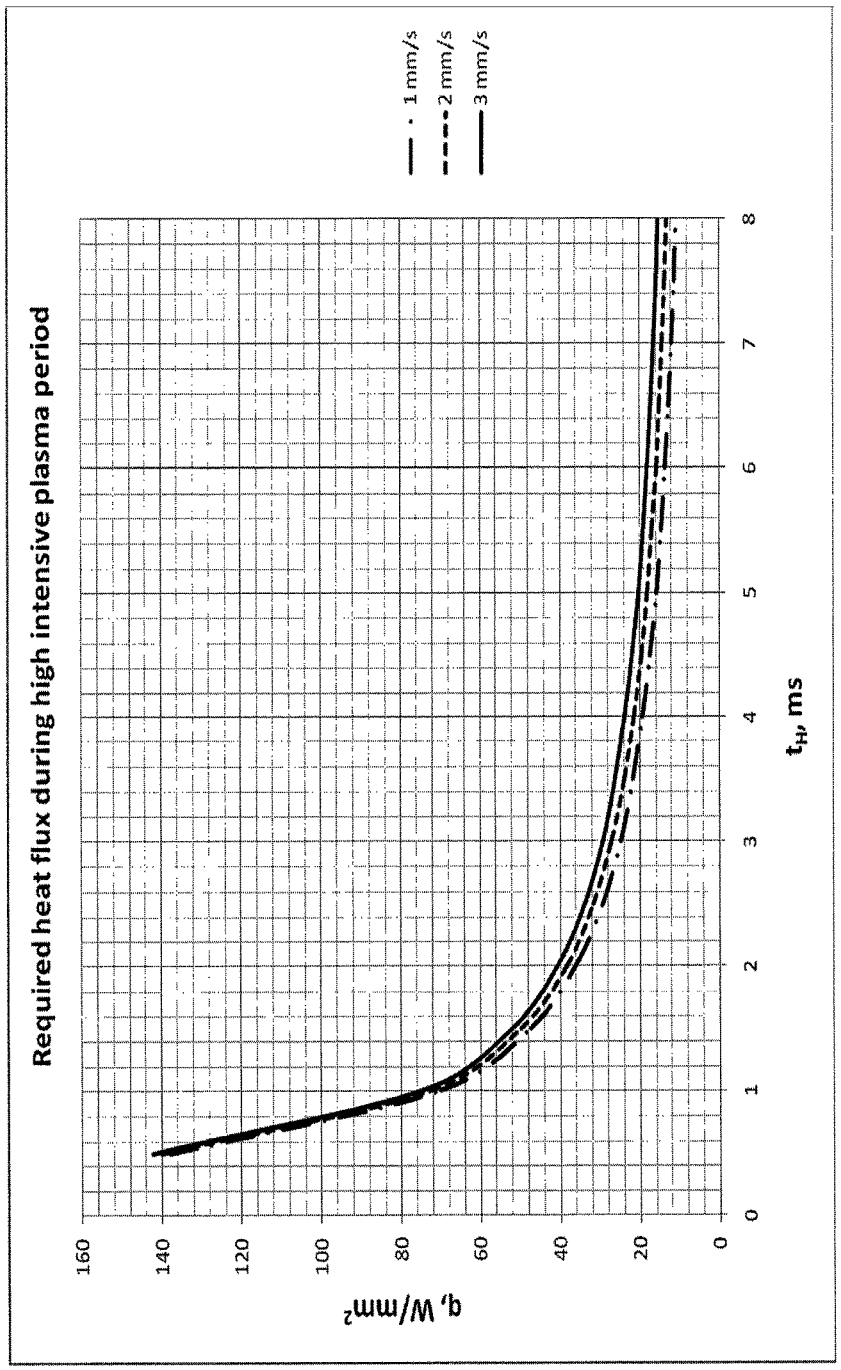
Figure 39:
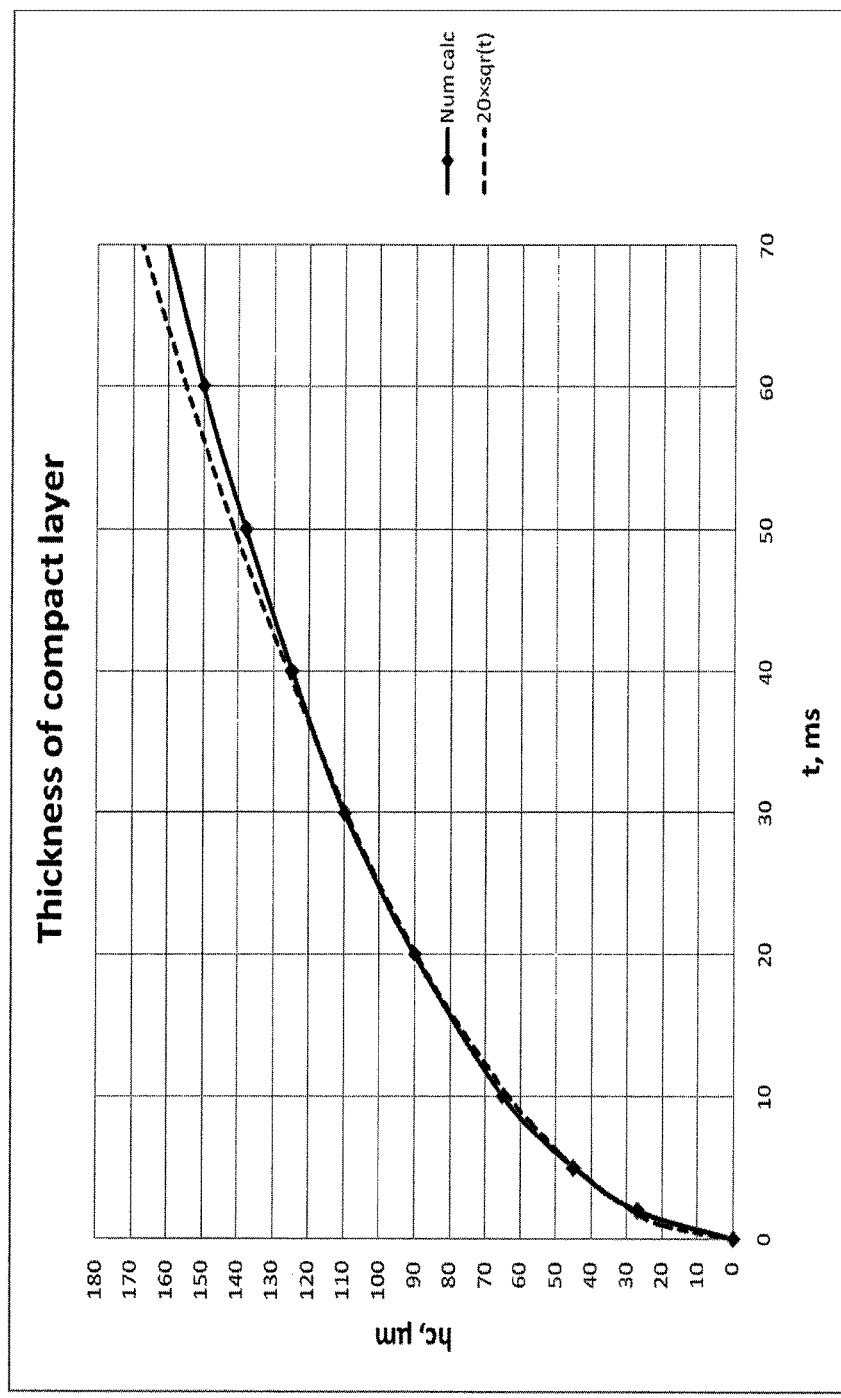
Figure 40:
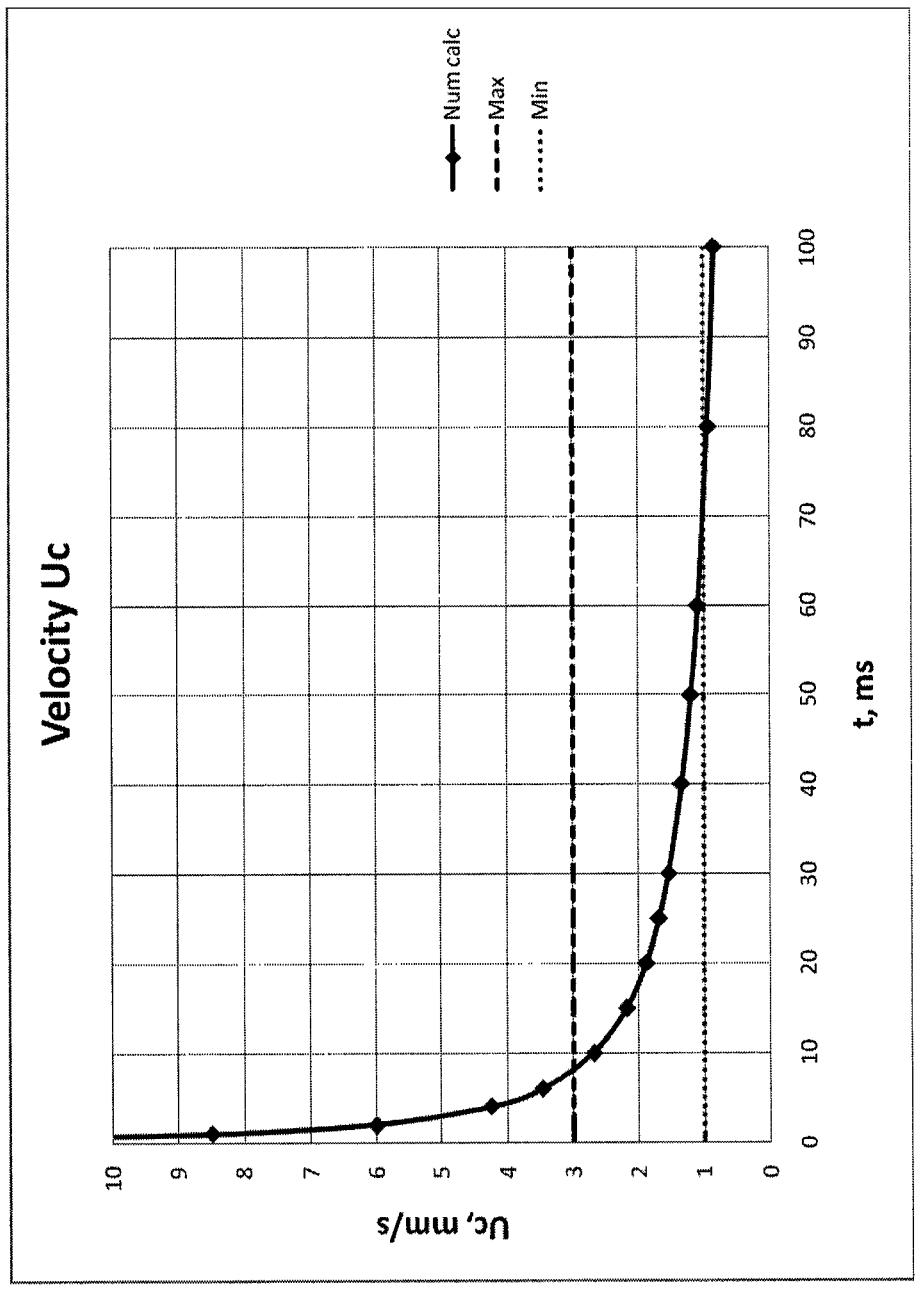
Figure 41:
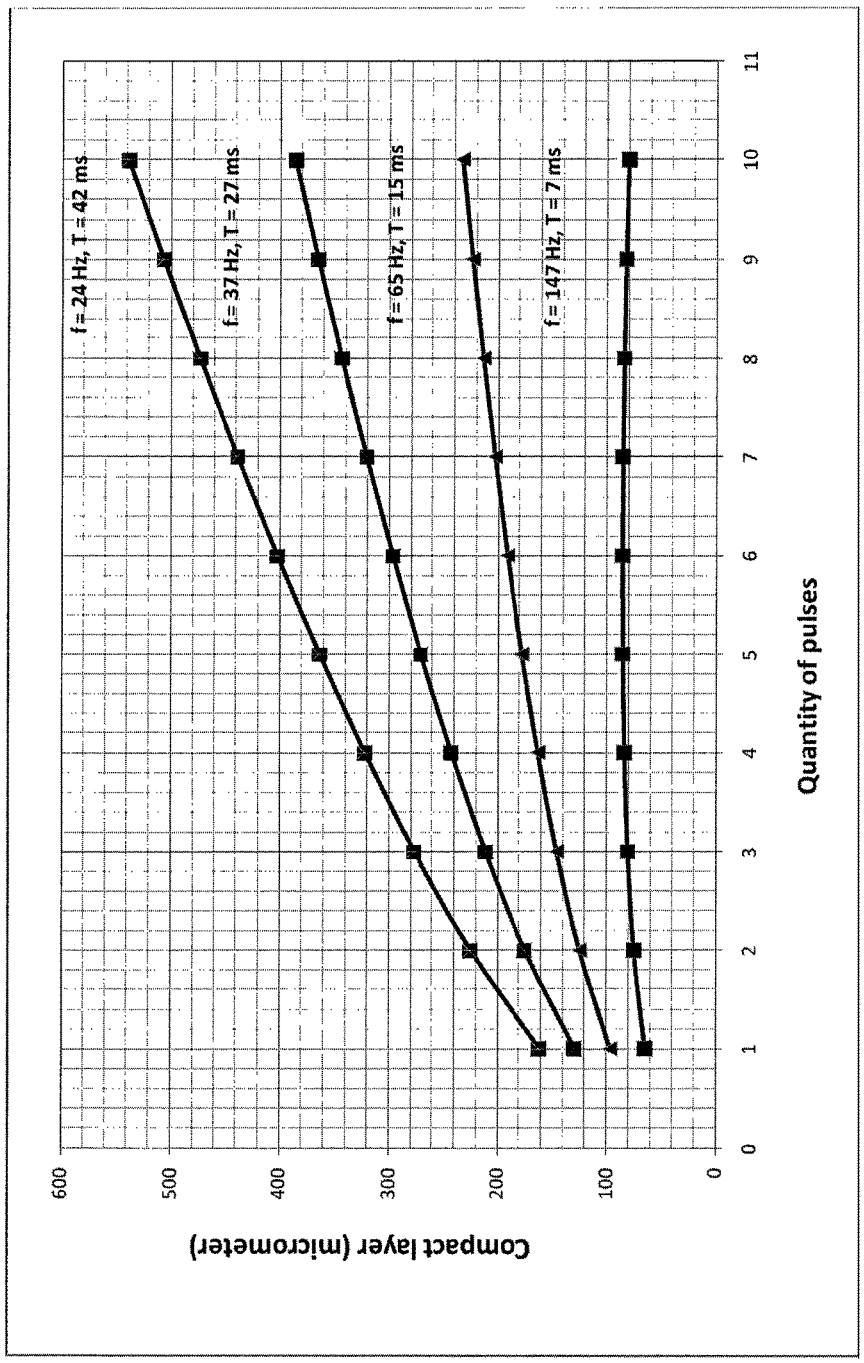
Figure 42:
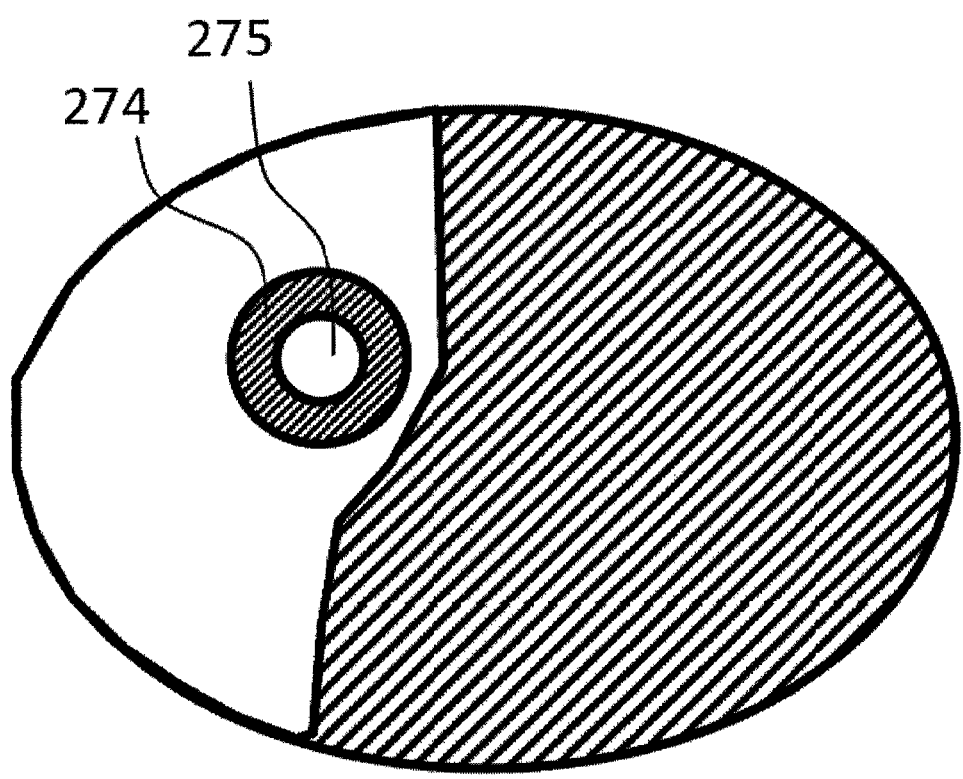
Figure 44:
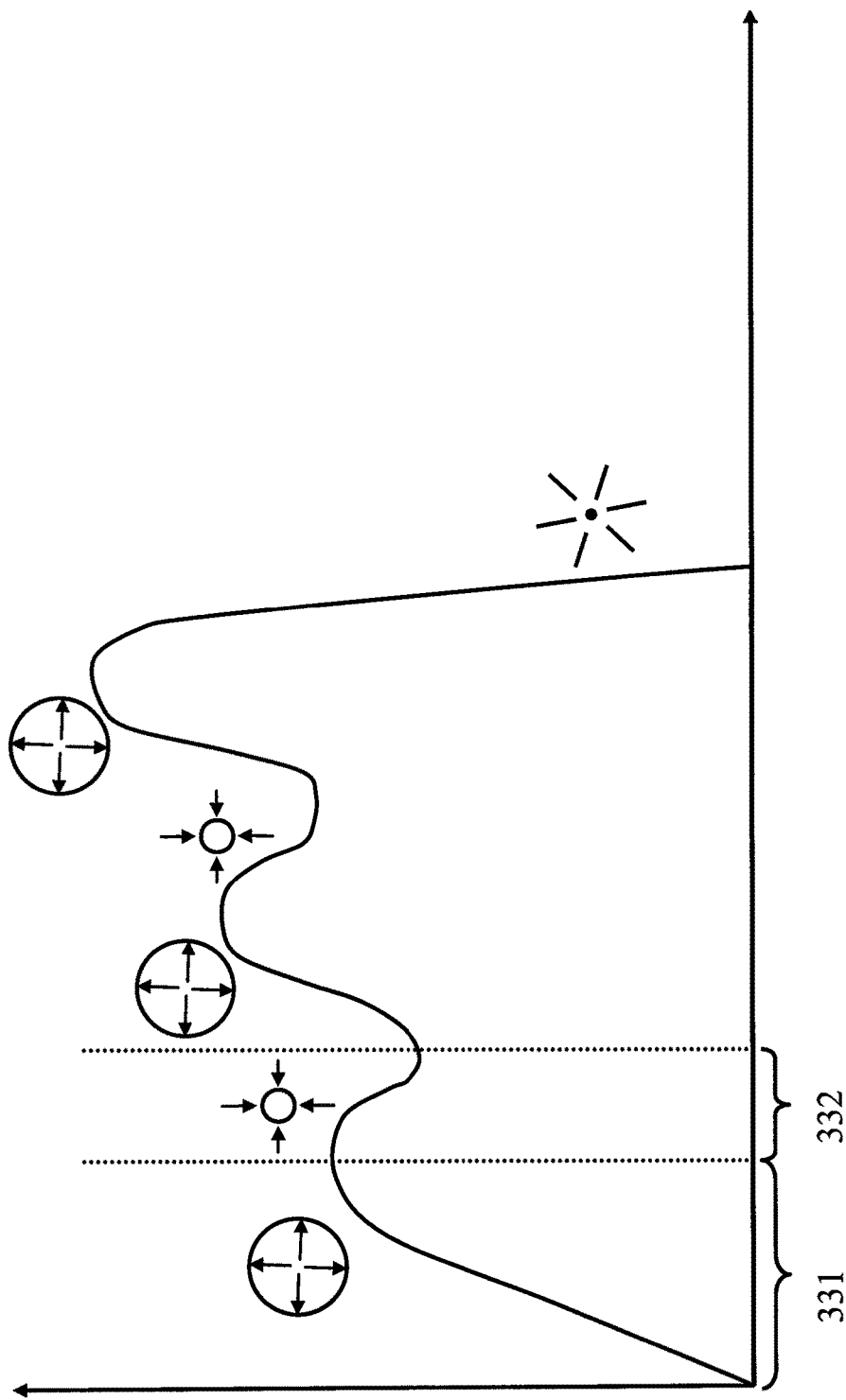
Figure 45C:
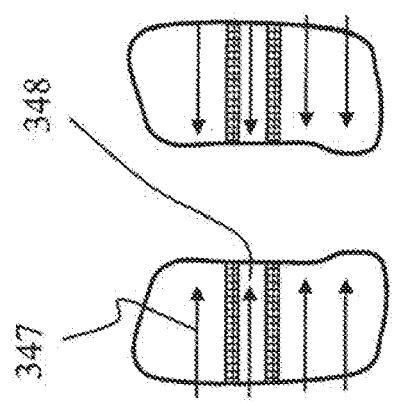
Figure 45B:
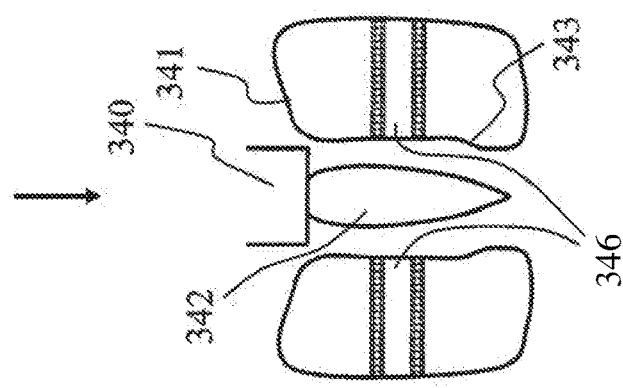
Figure 45A:
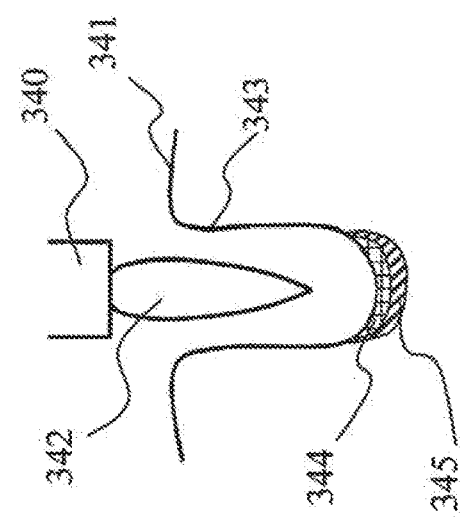
Figure 47:
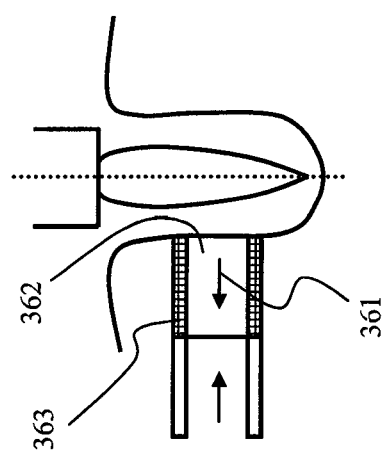
Figure 49B:
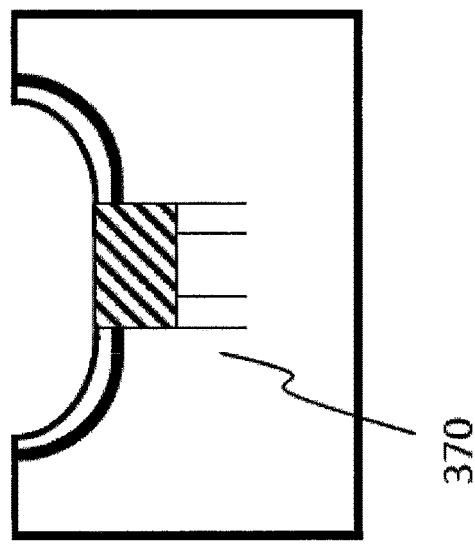
Figure 49A:
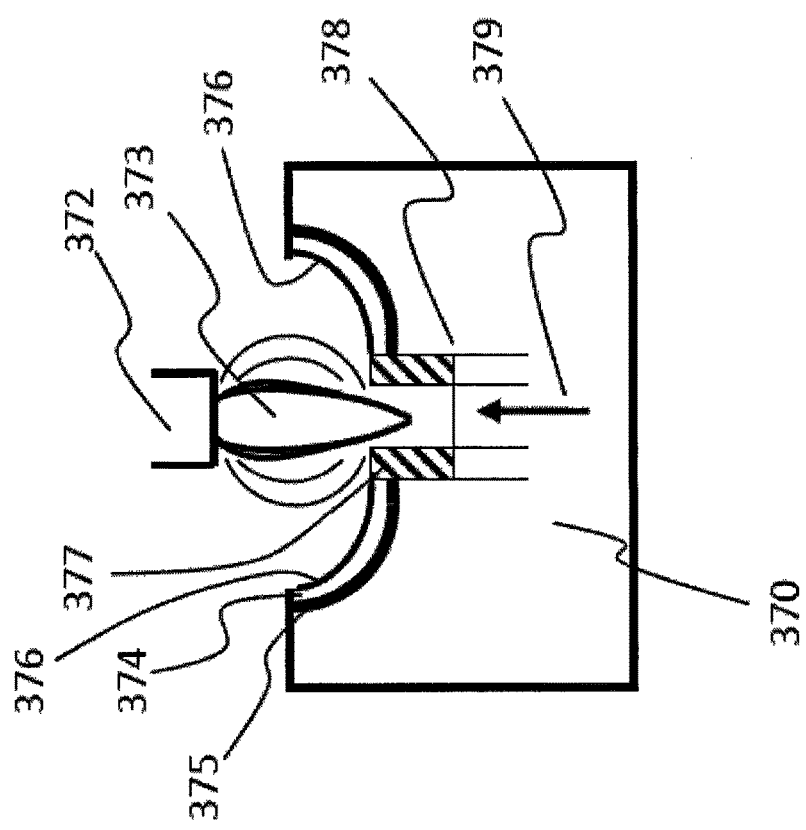
Figure 50:
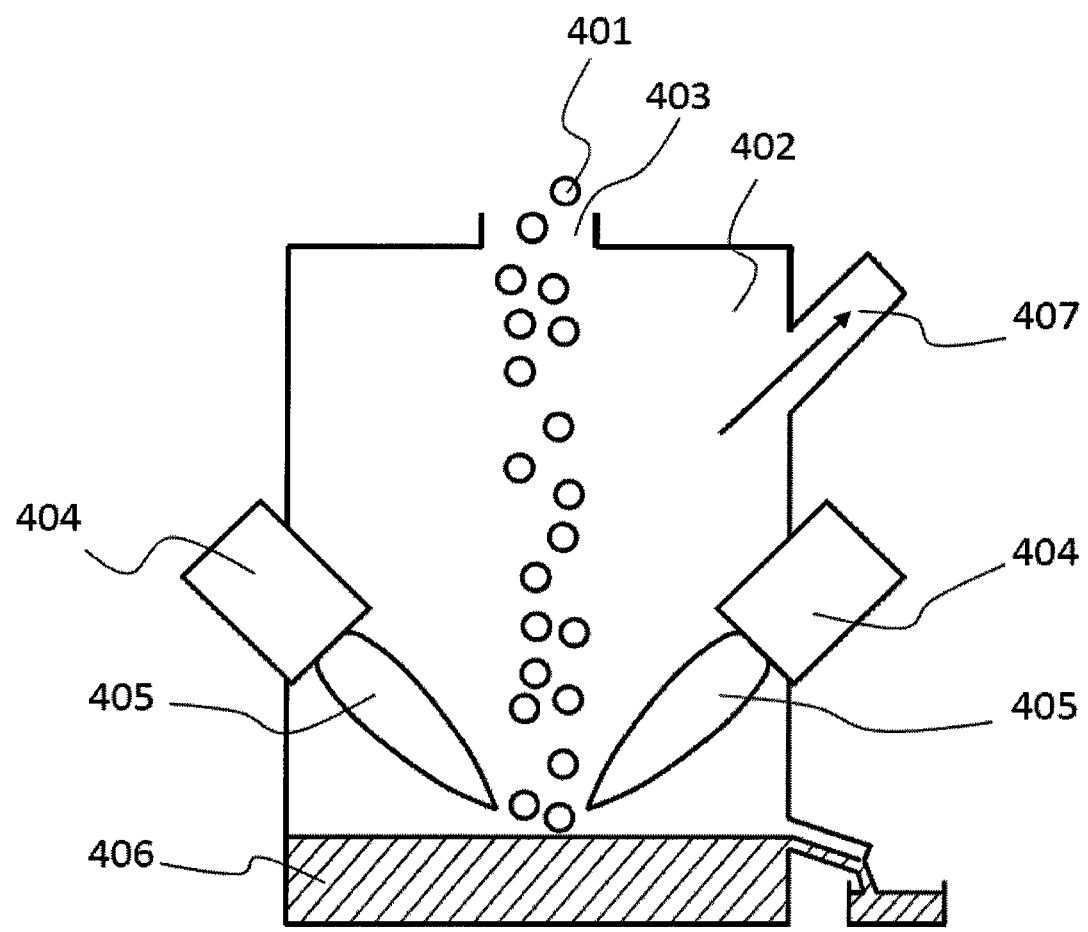

FIGS. 4B-G illustrate the characteristic behavior of plasma particles at different stages of a volumetric oscillation;

FIG. 5 illustrates a volumetrically oscillating plasma flow;

FIG. 6 illustrates an embodiment of a system capable of providing volumetrically oscillating plasma flows;

FIG. 7 illustrates a longitudinal cross-section of a multi-electrode plasma-generating device;

FIG. 8 illustrates a longitudinal cross-section of an alternative embodiment of a multi-electrode plasma-generating device having a plasma channel comprising an expansion portion;

FIG. 9 illustrates an arbitrary periodic current wave form for generating a volumetrically oscillating plasma flow;

FIG. 10 shows a power supply using three current sources from produce various current waves for generating volumetrically oscillating plasma flows;

FIG. 11 illustrates a biased pulse current wave;

FIG. 12 illustrates an exemplary modulated biased pulse wave;

FIG. 13A-B illustrate various current waveforms used to generate volumetrically oscillating plasma flows;

FIG. 14A illustrates a longitudinal cross-section of an alternative embodiment of a plasma-generating device specifically adapted for generation of volumetrically oscillating intermittent plasma flows;

FIG. 14B illustrates a specialized multi-cathode assembly for use in the device shown in FIG. 14A;

FIG. 15A illustrates single period of a voltage wave that can be applied between the cathode and the anode to generate an intermittent plasma flow;

FIG. 15B illustrates a single period of a current wave that can be passed through the cathode and the anode to generate an intermittent plasma flow;

FIG. 15C illustrates a single period of a current wave that can be passed through the cathode and the anode to generate intermittent volumetrically-oscillating plasma flow;

FIG. 16 illustrates an alternative embodiment of a multi-electrode plasma-generating device comprising pass-through cooling channels;

FIG. 17A illustrates a high frequency biased pulse current wave;

FIG. 17B illustrates a low frequency biased pulse current wave;

FIG. 17C illustrates a modulated biased pulse current wave;

FIG. 18A illustrates active plasma during a low intensity interval of a volumetrically oscillating plasma flow;

FIG. 18B illustrates active plasma during a high intensity interval of a high frequency volumetrically oscillating plasma flow;

FIG. 18C illustrates active plasma during a high intensity interval of a low frequency volumetrically oscillating plasma flow;

FIGS. 19A-C illustrate the differences in volume between a continuous plasma flow and the high intensity plasma of volumetrically oscillating plasma flows with low and high frequency;

FIG. 20A illustrates a volumetrically oscillating plasma flow with a relatively short high intensity interval;

FIG. 20B illustrates a volumetrically oscillating plasma flow with a relatively long high intensity interval;

FIGS. 21A-C are graphs showing the current and dynamic pressure components for a continuous plasma flow;

FIGS. 21D-F are graphs showing the current and dynamic pressure components for an axially oscillating plasma flow;

FIGS. 22A-D illustrate the effect of the radial component of the dynamic pressure on the width of an axially oscillating plasma flow;

FIG. 23 is a graph of the length of the high intensity plasma flow as a function of the period of oscillation;

FIG. 24 illustrates a surgical site created by the dissection of tissue during surgery;

FIG. 25 illustrates a surgical site in which the blood flow has been stopped by forming a sealing layer covering the underlying tissue;

FIG. 26A Illustrates a continuous plasma flow forming a sealing layer;

FIG. 26B is a graph of the heat flux as a function of distance from the tissue surface;

FIGS. 27A-C illustrates a rapid sublimation of tissue during coagulation with a continuous plasma flow having a relatively high heat flux;

FIG. 28 is a graph illustrating the heat flux as a function of distance from the tissue surface for plasma flows of various intensities;

FIG. 29A-B illustrates the application of a single oscillation of a volumetrically oscillating plasma flow to a tissue;

FIGS. 30A-F illustrate coagulation with an axially oscillating plasma flow over three oscillations;

FIG. 31A illustrates the surface region of a tissue at the end of the low intensity interval of a plasma flow oscillation;

FIG. 31B illustrates the surface region of a tissue after the high intensity interval of a plasma flow oscillation;

FIG. 32 illustrates a completed sealing layer formed by an axially oscillating plasma flow;

FIG. 33A illustrates a surgical site covered with blood;

FIG. 33B illustrates an operator sweeping a volumetrically oscillating plasma flow over a surgical site;

FIG. 34A-C illustrate the effect of a volumetrically oscillating plasma flow as it sweeps across a surgical site;

FIG. 35 illustrates a variable thickness sealing layer;

FIG. 36 is a graph of the temperature of a volumetrically oscillating plasma flow along the plasma flow axis during both the high intensity interval and the low intensity interval;

FIG. 37 illustrates an operator sweeping a continuous plasma flow over a surgical site;

FIG. 38 is a graph of the vaporization heat flux plotted for three different bleeding rates as a function of the high intensity interval;

FIG. 39 is a graph of the short time approximation and the numerical simulation of compact layer formation as a function of the low intensity interval;

FIG. 40 is a graph of the rate of compact layer formation as a function of the low intensity interval plotted based on experimental data;

FIG. 41 is a graph of the compact layer thickness as a function of the number of oscillations for several different frequencies;

FIG. 42 illustrates a partially coagulated surgical site with an exposed blood vessel;

FIGS. 43A-C illustrates the application of axially oscillating plasma to seal a blood vessel;

FIG. 44 is a graph of the radius of a bubble as a function of time under the influence of ultrasonic cavitation;

FIGS. 45A-C illustrate the process of cutting with a typical prior art continuous plasma flow;

FIGS. 46A-C illustrate the process of cutting with a radially oscillating plasma flow;

FIG. 47 illustrates the radial component of a radially oscillating plasma flow sealing a blood vessel;

FIGS. 48A-E illustrate the vaporization of a tumor with a volumetrically oscillating plasma flow;

FIG. 49A-B illustrate a volumetrically oscillating plasma flow sealing a blood vessel exposed during vaporization;

FIG. 50 illustrates a volumetrically oscillating plasma waste disposal system.

5 DETAILED DESCRIPTION OF THE EMBODIMENTS

5.1 Introduction to Volumetrically Oscillating Plasma

Figure 1A:
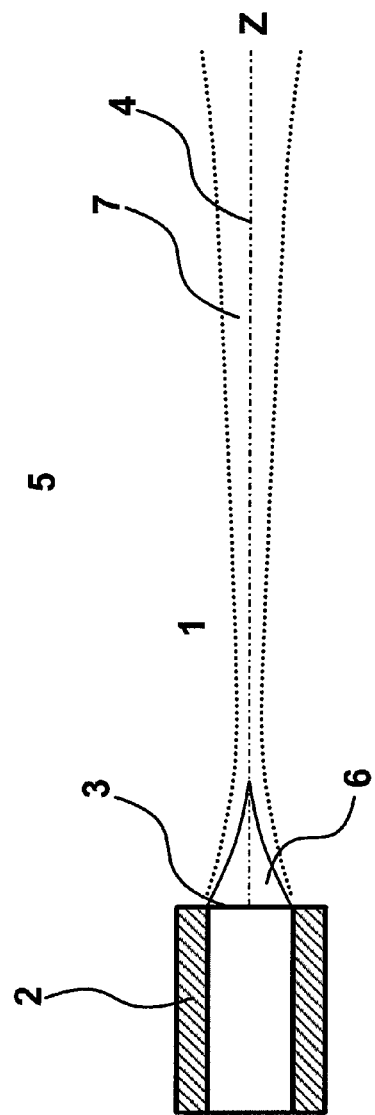
FIG. 1A illustrates the structure of a typical plasma flow generated with a plasma-generating device.

By way of introduction, a plasma flow is a stream of gas particles in which a non-negligible number of the gas particles are ionized. One common way of generating a plasma flow is to heat a stream of gas, referred to as the plasma-generating gas, to a high enough temperature to ionize a portion of the gas particles. FIG. 1A illustrates a longitudinal cross-section of a typical plasma flow generated in this manner. Plasma flow 1 is discharged by a plasma-generating device comprising tip 2 having an outlet 3. Plasma flow 1 propagates away from tip 2 along plasma flow axis 4. Under certain flow conditions, plasma flow 1 remains laminar and does not mix significantly with surrounding medium 5, which is typically air. A laminar flow, such as plasma flow 1, is characterized by a high concentration of energy in the core of the flow, i.e., at, or in close proximity to, axis 4, and a rapid radial temperature drop off. Typically the distribution of energy and temperature in plasma flow 1 transverse to plasma flow axis 4 is substantially parabolic.

A plasma flow with a substantially parabolic temperature distribution transverse to plasma flow axis 4 does not have a single temperature. For many purposes, however, it is useful to characterize the plasma flow with a single representative temperature. One way to characterize the temperature of the plasma flow is to consider the temperature in the core of the flow. Another way to characterize the temperature of the plasma flow is to consider the average temperature in the flow at a given cross section. The term "outlet temperature" and its variations refer to a representative temperature, preferably the core temperature, of the plasma flow as it is discharged through outlet 3.

Figure 1B:
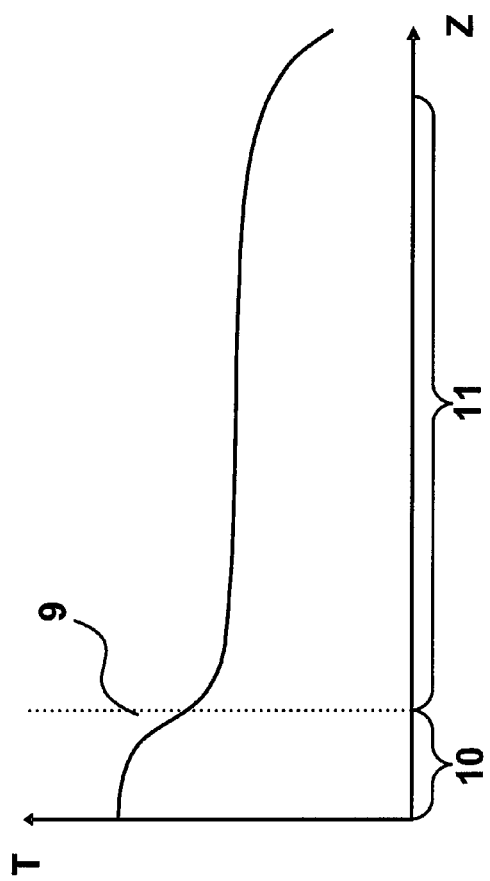
FIG. 1B is a graph of the temperature of a typical plasma flow along the plasma flow axis.

The temperature of plasma flow 1 decreases as it propagates along axis 4 away from outlet 3. Plasma flow 1 has a proximal region 6 with a temperature close to the outlet temperature of the plasma flow as it is discharged from outlet 3. Plasma flow 1 also has a distal region 7 with a lower temperature. Because there is little mixing with surrounding medium 5, a laminar plasma flow maintains a substantially uniform temperature in region 7 over a significant distance away from outlet 3. FIG. 1B shows a plot of the temperature of the plasma flow along plasma flow axis 4. Region 10 and region 11 in FIG. 1B correspond to the temperatures found in proximal region 6 and distal region 7 in FIG. 1A, respectively. As seen from FIG. 1B, the plasma flow temperature maintains a relatively constant temperature over region 10. At distance 9 from the plasma-generating device, the plasma flow temperature decreases significantly. In region 11, the plasma flow maintains a relatively constant temperature. Distance 9, at which the plasma flow experiences the most significant temperature drop off, is considered a demarcation point between the proximal region 6 and distal region 7.

Figure 2:
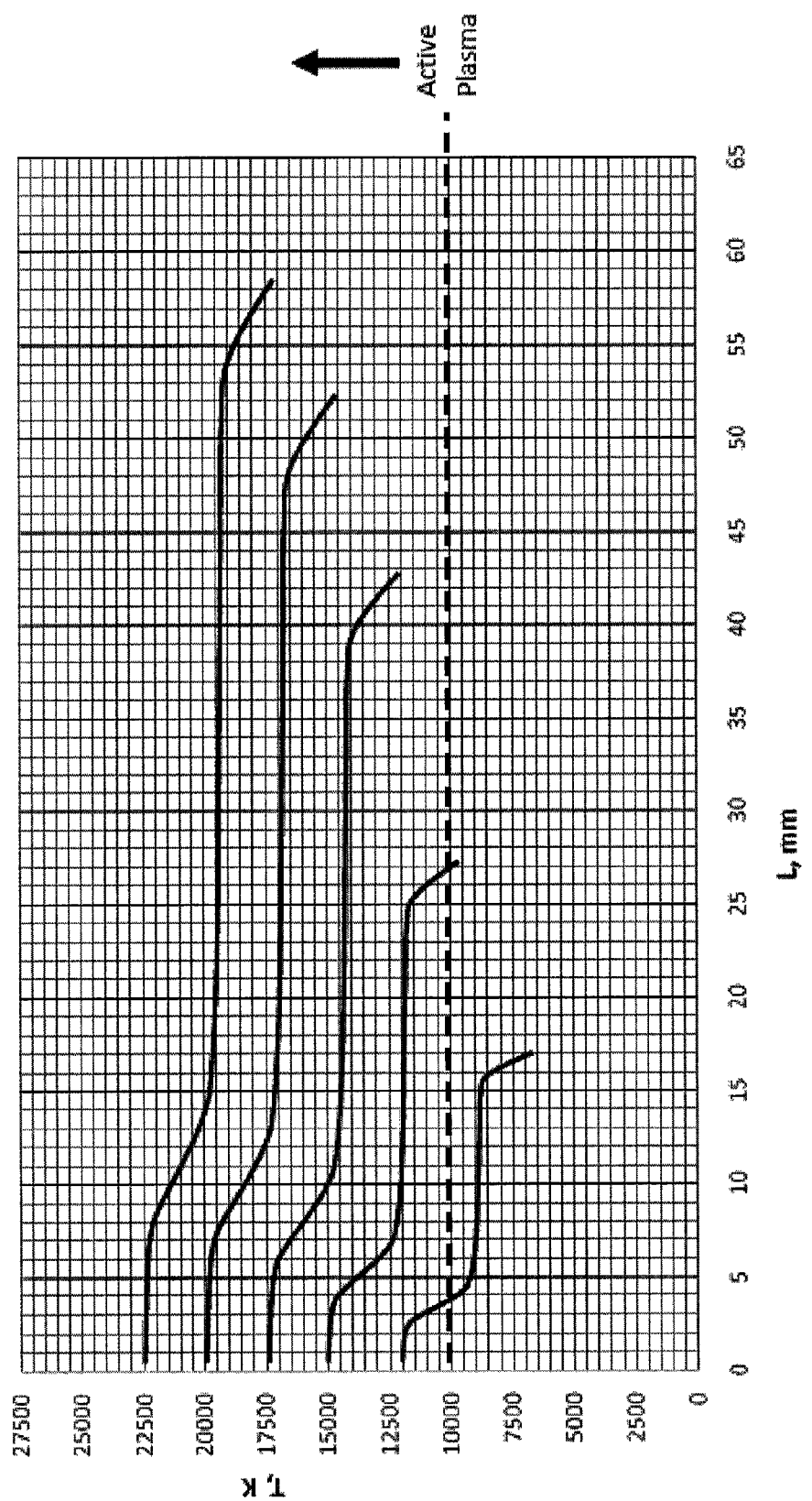
FIG. 2 is a graph of the temperature along the plasma flow axis of several plasma flows generated by a plasma-generating device with an outlet diameter of 0.5 mm.

FIG. 2 shows a series of plasma temperature measurements taken at a various distances from a plasma-generating device. The diameter of outlet 3 used for these measurements was 0.5 mm. Each line in FIG. 2 represents a different outlet temperature. Each line clearly exhibits a proximal region and distal region as described above. As seen from FIG. 2, as the outlet temperature of the plasma flow increases, the proximal and distal regions extend over larger distances away from outlet 3 of the plasma-generating device.

There is no clear boundary of the plasma flow. For the purposes of this disclosure, the discussions of volumetric plasma oscillations should be understood as volumetric oscillations of "active plasma." In this disclosure, active plasma is defined as plasma with a temperature above certain threshold of interest. For example, for surgical applications, such threshold may be 10,000K. For some industrial applications, this threshold may be higher, while for cosmetic applications this threshold may be lower. Plasma with a temperature lower than a given threshold, outside the active plasma boundary, still may have beneficial effects. This, in this disclosure, "active plasma" provides a way to conveniently describe the volume (or zone) of a plasma flow, but is not meant to delimit the portion of what may be useful plasma. For FIG. 2, the illustrated active plasma threshold is 10,000 K.

In reference to the size of a plasma flow, for purposes of this disclosure, the term "volume" is defined as the space occupied by active plasma. When the plasma flow discharged from outlet 3 has a relatively high temperature, the plasma in both proximal region 6 and distal region 7 may contain active plasma. Accordingly, the volume of such a plasma flow would span both of these regions. For example, in FIG. 2 the curve corresponding to a plasma flow with an outlet temperature of 15,000 K shows a distal region with a temperature of approximately 12,000 K. For a plasma flow with a relatively low outlet temperature, for example, approximately 12,000 K, only the proximal region contains active plasma. In this case, the volume of the plasma flow is significantly smaller. Plasma flows with an outlet temperature of less than the active plasma threshold by definition have no active plasma and no volume.

The terms "length" and "width," with reference to the plasma flow are defined in a similar manner as "volume." The "length" of a plasma flow is the distance between outlet 3 and the point along plasma flow axis 4 where the temperature drops below 10,000 K. FIG. 3 shows a plasma flow with active plasma volume 20. The length of this plasma flow is the distance between outlet 3 and point 21 along plasma flow axis 4. The "width" of a plasma flow at a given distance from outlet 3 is defined as the diameter of a cross-section of the active plasma flow transverse to plasma flow axis 4. For example, the plasma flow in FIG. 3 has a maximum width in plane 22, which is the diameter of the region in plane 22 occupied by active plasma. The term "spot diameter" refers to the width of the plasma flow at the spot where it comes in contact with a substrate, such as a tissue.

In a preferred embodiment, volumetrically oscillating plasma is generated with a plasma-generating device with annular components. In this embodiment, because outlet 3, and as a result a cross-section of the plasma flow, is circular, the width of the plasma flow is substantially the same at any angle in the cross-section. In other embodiments, the width of the plasma flow may differ when measured at different angles. In those embodiments, for notational convenience, the width of a plasma flow is defined as the largest cross-sectional diameter of the active plasma transverse to plasma flow axis 4.

A "volumetrically oscillating plasma flow," as the term is used herein, refers to a flow of plasma whose volume varies in time by expanding and contracting. Preferably these volumetric variations are controlled. For medical applications, for example, the greatest benefit is achieved when the plasma volume varies according to a periodic pattern.

A volumetrically oscillating plasma flow can be created by providing to the plasma-generating gas energy with a power density that oscillates in time between a low level during a low intensity interval and a high level during a high intensity interval. Providing energy with a low level power density to the plasma-generating gas results in the generation of low intensity plasma, while providing energy with a high level power density results in generation of high intensity plasma.

Additional energy provided to the plasma-generating gas during the high intensity interval, as compared to the low intensity interval, results in an increase of the plasma flow temperature. In a preferred embodiment, energy is supplied by passing an electric current through the plasma-generating gas as it flows through a plasma-generating device. In alternative embodiments the energy may be supplied to the plasma-generating gas using microwaves or by means of electromagnetic fields as known in the art. The plasma flow generated by an energy with oscillating power density, provided to the plasma-generating gas, has a volume that oscillates in time with the same frequency as the energy.

Figure 4A:
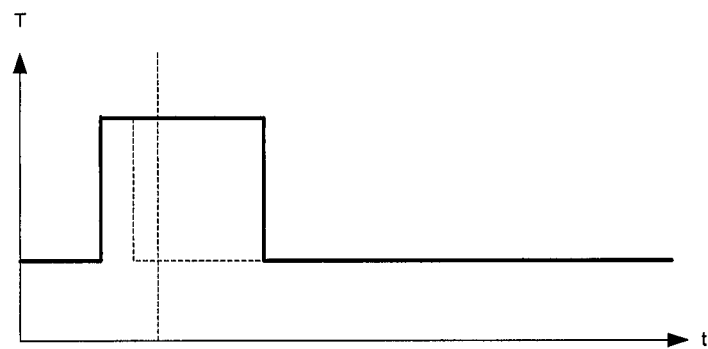
FIG. 4A is a graph of the temperature of a volumetrically oscillating plasma flow over time during a single oscillation.

An exemplary current waveform that meets the criteria of supplying a low power density level and a high power density level to the plasma-generating gas is a biased pulse wave, in which the current is biased at a low level, referred to as the "bias level" and has pulses reaching a high level, referred to as the "pulse level." FIGS. 4A-F illustrate the behavior of the plasma particles at different times during a single period of a biased pulse wave volumetric oscillation. FIG. 4A shows the temperature of the plasma as a function of time, starting at a low temperature corresponding to a low intensity plasma during a time interval corresponding to the bias current, then rising rapidly to a high temperature corresponding to a high intensity plasma during a time interval corresponding to the pulse current, and then returning rapidly to the low temperature corresponding to the low intensity plasma during the time interval corresponding to the next bias current. The characteristic behavior of the particles at the stages shown in FIG. 4A is shown in FIGS. 4B-F, respectively.

Figure 4B:
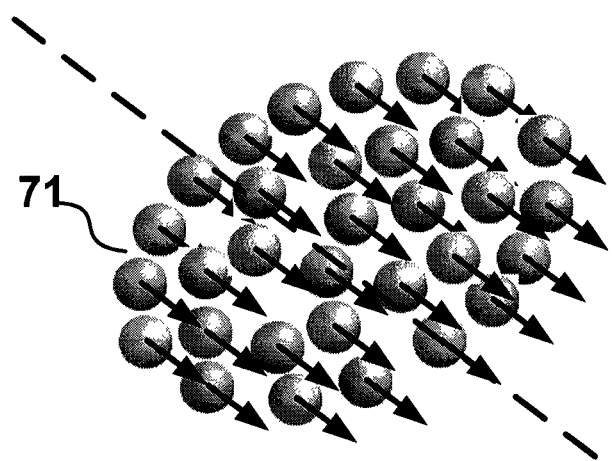
Figure 4C:
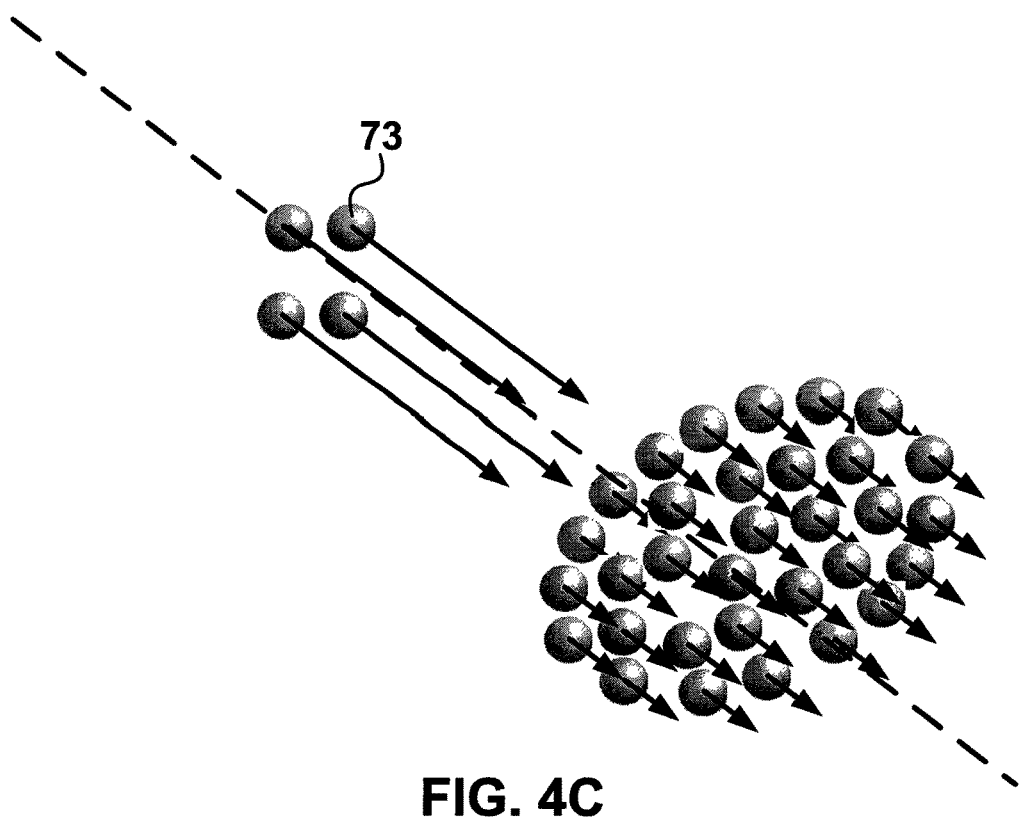
Figure 4D:
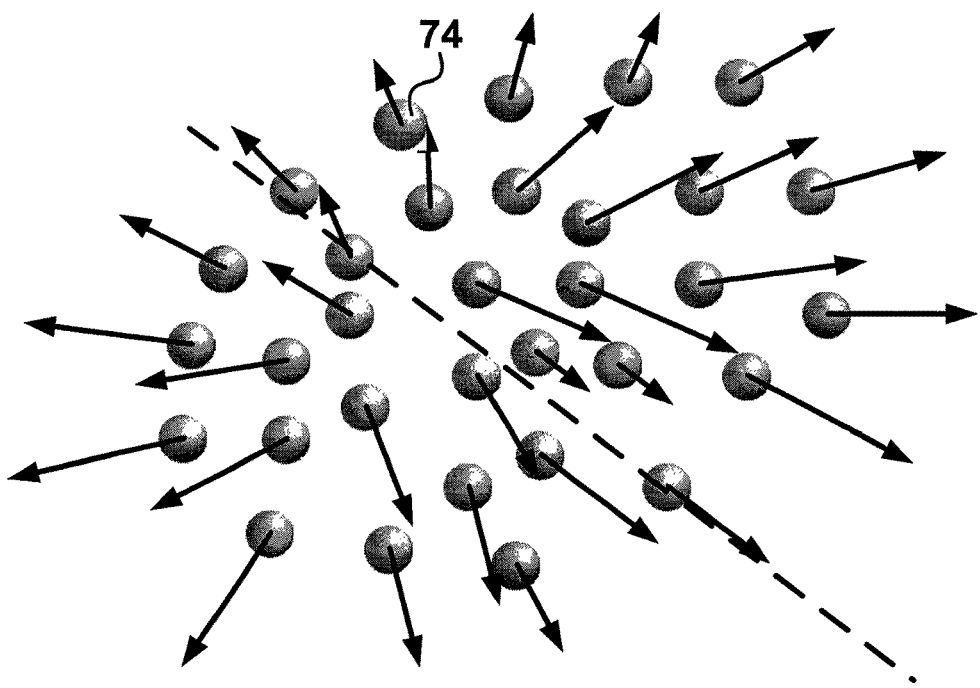
Figure 4E:
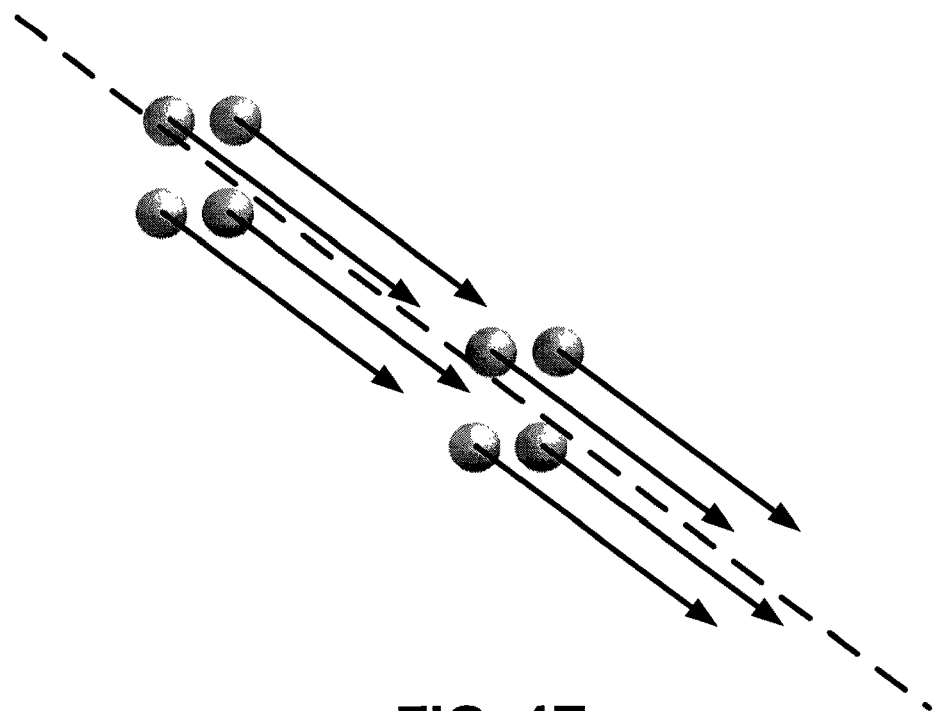

As shown in FIG. 4B, relatively slow particles 71, corresponding to the low intensity plasma, travel along the plasma flow axis. Particle velocities are shown by their associated velocity vectors. Due to a relatively low temperature, particles 71 have a relatively high density. As shown in FIG. 4C, as the temperature of the plasma flow rapidly increases at the beginning of the high intensity interval, particles 73 accelerate to a higher velocity than the velocity of particles 71. Due to a relatively high temperature, particles 73 have a relatively low density. These sparse, fast-moving particles 73 travel at a high speed and quickly catch up to dense, slow-moving particles 71 downstream in the plasma flow. As shown FIG. 4D, collisions between the sparse, fast-moving particles 73 and the dense, slow-moving particles 71 cause plasma particles to scatter. Scattered particles 74 now have components to their velocity vectors in both the radial and axial directions. This scattering causes the width of the plasma flow to increase, marking the beginning of a radial oscillation. This process is analogous to a single billiard ball hitting a group of billiard balls, all scattering in different directions after the hit.

At a certain time, referred to as transition time $t_{transition}$, the fast-moving low density particles of the high intensity plasma have pushed away all of the low intensity, high density particles of the low intensity plasma. Thereafter, the fast-moving low density particles of the high intensity plasma propagate unimpeded along the plasma flow axis. At this time, shown in FIG. 4E, the plasma flow length begins to increase, marking the beginning of an axial oscillation.

Figure 4F:
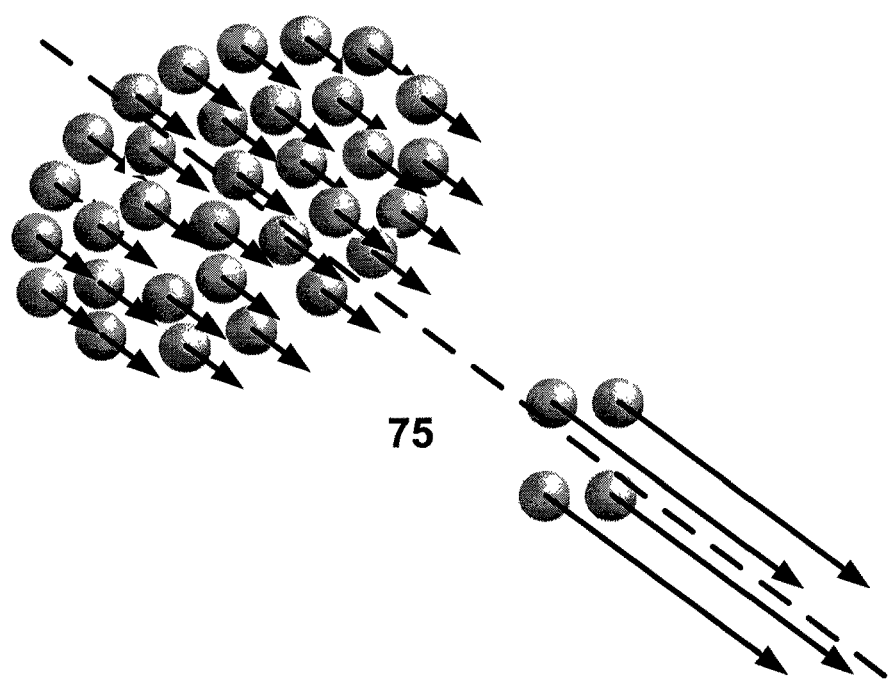
Figure 4G:
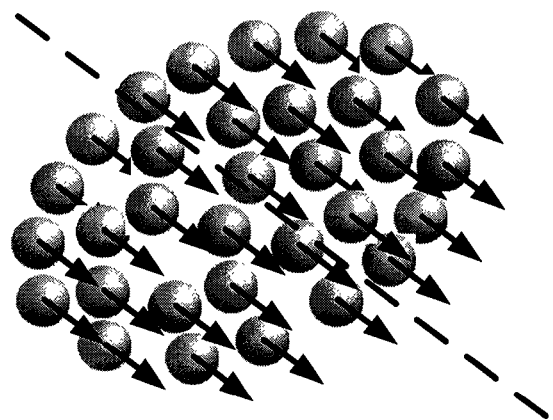

In FIG. 4F, with the drop in temperature, caused by the drop in the current at the end of the pulse, the velocity of the particles discharged from the device drops and the density of the plasma increases. This creates pressure gap 75 because slow-moving particles 71 of the next low intensity interval do not catch up with the fast-moving particles 73.

If the current is dropped to the bias level before transition time $t_{transition}$) the length of the plasma flow does not have an opportunity to increase. In this situation, the plasma flow would only undergo the processes shown in FIGS. 4B, 4C, 4D, and 4G. Therefore, a pulse of current that is shorter than transition time $t_{transition}$ produces a predominantly radial oscillation, while a pulse of current that is longer than transition time $t_{transition}$ produces a predominantly axial oscillation that is preceded by a single radial expansion. Volumetric oscillations are produced by repeated increases and decreases in the supplied current. In this disclosure the term "radially oscillating plasma flow" and its derivatives refer to a volumetrically oscillating plasma flow with radial oscillations and small-scale axial oscillations, i.e., oscillations that do not exceed one order of magnitude the size of the outlet diameter. The term "axially oscillating plasma flow" and its derivatives refers to a volumetrically oscillating plasma flow with predominantly large-scale axial oscillations, i.e., oscillations that exceed one order of magnitude the size of the outlet diameter. It should be understood, however, that axially oscillating plasma flow starts with a radial expansion.

Another way to describe a volumetrically oscillating plasma flow is by observing its behavior in a space with a constant volume. In this fixed space, a portion of the space is occupied by plasma and the remaining portion is occupied by the surrounding medium. Such medium is typically air, but may be another gas, or even a liquid for example in certain laparoscopic surgeries or even underwater applications. For a volumetrically oscillating plasma flow, the portion of the space occupied by plasma oscillates in time. Conversely, the portion of the space occupied by the surrounding medium also oscillates. In the fixed space, during a low intensity interval, plasma occupies a smaller portion of the space than during a high intensity interval. In a preferred embodiment, the low intensity plasma has a portion with a temperature of at least 10,000 K and the high intensity plasma has a portion with a temperature at least 10,000 K above that of the low intensity plasma temperature. It should be noted that the portion of the space occupied by plasma and the surrounding medium are not necessarily contiguous. Plasma particles may be dispersed through the surrounding medium as shown in FIG. 5. Further, because the densities of plasma and the surrounding medium may be vastly different, certain methods of volume computation should preferably take the density into consideration.

An alternative way of characterizing a volumetrically oscillating plasma flow is by expansion and contraction of active plasma. In a preferred embodiment the expansion and contractions are according to a controlled pattern.

Volumetrically oscillating plasma flows also produce acoustic waves. Briefly, at the time of plasma flow expansion, when plasma temperature rapidly rises, air is displaced by the expanding plasma flow. At the time of plasma flow contraction, when the plasma temperature rapidly drops, the air is pulled into the resultant low pressure region that was just occupied by the fast-moving plasma particles. When the plasma flow oscillates repeatedly, these air movements form an acoustic wave.

Volumetrically oscillating plasma flows are useful in a variety of applications, for which the use of continuous plasma flows, produced with constant energy supply, is not ideal. The illustrative applications in this disclosure are in the medical field. Other applications include, among others, the treatment of electronic components, cosmetics, and waste disposal applications.

5.2 System

Referring to FIG. 6, an embodiment of a system capable of providing a volumetrically oscillating plasma flow generally comprises console 31 and plasma-generating device 32. In a preferred embodiment, console 31 provides energy in the form of an electric current, plasma-generating gas, and coolant to plasma-generating device 32 through connector 33. Console 31 preferably has control circuitry, such as a processor, for operating the plasma-generating device 32 and a user interface comprised of a display and controls. An operator programs the mode of operation of the system with the controls of console 31 in accordance with parameters for a given application, then uses plasma-generating device 32 to discharge a plasma flow.

In a preferred embodiment specifically adopted for surgical use, plasma-generating device 32 is a hand-held surgical device. The operator may be a trained medical professional, such as a surgeon. Plasma-generating device 32 may be adapted for performing open or laparoscopic surgery.

FIG. 7 shows a longitudinal cross-section of a multi-electrode plasma-generating device 41 suitable for generating volumetrically oscillating plasma flows. Plasma-generating device 41 comprises anode 42, a cathode 43, and a number of intermediate electrodes 46', 46", 46'". Depending on the application, the number of the intermediate electrodes may vary. Together with anode 42, intermediate electrodes 46', 46", 46'" form a plasma channel. The cross-sectional diameter of this plasma channel may vary with distance from the cathode. FIG. 7 shows a plasma channel comprising two separate portions with different cross-sectional diameters. Plasma channel heating portion 58 is formed by intermediate electrodes 46', 46", and 46'". Anode 42 forms plasma channel anode portion 45. In this embodiment the cross-sectional diameter of plasma channel heating portion 58 is slightly smaller than that of the plasma channel anode portion 45. In the preferred embodiment, the cross-sectional diameter of plasma channel anode portion 45 corresponds to the diameter of outlet 3, which is one of the key parameters controlling the properties of the generated plasma flow. Intermediate electrodes 46', 46", 46'" and anode 42 are separated from direct contact with each other by annular insulators 47', 47", 47'". Sleeve 44 forms gas supply channel 59 that runs along cathode 43 into the cathode chamber 49 that hosts tip 48 of cathode 43.

During operation, the plasma-generating gas is supplied into plasma-generating device 41. Once in the plasma-generating device the plasma-generating gas is passed to plasma chamber 49 and then into plasma channel heating portion 58 through gas supply channel 44. From there, the plasma-generating gas enters plasma channel anode portion 45. After traversing plasma channel anode portion 45, the plasma-generating gas is discharged through outlet 3. The plasma-generating gas is preferably argon. Alternatively, an inert gas or air may be used as the plasma-generating gas. A plasma flow is generated by heating the plasma-generating gas as it passes through plasma channel heating portion 58. In the preferred embodiment, the energy for heating the plasma flow in plasma channel heating portion 58 is transferred to the plasma-generating gas by an electric arc established between cathode 43 and anode 42. This electric arc is generated by passing a current from console 31 between cathode 43 and anode 42.

For a plasma flow formed with an electric current arc discharge, the temperature of the plasma flow depends on the current of the electric arc, the plasma-generating gas flow rate, and the diameter of heating portion 58. The temperature of the plasma flow as it leaves heating portion 58 is proportional to the ratio of the current to the diameter of heating portion 58, i.e., $$T \propto \frac{I}{d_{heating}},$$

where T is the temperature in K, I is the current in A, and $d_{heating}$ is the diameter of heating portion 58 in mm. As seen from the above relationship, high temperatures can be achieved by passing a high current through a plasma-generating device with a small heating portion diameter. Electrodes 46 and anode 42 are composed of presently known in the art materials that can safely sustain a continuous temperature of 12,000-13,000 K. Exceeding this temperature increases the risk of electrode erosion, which is unacceptable for medical applications in which plasma impurities may be harmful to the patient. It was observed, however, that increasing the temperature up to 30,000 K temporarily, for up to several milliseconds, does not result in electrode erosion. Temporary increases of the current passed between cathode 43 and anode 42 up to 30 A were found to not cause erosion and to be otherwise safe, while increasing the plasma flow temperature to 20,000-30,000 K. To achieve 30,000 K with this current, the diameter of heating portion 58 should be 0.6 mm or less, and is preferably 0.3-0.5 mm.

The plasma is discharged from outlet 3 of the plasma-generating device. The preferred outlet diameter varies based on the application. For example, medical applications such as tissue cutting require a small width plasma flow to achieve precise cuts. Referring again to FIG. 7, this embodiment shows a plasma-generating device where the diameter of the plasma channel anode portion 45 and the diameter of outlet 3 are not much larger than the diameter of plasma channel heating portion 58. In the preferred embodiment, the diameter of outlet 3 is about 0.3-0.8 mm, preferably 0.5 mm.

For some applications, an outlet with a large diameter is preferred. A large outlet diameter allows generating a plasma flow with a large spot diameter. Such a large spot diameter is preferred for certain applications such as wound healing, cosmetics, and cleaning. Some applications may not require the volumetrically oscillating plasma to have very high outlet temperatures. But for those applications that actually require high outlet temperatures and a large spot diameter, an embodiment as illustrated in FIG. 8 may be used.

As shown in FIG. 8, the diameter of the plasma flow may be gradually expanded within the device. FIG. 8 shows an embodiment of the plasma-generating device with a plasma channel having an expansion portion. The plasma channel comprises heating portion 58, expansion portion 57, and anode portion 45. Expansion portion 57 comprises one or more expansion sections. In the embodiment shown in FIG. 8, expansion portion 57 comprises expansion sections 54, 55, 56. Starting at heating portion 58, the diameter of each successive expansion section increases, terminating with anode portion 45 with the desired outlet diameter for the particular application. To guarantee proper expansion of the plasma flow in the plasma channel, in the context of the examples discussed above each successive section should preferably increase in diameter by about 0.2-0.6 mm, and have a length between approximately one and two times its diameter.

In some embodiments of the plasma-generating device, heating portion 58 and each section of expansion portion 57 are formed by separate electrodes. In other embodiments of the plasma-generating device, a single intermediate electrode may form portions of two or more adjacent sections. In yet some other embodiments, some intermediate electrodes may form a portion of a section, or an entire section, of the heating or expansion portions, and other intermediate electrodes may form only portions of two or more adjacent sections. In the embodiment shown in FIG. 8, intermediate electrode 46' forms a cathode chamber and a part of the heating portion, intermediate electrode 46" forms expansion section 54 (and part of heating portion 58), and intermediate electrode 46''' forms expansion sections 55 and 56.

Referring back to FIG. 6, in the preferred embodiment, console 31 contains control circuitry capable of causing the power supply to deliver an electric current suitable for generating a volumetrically oscillating plasma flow. The current is transmitted to plasma-generating device 41 through connection 33 to console 31. The control circuitry is preferably capable of causing the power supply to provide an arbitrary periodic current wave, such as wave 54 shown in FIG. 9. The basic characteristic of current 54 is repetition of a desired waveform with period τ. Current 54 oscillates between a low-level current $I_L$, and high-level current $I_H$. This arbitrary current waveform may have features that vary slowly with time such as smooth region 55 or rapidly such as rectangular pulse 56. A variety of periodic current waves may be suitable for generating a volumetrically oscillating plasma flow.

As discussed above, volumetric oscillations of a plasma flow are caused by changes in the plasma flow temperature, which alters the length, width, and volume of the plasma flow. Particularly for radial oscillations, the magnitude of these changes depends on how rapidly the plasma temperature changes. This is due to the scattering mechanism described above in connection with FIG. 4D, which is more pronounced when the differences in density and velocity of the particles are significant. For example, if current 54 varies slowly, the density and velocity of the particles change only gradually and the amount of radial scattering is small.

In a preferred embodiment, the control circuitry is capable of causing the power supply to generate rectangular pulses. In this embodiment, the power supply uses three current sources, as schematically shown in FIG. 10. The first current source is capable of providing a constant bias current. The second current source is capable of providing rectangular pulses with a frequency of about 20-100 Hz. Preferably the second current source has a ramp rate of 25 A per 10 μs. The third current source is capable of generating rectangular pulses with a frequency of about 20,000-100,000 Hz. The third current source has a ramp rate of at least 20 A per 1 μs, preferably more 25 A per 1 μs. The power supply preferably generates up to 50 A. A higher current which may be unacceptable for medical applications, however, may be preferred for industrial applications.

For many applications it is desirable to introduce rapid variations in the current to produce radially or axially oscillating plasma flows. FIG. 11 shows a biased pulse wave capable of producing such oscillations. In this preferred embodiment, the oscillating current used to generate a volumetrically oscillating plasma flow maintains the bias current level, coupled with periodic pulses reaching the pulse current level. A single period 51 of current 50 may be viewed as the high intensity interval 52 and low intensity interval 53. During low intensity interval 53, the current is maintained at bias current level $I_L$. During high intensity interval 52 the current is raised to pulse current level $I_H$. Low intensity interval 53 and high intensity interval 52 are maintained for times 53 and 52, respectively. The duty cycle D of current 50 is given by the ratio of high intensity interval 52 $t_H$ and the period of the oscillation, $t_H+t_L$ as $$D = \frac{t_H}{t_H + t_L}.$$

The frequency f of current 50 oscillations is $$f = \frac{1}{t_H + t_L}.$$

As explained above in connection with FIGS. 4A-G, a biased pulse current wave, such as the one shown in FIG. 11, produces a volumetrically oscillating plasma flow that can be radially or axially oscillating depending on the frequency. Significant radial oscillations, for example, can be generated when the current has a frequency greater than 2,000 Hz, preferably in the range of 20,000-30,000 Hz. This frequency ensures that the duration of the pulse current level is close to the transition time of the plasma flow, which does not provide sufficient time for a significant axial oscillation to develop.

For generation of predominantly axial oscillations, the frequency of the biased pulse wave is preferably 20-100 Hz. This frequency range ensures that the duration of the high intensity interval is longer than the transition time, so that the plasma flow has the opportunity to expand in length during the pulse. Regardless of the frequency used, however, the average current is determined by the duty cycle D of the biased pulse wave. In general, for volumetrically oscillating plasma flows the average current must be kept at a level low enough to avoid damaging components of the plasma-generating device. At the same time, to create a significant increase in temperature of the plasma flow, pulse current level, $I_H$, must be relatively high. The operational bias current level, $I_L$, is 3-10 A, preferably around 6 A, and the pulse current level, $I_H$, is around 25-30 A, with the duty cycle D of 0.05-0.15. These preferred settings produce an average current level of only 7.2-9.6 A, while alternating between a low temperature of 11,000 K and a high temperature of 20,000-30,000 K. The brief current increases to 30 A were found not to cause damage to the plasma-generating device components.

In some embodiments the control circuit is capable of generating a modulated biased pulse wave shown in FIG. 12. In the wave shown in FIG. 12 high frequency pulses are modulated by low frequency pulses. This current wave combines the effects of both low frequency and high frequency biased pulse waves. This current wave is structured like a low frequency biased pulse wave, except that the constant pulse current level during the high intensity interval has been replaced by a high frequency biased pulse wave. Preferably, for the modulated pulse wave, the high-frequency frequency is 20,000-30,000 Hz, high frequency duty cycle is 0.35-0.65, low-frequency frequency is 20-100 Hz, low frequency duty cycle is 0.05-0.15, bias current level is 3-10 A, and pulse current level is 25-30 A. In one embodiment of the modulated biased pulse wave, shown in FIG. 12, the low frequency period $\tau_1$ is 30 ms and the low frequency duty cycle $D_1$ is 0.13. The high frequency period $\tau_2$ is 40 µm and the high period duty cycle $D_2$ is 0.5. When such a current wave is used to generate a volumetrically oscillating plasma flow the resulting plasma flow exhibits significant axial oscillations coupled with high frequency radial oscillations during the high intensity interval. The large high frequency duty cycle $D_2$ ensures that the high frequency oscillations do not limit the length of the plasma flow during the high intensity interval.

Instead of a rectangular low frequency pulse, other envelope functions can be used. FIGS. 13A and 13B show examples of such waves. In FIG. 13A, a sine wave is used as an envelope for the high frequency pulses. In FIG. 13B, a chirp wave is used as an envelope of the low frequency pulse. Using a non-constant envelope for the high frequency pulse provides amplitude modulation of the current wave during the high intensity interval. Further, the bias current level does not need to be constant. In some embodiments, the bias current level changes in time. All electric current waveforms that are disclosed in connection with the preferred embodiments may provide energy to the plasma-generating gas which may alternatively be provided by other means such as magnetic field or microwaves.

Device 32 may be also be adapted for generating an intermittent plasma flow. An intermittent plasma flow is a flow that is heated by an electric arc periodically. The electric arc is periodically turned 'on' and 'off.' During the 'on' state the arc between cathode 43 and anode 42 is established and maintained. During the 'off' state the arc is extinguished and room-temperature plasma-generating gas is discharged from outlet 3. An intermittent plasma flow, in which the plasma flow ceases, should not be confused with a volumetrically oscillating plasma flow, in which the plasma volume increases and decreases. To produce intermittent plasma, the plasma-generating device has to overcome two problems. First, during the startup of the 'on' state, electrodes erode creating impurities introduced into the plasma flow. While this does not present a problem for a non-intermittent plasma flow in which the startup occurs once for the entire procedure, for the intermittent plasma, the generated impurities for each 'on' period may render the device unsuitable for medical use. This problem is overcome by the use of a special startup current sequence before the current is ramped to the operational level during the 'on' state as shown in FIG. 15B. Second, the area of electric arc attachment to the cathode grows with each subsequent 'on' state until it includes the cathode holder. When the area of the electric arc attachment reaches the cathode holder, the cathode holder begins to melt, which introduces impurities into the plasma flow. This problem is overcome by the use of the specialized multi-cathode assembly disclosed in U.S. Pat. No. 7,589,473, incorporated herein by reference for all purposes.

FIG. 14A shows an alternative embodiment of plasma-generating device 32 specifically adapted for the generation of a volumetrically oscillating intermittent plasma flow. Such a device uses specialized multi-cathode assembly 90 comprising multiple cathodes 91, 92, 93, held together by cathode holder 94, shown in FIG. 14B. When specialized multi-cathode assembly 90 is used to generate intermittent plasma flows, the area of electric arc attachment on cathode assembly 90 settles on a single cathode during each 'on' state. This allows the other cathodes to cool when they are not being used to pass current. Because only a limited portion of cathodes 91, 92, 93 heat up to be able to emit electrodes, the cathode assembly will maintain a stable temperature and the area of the electric arc attachment will not reach cathode holder 94. While this specialized multi-cathode assembly is particularly suited for generating intermittent plasma flows, it can also be used for generating non-intermittent plasma flows.

With reference to FIG. 8, when the plasma-generating device generates an intermittent plasma flow, the operational current level may not be achieved immediately. With reference to FIG. 15B, the operational current occurring between times $t_8$ and $t_9$ is made possible by applying the voltage pattern shown in FIG. 15A and passing the current shown in FIG. 15B, up to time $t_8$, through the cathode assembly 90 and anode 42 (not shown in FIG. 14A). At time $t_8$, the operational current is reached, and the plasma behaves like a continuous plasma flow from time $t_8$ until time $t_9$ as the operational current is maintained at a constant level. During operation of such a device, the plasma flow completely ceases during the 'off' state.

During a single 'on' state of the intermittent plasma flow, many periods of volumetric oscillation may occur. In one embodiment, the duration of an 'on' state may be controlled through the console. For some applications, the optimal duration of the 'on' state is approximately 5 ms. During an 'on' state with this duration, a number of radial plasma oscillations may occur. For a longer 'on' state, such as 1 s, there is enough time to generate a number of axial oscillations as well as radial oscillations.

By replacing the constant operational current during the 'on' state with a biased pulse wave such as current 50 shown FIG. 11, the intermittent plasma flow embodiment generates a volumetrically oscillating plasma flow during the 'on' state. FIG. 15C shows a single period of a current wave with these properties, which is suitable for generating a volumetrically oscillating intermittent plasma flow. In a preferred embodiment, the length of the 'on' state is 1-100 ms with a constant bias current level of 1-3 A. The pulse current level is preferably about 30-50 A. Oscillations during the 'on' state are accomplished by a high frequency biased pulse wave with a duty cycle of 0.5 and a frequency of 20,000-100,000 Hz.

Referring again to FIG. 6, console 31 also contains control circuitry, such as a processor, to regulate the flow of plasma-generating gas to plasma-generating device 32. In a preferred embodiment, console 31 is mounted on service module 34 that houses the plasma-generating gas supply and preferably coolant. Alternatively, console 31 may be mounted on an overhead arm or on a cart. Console 31 preferably provides a stable and low variable flow rate of plasma-generating gas during operation. In embodiments adapted for surgical procedures, the flow rate is kept relatively low to ensure both a laminar plasma flow and suitable power level for surgery. In a preferred embodiment, the flow rate of plasma-generating gas during operation is about 0.1-0.6 L/min at room temperature, preferably about 0.2-0.5 L/min at room temperature. The plasma-generating gas flows to device 32 through connector 33. To maintain a stable and constant plasma flow rate, the control circuitry preferably maintains the plasma flow at a given flow rate with an accuracy of about 10 mL/min. In a preferred embodiment, the operator is able to select a flow rate using console 31 starting at 0.1 L/min and increasing in increments of about 30 mL/min.

During operation, the temperature of device 41 components, such as cathode 43, intermediate electrodes 46', 46'', 46''', and anode 42, should be kept below the smelting point. To cool these elements, in some embodiments, one or more cooling channels 40 are arranged so that a coolant circulates within plasma-generating device 41. Preferably, water is used as the coolant, however other types of fluids may be used. In a preferred embodiment, the coolant flows in channels 40A and 40B. In FIG. 7, for example, the coolant from console 31 enters device 41 through channel 40A, then goes around anode 42, and leaves device 41 through channel 40B. As the coolant traverses channels 40A and 40B, it absorbs some of the heat generated during operation of device 41.

In other embodiments, shown in FIG. 16, cooling channels pass through device 41. In these embodiments, the coolant may be discharged from the device at coolant outlets 400 located near outlet 3. Such a cooling system is disclosed in U.S. Pat. Pub. No. 2007/0029292, incorporated herein by reference for the purposes of disclosing a pass-through cooling system. Pass-through cooling systems have some advantages. Because there is no need to return the heated coolant and all cooling channels carry the coolant only one way, a lower coolant rate is required and the plasma-generating device can be miniaturized. Further, by discharging the coolant along with the plasma flow it is possible to localize the heating effect of the plasma flow.

Preferably, console 31 also contains control circuitry to regulate the flow of coolant through the system. By maintaining a steady flow of coolant through plasma-generating device 32, console 31 prevents overheating, which can cause damage to device 32. Preferably, for the closed cooling systems shown in FIG. 7, console 31 monitors the temperature increase of the coolant after passing through plasma-generating device 32. This temperature difference can be used to calculate the power output of the device, which can be shown on the display of console 31. In some embodiments, if the change in temperature of the coolant exceeds a certain threshold, for example 10 K, the coolant control circuitry disables the system as a safety precaution.

Connector 33 transfers current, plasma-generating gas, and coolant between console 31 and plasma-generating device 32. Separate connections for each may be used, however, in a medical setting having multiple connections or wires leading to plasma-generating device 32 is inconvenient. Preferably, all the required connections are enclosed into a single connector. In one embodiment, connector 33 comprises shielded wires for applying current to the plasma-generating device, and flexible hoses suitable for transporting the plasma-generating gas to plasma-generating device 32 and circulating the coolant into and out of plasma-generating device 32.

Additional components of a system for generating volumetrically oscillating plasma flows may include a suction module for removing extraneous tissue during surgical procedures. A suction channel may be incorporated into plasma-generating device 32 that allows the suction system to remove the extraneous matter from surgical site through connector 33 and into console 31 for storage and eventual disposal.

5.3 Generation of Volumetrically Oscillating Plasma Flow

Additional aspects of this disclosure are illustrated with reference to FIGS. 17A-C. FIG. 17A shows a high frequency biased pulse wave. The bias current level is shown as numeral 144. The pulse current level is shown as numeral 145. The high frequency period is shown as numeral 143. The high intensity interval is shown as numeral 141 and low intensity interval is shown as numeral 142. FIG. 17B shows a low frequency biased pulse wave. All features of this wave are shown as the same numerals as in FIG. 17A. FIG. 17C shows a modulated biased pulse wave. All features of this wave are referenced by the same numerals, except the high frequency period is shown as numeral 146 and the low frequency period is shown as numeral 143.

Turning to the physical mechanisms giving rise to the formation of volumetrically oscillating plasma flows, in one embodiment an oscillating current such as current 50 shown in FIG. 11 is applied to a plasma-generating gas. Plasma-generating gas heated by bias current $I_L$ forms a low intensity plasma flow, while the plasma-generating gas heated by pulse current $I_H$ forms a high intensity plasma flow. Viewed over time, the resulting plasma flow is a low intensity plasma flow with bursts of high intensity plasma flow. The frequency of the high intensity plasma bursts corresponds to the current pulse frequency.

The periodic change in intensity of the plasma flow results in the oscillation of several key properties of the plasma flow, such as the dynamic pressure $P_d(T)$, the static pressure $p(T)$, the density $\rho(T)$, the enthalpy $h(T)$, and the power $P(T)$, all of which are functions of the plasma temperature. The effect of these oscillations on the volume of the plasma flow depends upon the timescale of these oscillations. High frequency oscillations, i.e. oscillations with a frequency greater than 2,000 Hz, result in a radially oscillating plasma flow, i.e., a volumetrically oscillating plasma flow with radial oscillations and small-scale axial oscillations. Lower frequency oscillations in the range of 20-100 Hz, on the other hand, result in an axially oscillating the plasma flow, i.e., a volumetrically oscillating plasma flow with predominantly large-scale axial oscillations.

FIGS. 18A-C illustrate high and low frequency volumetric oscillations of plasma flow. FIG. 18A shows active plasma 61 during the low intensity interval. This illustration applies equally to the low intensity interval of either low or high frequency oscillations. The volume of active plasma 61 of the low intensity plasma flow is relatively limited. In a preferred embodiment a bias current level $I_L$ of 6 A produces plasma with a temperature of about 11,000-12,000 K. Under these conditions, the volume of active plasma is relatively small and is limited to the proximal region 6, as shown in FIG. 1A. Outside active plasma region 61 shown in FIG. 18A, air mixes with the plasma particles and cools them to a temperature below 10,000 K.

FIG. 18B shows the dynamics of high frequency oscillations of a plasma flow. The oscillation frequency is greater than 2,000 Hz, and is preferably in the ultrasonic range, i.e. greater than 20,000 Hz. In this example, the duty cycle of the current wave is about 0.05-0.15. In a preferred embodiment where the pulse current level $I_H$ is 30 A, the outlet temperature of the high intensity plasma is 20,000-30,000 K. During the high intensity interval, active plasma occupies region 62. The increase in active plasma volume from region 61 to region 62 is due mostly to a significant increase in the width of the plasma flow. This increase in width is accompanied by a modest increase in the length of the plasma flow. Significantly, when oscillations occur at a high frequency, the high intensity plasma flow is shorter and wider than a continuous plasma flow with an outlet temperature of 20,000-30,000 would be. Due to limitations of presently known materials, however, generation of such a continuous plasma flow is presently not difficult. Such a continuous plasma flow would have a large volume due to the presence of a long distal region containing active plasma. In the case of high frequency oscillations, no such distal region forms.

In contrast, low frequency current waves produce plasma flows that exhibit significant predominantly axial oscillations. FIG. 18C shows the dynamics of a volumetrically oscillating plasma flow oscillating at a low frequency. In a preferred embodiment, the current is a biased pulse current wave where the frequency of current pulses is 20-100 Hz, the current wave duty cycle is 0.05-0.15, and the bias current level $I_L$ and pulse current level $I_H$ are 6 A and 30 A, respectively. During a low frequency oscillation, the volume of the plasma flow increases from region 61 to region 62, shown in FIG. 18B, and then to region 63. The greatest increase in the plasma flow volume is attributable to a substantial increase in the plasma flow length. This length can oscillate as much as 40 mm, from a length of approximately 15 mm to 55 mm. In contrast, after transition time $t_{transition}$ the width of the high intensity plasma flow in the proximal region is only slightly larger compared to the low intensity flow width. While the shape of the high intensity plasma flow resembles the shape of a continuous plasma flow with a similar temperature, the two shapes are not the same. The width of the axially oscillating plasma flow at a point significantly removed from the outlet along axis 4 is substantially larger than the width of a continuous plasma flow at the same distance. For an axially oscillating plasma flow discharged from a device with an outlet diameter of 0.5 mm, the width can reach up to 5-6 mm at a distance of 20-50 mm from outlet 3. To achieve the same width with a continuous plasma flow at 20,000-30,000 K, the outlet diameter would need to be 1.2 mm.

FIGS. 19A-C highlight the differences in volume between a continuous plasma flow and the high intensity plasma of volumetrically oscillating flows with low and high frequency. FIG. 19A shows the volume of a continuous plasma flow with an outlet temperature of 20,000 K discharged from an outlet diameter of 0.5 mm. FIG. 19B shows a high intensity plasma flow during the high intensity interval of a high frequency oscillation. FIG. 19C shows a high intensity plasma flow during the high intensity interval of a low frequency oscillation. In the continuous plasma flow shown in FIG. 19A, the outlet temperature is 20,000 K. Comparing FIG. 19A to FIG. 19B shows that the width of the plasma flow near the outlet is significantly greater when using high frequency volumetric oscillations, while the length of the plasma flow is significantly smaller than the continuous plasma flow. Comparing FIG. 19A to FIG. 19C shows that while the lengths of the two plasma flows are comparable, the width of the volumetrically oscillating plasma flow at distance 100 is significantly larger than the width of the continuous plasma flow at the same distance. These differences between volumetrically oscillating plasma flows and continuous plasma flows occur because of the dynamics of the particles forming the plasma flow during a period of oscillation.

The dynamics of the particles forming the plasma flow can be explained as follows. The mass flow rate of the plasma, which is constant for a given plasma-generating gas flow rate, can be expressed by the following equation:

$$\dot{m} = \rho u A,$$

where $\dot{m}$ is the mass flow rate in kg/s, $\rho$ is the density in kg/m$^3$, u is the flow velocity in m/s, and A is the mass flow area in m$^2$. The mass flow area is a constant at outlet 3. Because the mass flow rate at this point is the same during the high intensity interval and the low intensity interval the following relationship holds:

$$\rho_{low} u_{low} = \rho_{high} u_{high}.$$

Further, because the density of the plasma decreases significantly at higher temperatures:

$$\rho_{low} >> \rho_{high},$$

the velocity of the plasma during the high intensity portion of the oscillation is significantly larger, i.e.:

$$u_{low} << u_{high}.$$

If the high intensity interval $t_H$ is very short, the plasma flow is dominated by the scattering behavior observed during the transition time $t_{transition}$. This situation is illustrated in FIG. 20A. Here, the high intensity bursts are terminated around transition time $t_{transition}$, so the length of the plasma flow does not have an opportunity to expand significantly to the length shown in FIG. 19C. Instead, the oscillation of the volume of the plasma flow is mostly due to the change in width occurring as particles are scattered away from the plasma flow axis. Frequencies greater than 2,000 Hz produce radially oscillating plasma flows such as shown in FIG. 6B.

When longer pulse lengths are used, high intensity interval $t_H$ can be much greater than transition time $t_{transition}$. This situation occurs when the high intensity bursts are 0.5-5 ms, which corresponds to a frequency range of 20-100 Hz, having a duty cycle of 0.05-0.15. This situation is shown in FIG. 20B. Here, the high intensity burst lasts long enough for the relatively high velocity, low density plasma particles to extend the active plasma flow to a significant length and achieve the form shown in FIG. 19C. While it appears that the radial scattering which occurs during the transition time may only effect the shape of the plasma flow at the very beginning of a long pulse, in reality the radial scattering was found to have an effect well beyond transition time $t_{transition}$.

Beyond just increasing the width of the plasma flow, the radial scattering of plasma particles changes the dynamic pressure of the plasma flow. Dynamic pressure can be expressed with the following equation:

$$P_d = \frac{1}{2}\rho v^2$$

where $P_d$ is the dynamic pressure in pascals, $\rho$ is the fluid density in $kg/m^3$, and v is the fluid velocity in m/s. The dynamic pressure is a property of plasma flows which influences how far into a medium, such as air or tissue, the plasma flow penetrates. For a plasma flow, the dynamic pressure $P_d$ has the axial component, $P_{da}$, and the radial component, $P_{dr}$. In continuous laminar plasma flows, the velocity of the particles is substantially aligned with the plasma flow axis, so the axial component of the dynamic pressure, $P_{da}$, is relatively high, while the radial component, $P_{dr}$, is negligible. Dynamic pressure components for a continuous plasma flow are reflected in FIG. 21A-C. FIG. 21A shows a constant current that generates a continuous plasma flow. FIG. 21B shows an almost non-existent radial component of the dynamic pressure, $P_{dr}$. FIG. 21C shows a substantial axial component of the dynamic pressure, $P_{da}$. The distribution of the radial and axial component of the plasma flow dynamic pressure changes when the plasma flow oscillates volumetrically. These changes are reflected in FIG. 21D-F. FIG. 21D shows an arbitrary current pulse, that is longer than the transition time. FIG. 21E shows the radial component of the dynamic pressure, $P_{dr}$. In the beginning of the high intensity interval, due to scattering, the radial component of the dynamic pressure $P_{dr}$ quickly reaches its maximum. As the slow-moving, high density particles are pushed away by the fast moving, low density particles, the radial component $P_{dr}$ gradually drops. At the end of the high intensity interval, due to the pressure gap, described in connection with FIG. 4F, the radial component of the dynamic pressure is negative. As the slow-moving, high density particles of the next low intensity interval fill the gap, the radial component of the dynamic pressure $P_{dr}$ levels off. FIG. 21F shows the corresponding axial component of the dynamic pressure, $P_{da}$. The sum of the two dynamic pressure components during the high intensity interval is constant. Accordingly, as the radial component decreases, the axial component decreases.

A significant radial dynamic pressure enables the volumetrically oscillating plasma flow to penetrate into a medium substantially adjacent to the plasma flow, rather than only the medium transverse to the plasma flow axis. In one embodiment, a radially oscillating plasma flow is used to cut tissue during surgery. While the plasma flow accomplishes efficient cutting along the plasma flow axis, the radial component of the dynamic pressure enables a simultaneous penetration into the walls of the cut to achieve haemostasis.

Figure 22A:
Figure 22B:
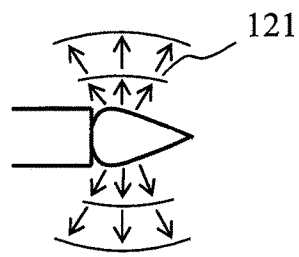
Figure 22C:
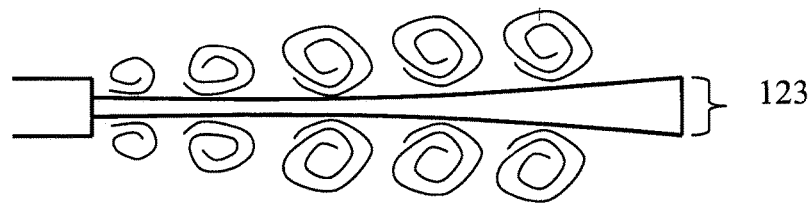
Figure 22D:
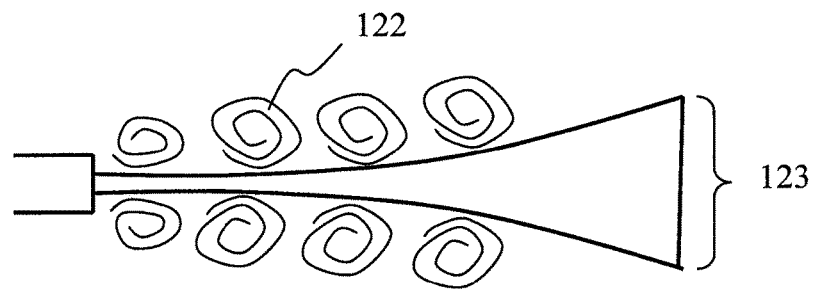

The radial component of the dynamic pressure is also responsible for the increased width of an axially oscillating plasma flow, as can be seen in FIGS. 22A-D. FIG. 22A shows low intensity plasma flow 120, right before the start of a high intensity interval. FIGS. 22B-D show the development of the high intensity plasma flow. FIG. 22B shows the radial scattering of plasma particles, which rapidly increases the radial component of the dynamic pressure. This rapid increase of the radial component of the dynamic pressure causes a pressure wave 121, which disturbs the flow of air surrounding the plasma flow. FIG. 22C shows that shortly after the transition time has passed, the volume of the plasma flow begins to increase in the axial direction. Air eddies 122 form as a result of the radial pressure wave in the beginning of the high intensity interval. Air eddies 122 create a lasting air disturbance, which continues well past the transition time. FIG. 22D shows the resulting expansion of width 123 of the flow that occurs due to air eddies 122 interacting with the plasma flow throughout the duration of the high intensity pulse.

Due to changes in dynamic pressure, oscillations of the plasma flow create acoustic waves. Specifically, expansion of the plasma flow with the accompanying increase in dynamic pressure causes the displacement of air molecules away from the plasma flow. On the other hand, contraction of the plasma flow, with the accompanying decrease in dynamic pressure, creates an area of low pressure around the plasma flow. Air, which is at atmospheric pressure, rushes into the area of low pressure. In a single oscillation, air is pushed away by the expanding plasma and then sucked back into the area of low pressure, which results in a single air oscillation. The air oscillations follow the plasma flow oscillations. As the plasma flow oscillates radially and axially, the air oscillates both radially and axially as well. This is shown in FIG. 18B for a radially oscillating plasma flow and in FIG. 18C for an axially oscillating plasma flow.

When the frequency of plasma oscillations is greater than 20,000 Hz, the acoustic waves are ultrasonic, and can transmit ultrasonic mechanical energy from the plasma flow to a tissue or other medium. In medicine, ultrasonic waves are known to cause cavitation, which has been shown to cause or enhance coagulation. The amount of energy transferred by acoustic waves to a medium depends on the amplitude of the plasma flow volumetric oscillations generating the acoustic waves. The amplitude of volumetric oscillations in a plasma flow, in turn, depends on (1) the difference in temperatures between the low intensity plasma and the high intensity plasma, (2) the high intensity interval $t_H$, and (3) the pulse frequency.

FIG. 23 shows the length of the high intensity plasma as a function of the period τ of oscillation. The plasma-generating device used in the experiment had an outlet diameter of 0.5 mm and generated a biased pulse current wave with a duty cycle of 0.10. To show the influence of temperature on the length of the plasma flow, several measurements were performed each with a different outlet temperature of high intensity plasma. In each measurement the temperature of the low intensity plasma flow was 10,000 K, and the length of the plasma during the low intensity interval was approximately 8 mm, as indicated by line 131. As seen from FIG. 23, higher outlet temperatures of the high intensity plasma result in longer flows. Similarly, longer periods result in longer flows because the plasma flow has a greater opportunity to extend.

FIG. 23 also shows how the amplitude of the volumetric oscillations vary with frequency. For high frequency oscillations, i.e., when τ is less than 0.5 ms (f>2,000 Hz), the length oscillations are small. In this mode, scattering of the plasma flow during the transition time is the dominant mechanism of volumetric oscillations and therefore the volumetric oscillations are predominantly radial. For periods longer than 5 ms significant length oscillations are observed. For example, an axial extension of up to 50 mm for periods of 50 ms (f=20 Hz) is possible.

Regardless of the frequency of oscillations, the difference in temperatures between the high intensity plasma and the low intensity plasma has a dramatic influence on the oscillation amplitude. For example, a temperature difference of approximately 5,300 K produces an oscillation with an amplitude of less than 10 mm for a period of 50 ms as shown in FIG. 23, while a temperature difference of 10,000 K produces an oscillation of approximately 40 mm for a 50 ms period. Therefore, in the preferred embodiment, the temperature of the high intensity plasma is preferably at least 10,000 K greater than the temperature of the low intensity plasma.

It is also possible to combine low frequency axial oscillations with high frequency radial oscillations, so that an axially oscillating plasma flow generates ultrasonic acoustic waves. As discussed above, applying the low frequency biased pulse wave shown in FIG. 11 results in axial oscillations, but does not produce oscillations in dynamic pressure faster than 100 Hz. Using a high frequency biased pulse wave form produces a plasma flow that does not have significant axial oscillations. The modulated biased pulse wave shown in FIG. 12, however, can in fact produce a plasma flow that oscillates significantly in length while still providing ultrasonic energy during the high intensity portion. Basically, the modulated biased pulse wave is a high frequency biased pulse wave modulated by low frequency pulses. The envelope of current 150, shown in FIG. 12, resembles a current suitable for a low frequency axially oscillating plasma flow. In one embodiment, current 150 has low frequency period $\tau_1$ of 30 ms (f≈33 Hz) and a low frequency duty cycle $D_1$ of 0.13. During the high intensity interval of the however, current 150 preferably modulates the high frequency pulses having a high frequency period $\tau_2$ of 40 μs and a high frequency duty cycle $D_2$ of 0.5. High frequency duty cycle $D_2$ of the modulated biased pulse wave is greater than the 0.05-0.15 used for a radially oscillating plasma flow. The larger duty cycle does not disrupt the axial expansion during the high intensity interval. In this preferred embodiment, the plasma flow provides both axial oscillations and radial oscillations during the high intensity interval. For applications that require ultrasonic energy, the frequency of the radial oscillations is in the ultrasonic range, above 20,000 Hz.

5.4 Surgical Applications

Turning now to specific applications of volumetrically oscillating plasma flows, due to the unique properties discussed above, volumetrically oscillating plasma flows are useful, for example, for accomplishing basic surgical tasks such as cutting, vaporization, and coagulation.

5.4.1 Coagulation
5.4.1.1 Principles of Plasma Coagulation

To appreciate the benefits of volumetrically oscillating plasma flows when used for coagulation, an overview of coagulation with continuous plasma flows is provided. Referring to FIG. 24, surgical site 161 is created by the dissection of tissue 163 during surgery. Alternatively, such a site may be created unintentionally as a result of a wound. Bleeding occurs at tissue surface 169, forming pooled blood 167. Blood flows 165 continue at a substantially constant rate until the tissue is coagulated. Typically, blood flow is measured in mL/min or L/min, however, it is also possible to express the bleeding rate $R_{blood}$ in mm/s. In other words, the bleeding rate in a tissue can be measured by how far a particle of blood travels in a unit of time.

The bleeding rate varies by tissue type, and ranges from negligible in tissues such as cartilage to very intense for highly vascular tissue such as liver or kidney. For the purposes of this disclosure, bleeding types are defined as shown in table 1.

TABLE 1

| Bleeding Type | Bleeding Rate, $R_{blood}$ [mm/s] |
| --- | --- |
| Low | <0.3 |
| Medium | 0.3-1.0 |
| High | 1.0-2.0 |
| Intensive | 2.0-3.0 |
| Very Intensive | >3.0 |

For a given tissue, the bleeding rate in mm/s is typically measured as follows. A small wound having an area A is made on the surface of an organ. Typically, this wound is an 8-mm diameter circle. Blood is collected from the wound over a 30-second period and the mass of the blood M in grams is measured. The bleeding rate $R_{blood}$ is calculated using the following equation:

$$R_{blood} = \frac{M}{30 \times \rho_{blood} \times A},$$

where M is the mass of blood in grams collected in 30 seconds, $\rho_{blood}$ is the density of blood in g/mm³, and A is the wound area in mm². In general, and especially for procedures involving high, intensive, or very intensive bleeding rates, achieving hemostasis of bleeding tissues is an essential surgical task.

One way of achieving hemostasis is by applying heat to the bleeding tissue. This heat creates thermal changes that result in the formation of a sealing layer, which prevents further blood flow. FIG. 25 shows a surgical site in which blood flow 165 has been stopped by forming a sealing layer covering underlying tissue 163. Sealing layer 171 is composed of two layers: spongy layer 173 and compact layer 175. Spongy layer 173 is a region in which all fluids have been vaporized, leaving only a solid component. The fluid component of tissue cells, blood, and interstitial fluid make up approximately 80% of the tissue. As a result, once the fluid component is vaporized, what remains is a substantially porous layer, referred to as the spongy layer because it resembles a sponge. Pore diameters are not uniform within spongy layer 173, but average pore sizes and porosities are known for particular tissue types. Table 2 presents average pore diameters and porosities for typical tissue types.

TABLE 2

| Tissue Type | Diameter, d [mm] | Porosity, P [%] |
| --- | --- | --- |
| Lung | 0.06-0.09 | 90-95 |
| Spleen | 0.04-0.07 | 85-90 |
| Liver | 0.035-0.06 | 75-80 |
| Kidney | 0.02-0.04 | 65-70 |

Referring again to FIG. 25, compact layer 175 lies below spongy layer 173, i.e. it is between the spongy layer and underlying tissue 163. For convenience, the term "below" when referring to tissue layers means further away from the surface and the term "above" means closer to the tissue surface. Compact layer 175 is composed primarily of denatured proteins present in tissue and blood. When formed, compact layer 175 is a gel-like solid and is substantially impermeable to fluid flow, thereby preventing the passage of blood flow 165 from underlying tissue 163 to the tissue surface 169.

A preferred sealing layer has both a spongy layer and a compact layer. To completely stop bleeding in the surgical site, sealing layer 171 must be thick enough to withstand the pressure of blood flow 165. On the other hand, sealing layer 171 should be as thin as possible while still achieving coagulation, because healthy tissue 163 is destroyed in the process of creating sealing layer 171. Minimal destruction of healthy tissue is particularly important in sensitive tissues such as the brain and pancreas. In general, minimal destruction of tissue leads to reduced recovery times.

When using a plasma flow for coagulation, the plasma flow is directed at surgical site 161. High energy plasma particles transfer heat to the tissue by colliding with tissue molecules. Referring again to FIG. 25, heat from plasma flow 177 evaporates fluid in the tissue, which forms spongy layer 173. The plasma flow has lost heat as it passed through spongy layer and is unable to vaporize the blood below the spongy layer. In that region, plasma flow 177 raises the temperature of the tissue high enough to denature protein and to form compact layer 175. The thicknesses of the spongy and compact layers depends upon the rate at which plasma flow 177 transfers heat to the tissue at a given depth, and the time during which flow 177 is directed at tissue 163.

The rate at which heat is transferred to the tissue is given by the heat flux q, measured in W/m². The heat flux can be related to the temperature of the plasma flow in the following way:

$$q = \frac{P}{A} = \frac{E(T) \times F_{Plasma}}{A},$$

where power P is measured in W, enthalpy E, which is a function of temperature, is measured in J/kg, area A measured in m², and mass flow rate $F_{Plasma}$ is measured in kg/s.

The initial power level of the plasma flow can be calculated using the temperature and mass flow rate of plasma discharged from the plasma-generating device outlet 3. As the plasma flow propagates along the flow axis, however, interactions with the surrounding medium reduce both the temperature and the flow rate and increase the area over which the plasma flow is distributed.

FIG. 26A shows a continuous plasma flow forming a sealing layer 171 at surgical site 161, while FIG. 26B shows the heat flux q as a function of distance from tissue surface 169. As discussed above, spongy layer 173 is formed when the fluid present in the tissue is vaporized. Tissue surface 169 experiences maximum heat flux 181, and fluids there are quickly vaporized. As plasma flow 177 passes further into the tissue, transferring heat along the way, it loses energy and the heat flux decreases. Formation of the spongy layer 173 at a given depth occurs only if the heat flux is large enough to continuously evaporate blood flow 165. For example, a heat flux of approximately 2.3 W/m² is required to evaporate a blood flow rate of 1 mm/s.

For continuous plasma flow applications, fluid boundary 179 marks the location where heat flux 32 is equal to the heat flux required to evaporate blood flow 165, at fluid boundary 179 liquid blood exists at its boiling point, approximately 100° C.

In compact layer 175, the heat flux is too low to evaporate the incoming blood. Consequently, blood in this region continues to flow toward fluid boundary 179. While not sufficient to vaporize blood and other fluids, the heat flux in the compact layer does raise the temperature of the tissue and blood. When a tissue is heated, protein present in tissue cells and blood undergoes an irreversible reaction, called denaturation. While denaturation of protein occurs at 40-41° C., at such temperatures the denaturation process takes a few hours. If a tissue is heated to 65° C., protein in tissue and blood cells denatures in time suitable for surgery, in under 1 ms. For purposes of this disclosure, the compact layer refers to the layer directly below the spongy layer in which a substantial amount of protein has denatured. For a continuous plasma flow, as shown in FIG. 26A, the compact layer is shown to extend from fluid boundary 179 to denaturation boundary 172. In layer 163 below the compact layer, a substantial amount of protein in the tissue is not denatured. It should be noted that denatured protein becomes visible in morphological samples only several hours after the tissue has been heated, however, denatured protein prevents the flow of blood immediately. Accordingly, morphological samples taken within a few hours after the procedure may not show the true extent of denaturation.

Coagulation with prior art continuous plasma-generating devices required a careful tuning of the plasma flow's heat flux so that the plasma flow would create a spongy layer and a compact layer of sufficient thickness. This was typically done by precisely controlling the distance from the plasma-generating device outlet to the tissue surface for a given plasma flow. With a continuous plasma flow, a 200-300 µm spongy layer coupled with a 300-500 µm compact layer were reliably achieved. These thicknesses can be formed in tissue with low or medium bleeding levels, but cannot be formed in tissue with higher bleeding rates. Further, there are no known reliable ways to increase these thicknesses to stop heavier bleedings. Intuitively, if a higher intensity plasma flow is supplied to a tissue with a high bleeding rate, that flow sublimates the surface of the spongy layer. This sublimation happens faster than the formation of the spongy and compact layers.

Coagulation of a tissue with a high bleeding rate with a continuous plasma flow is schematically shown in FIGS. 27A-C, which depict three consecutive times. In FIG. 27A, a plasma flow with a relatively high heat flux has just been directed at the tissue. Rapidly, the plasma flow forms a relatively thick spongy layer 173. Because the fluid vaporization process, which forms the spongy layer, is much faster than the heat diffusion process, which forms the compact layer, compact layer 175 is still relatively thin. (The vaporization process refers to (1) vaporization of the fluid component or (2) simultaneous sublimation of the solid component and vaporization of the fluid component contained therein. The vaporization process should not be confused with the surgical task of vaporization discussed below.) FIG. 27B shows the tissue a brief time later, after continued application of the plasma flow with a very high heat flux. Due to the large amount of heat transferred to the tissue at the surface, thickness 191 of the spongy layer has been completely sublimated. Despite the inward movement of fluid boundary 179, spongy layer 173 has not increased in thickness. Additionally, compact layer 175 remains relatively thin, as not enough time has passed to denature protein in the underlying tissue. FIG. 27C shows the tissue at yet a later time. Similarly, the result of continued application of the plasma flow is that a thickness 191 of tissue has been sublimated without any increase in thickness of the sealing layer. Increasing the heat flux by increasing the plasma flow temperature or shortening the distance to the tissue (which would increase the heat flux) would not be useful either. If the plasma flow has too high a heat flux, the surface of the sealing layer translates inward as tissue is vaporized without increasing the thickness of the sealing layer. This result is undesirable as healthy tissue is destroyed unnecessarily and the resulting sealing layer, having only a thin compact layer, does not form to have the required thickness to stop heavy bleedings.

The fundamental problem with continuous plasma flow coagulation is illustrated in FIG. 28. The minimum thickness of the spongy layer required for coagulation is at least 200 μm for a continuous plasma. FIG. 28 shows plots of plasma flow heat flux as a function of distance from the surface in the spongy layer. Each curve corresponding to a plasma flow with a different tissue surface heat flux. It is known that a heat flux of 5.3 W/mm² or above results in rapid tissue sublimation. It is also known that a heat flux of 2.3 W/mm² is required to vaporize blood flowing at a rate of 1 mm/s. As seen from the graph a heat flux of 4.2 W/mm² is required at the surface to establish a heat flux of 2.3 W/mm² 200 μm below the tissue surface. As another example, a heat flux of 4.6 W/mm² is required to vaporize blood flowing at a rate of 2 mm/s at a distance of 200 μm from tissue surface. As seen in FIG. 28, to achieve such a heat flux at 200 μm from tissue surface, the surface heat flux must be at least 7.4 W/mm², which exceeds the sublimation threshold. This means that it is not possible to coagulate tissue bleeding with the blood flow rate exceeding 1.4 mm/s, which corresponds to a heat flux at the tissue surface equal to the sublimation threshold. Increasing the heat flux to cope with a high blood flow rate is not effective because sublimation of the surface tissue would offset the formation of the spongy layer.

5.4.1.2 Coagulation with Volumetrically Oscillating Plasma Flow

By using a volumetrically oscillating plasma flow for coagulation, in particular an axially oscillating plasma flow, it is possible to avoid the inherent problems of continuous plasma flows. As discussed above, a high heat flux at the fluid boundary is required for high bleeding rates, and, as a consequence, an even higher heat flux is present at the surface of the tissue. This surface heat flux $q_{surface}$ causes rapid sublimation if maintained continuously, or for a prolonged time period. If, however, the heat flux is rapidly reduced after forming the spongy layer, it is possible to significantly reduce or preferably completely eliminate sublimation. Once a certain thickness of the spongy layer is formed, even a low intensity plasma flow is sufficient to heat the tissue below the spongy layer and to form a compact layer. This low intensity plasma has a surface heat flux $q_{surface}$ that can be directed at the tissue surface without causing significant sublimation because it is below the sublimation threshold $q_{sublimation}$. At the same time, the low intensity plasma has a heat flux that heats the tissue below the spongy layer, thereby forming the compact layer while causing only a minimal sublimation of the spongy layer.

The application of a single oscillation of low frequency volumetrically oscillating flow is shown in FIG. 35A-B. In FIG. 29A, high intensity plasma flow 210 with corresponding length $L_{High}$ is directed at tissue 215. Because the length of a plasma flow is a function of its temperature, the length is a useful indicator of the heat flux that the plasma flow provides. In this case, high intensity plasma flow 210 has a heat flux sufficient to rapidly form spongy layer 212 (and negligible thickness of the compact layer 213). The high intensity interval is given by the preferred low frequency of 20-100 Hz and the preferred duty cycle of 0.05-0.15 of the low frequency biased pulse wave used to generate the axially oscillating plasma flow. For example, for the frequency of 50 Hz and the duty cycle of 0.1, the high intensity plasma is applied for 2 ms. This relatively short application of the high intensity plasma flow evaporates the blood and other fluids from the outer tissue layer. As mentioned above, continued application of high intensity plasma flow 210, however, would cause rapid sublimation at surface 214. Furthermore, continued application of high intensity plasma may cause the erosion of the plasma-generating device components. Accordingly, a prolonged application of high intensity plasma is neither desired nor feasible.

Turning to FIG. 29B, high intensity plasma flow 210 shown in FIG. 29A has changed to low intensity plasma flow 211 having a length $L_{Low}$. The reduced length $L_{Low}$ indicates that the heat flux provided by low intensity plasma flow 211 is less than the heat flux provided by the high intensity plasma flow 210. This reduced heat flux does not rapidly sublimate surface 214. Low intensity plasma flow 211, however, continues to provide heat to the tissue below the spongy layer 212 without excessive destruction of spongy layer 212 forming compact layer 213. This heat increases the thickness of the compact layer, improving the strength of the entire sealing layer. Axially oscillating plasma flows, which alternate between low intensity plasma having a relatively small length and bursts of high intensity plasma having a relatively large length, exhibit a substantial improvement in tissue coagulation over a continuous plasma flow.

Figure 30A:
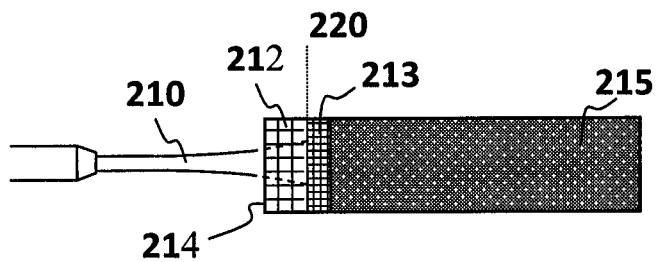

FIGS. 30A-F illustrate coagulation with an axially oscillating plasma flow over three oscillation periods. FIG. 30A shows the effect of the first high intensity pulse of plasma having a length $L_{High}$. After this first high intensity pulse, spongy layer 212 has a thickness of approximately one pore diameter. It has been experimentally determined that one pore diameter of spongy layer is the preferred thickness of the spongy layer that should be formed in a single burst of high intensity plasma. It should be noted that pore diameters are different for different tissues, however 30 μm is a useful approximation. One pore diameter is preferred for two reasons. First, this thickness is small enough to ensure the high intensity pulse of plasma is short enough to avoid substantial sublimation of the tissue surface. Second, this thickness is enough to form a suitably thick spongy layer of about 250 µm in a reasonable number of oscillations. For example, in a tissue with a pore diameter of 30 µm, it takes approximately 8 high intensity pulses to form a suitably thick spongy layer. Even at the lower limit of 20 Hz, the operator needs to apply the plasma to a single spot for less than 0.5 s to form a suitably thick spongy layer.

Figure 30B:
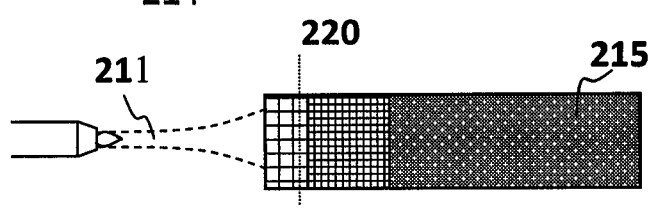

FIG. 30B shows the effect of the low intensity plasma flow. Compared to the high intensity plasma, low intensity plasma 211 has a smaller length $L_{Low}$ and a correspondingly lower heat flux. As a result, during the low intensity interval, surface 214 has not been significantly sublimated despite an extended exposure to the low intensity plasma flow. Due to the continued application of low intensity plasma flow 211, however, protein in deeper layers of tissue continues to denature. This results in an increase of the thickness of compact layer 213. The low intensity interval determines the depth of compact layer formed in a single oscillation of the plasma flow.

Two to four pore diameters is a preferred thickness of compact layer that is formed in a single low intensity portion of an oscillation of the plasma flow. During the next burst of high intensity plasma approximately one pore diameter of compact layer will be converted into the spongy layer as the plasma vaporizes the fluid component in that region. Forming two to four pore diameters of new compact layer during a single low intensity interval ensures that over several oscillations the compact layer increases in thickness at at least the same rate as the spongy layer.

The heat flux of the low intensity plasma is set to preferably have no effect on the spongy layer and to keep the fluid boundary at the depth to which it was advanced during the high intensity interval for the tissue blood flow rate of 2 mm/s. In other words, the heat flux of the low intensity plasma at the fluid boundary should be sufficient to keep the fluid boundary at the same level during the low intensity interval. Of course, this cannot be always achieved. In some cases, the low intensity plasma heat flux will exceed the heat flux required to vaporize fluids at the fluid boundary. This happens, for example, for a blood flow rate below an average blood flow rate of 2 mm/s. In that case, the spongy layer would slowly form during the low intensity interval.

On the other hand, in some cases, the low intensity plasma heat flux at the fluid boundary may be insufficient to vaporize all the incoming blood. In this case heat flux provided by low intensity plasma 211 is that the heat flux needed to completely vaporize the incoming blood from tissue 215, $q_f$ can no longer be provided at fluid boundary 220 shown in FIG. 30A. Accordingly, the fluid boundary 220 has moved closer to the tissue surface during this low intensity plasma of the first oscillation.

FIG. 31A shows a greater detail of the surface region of tissue 215 at the end of the low intensity interval of the first oscillation illustrated in FIG. 30B. In FIG. 31A, layer 212 is the spongy layer and layer 213 is the compact layer. Due to the receding of the fluid boundary 220 during the low intensity interval, however, some pores of the spongy layer between these two distances fill with blood and other fluids. The blood and the fluids may enter into the spongy layer pores 232 from compact layer 213 or from the deeper tissue layers through compact layer 213. Spongy layer 212 pores that are above the fluid boundary 220 do not fill with any fluids because the heat flux is sufficient here to vaporize fluids even during the low intensity interval.

Figure 30C:
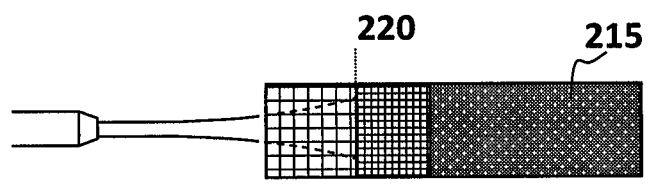

Turning to FIG. 30C, once a suitable thickness of compact layer 213 has been formed by low intensity plasma 211, a second high intensity plasma burst 210 is directed at the tissue. As shown in FIG. 30C, spongy layer 212 increases in thickness by another pore diameter due to vaporizing fluid in tissue that was previously a part of compact layer 213. As a result, the thickness of the compact layer is reduced. This reduction is partially offset by a slight increase in compact layer thickness as some of the protein in the tissue below the compact layer tissue denatures.

FIG. 31B shows the surface region of tissue 215 after the high intensity plasma flow in the situation depicted in FIG. 31A. FIG. 31B corresponds to FIG. 30C. In addition to advancing the fluid boundary deeper into the tissue, the high intensity plasma has evaporated the fluid component of blood 232 (shown in FIG. 31A), which was present in the pores of spongy layer 231. Solid component 233 of the blood has been left behind, adding to the tissue-based solid component of the spongy layer. This extra solid component increases the density of the spongy layer and improves its sealing capability. Additionally, as discussed above, the high intensity plasma of the second oscillation sublimated approximately one pore diameter of the spongy layer.

Figure 30D:
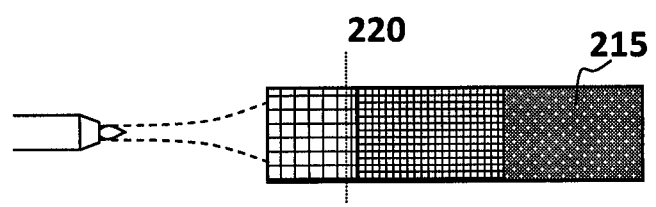
Figure 30E:
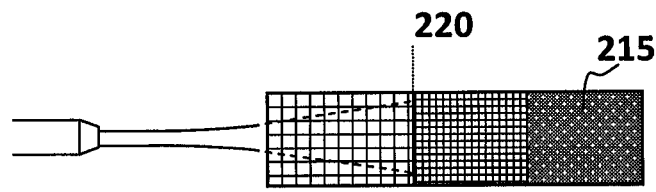
Figure 30F:
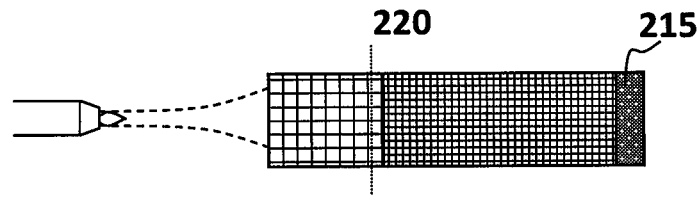

FIG. 30D shows the low intensity interval of the plasma flow of the second oscillation. The effects of this low intensity plasma on the tissue are similar to the first low intensity interval described in FIG. 30B. Again, blood may flow into part of the spongy layer because the fluid boundary recedes to a level closer to the surface. Even if the fluid boundary recedes, this flow of blood into the spongy layer will typically be slower than during the low intensity interval of the first oscillation. This is due to the significant increase in the compact layer thickness that occurred as heat was provided to the underlying tissue. In general, until a given spot has been fully coagulated less blood and other fluids flow into the spongy layer during each subsequent low intensity interval. FIGS. 30E and 30F show the high and low intensity portions of the third oscillation in the plasma flow, respectively, which have effects on the tissue similar to the earlier oscillations.

FIG. 32 shows a completed a sealing layer formed by an axially oscillating plasma flow. Spongy layer 240 is composed of several sublayers. Each sublayer was formed by a high intensity plasma burst. In contrast, a spongy layer formed with a continuous plasma flow does not have such a multilayer structure. For the cases in which the fluid boundary recedes during the low intensity intervals, the density of the spongy layer generally increases toward the surface. This is due to the presence of red blood cells that remain in the spongy layer after the blood that flows into the spongy layer during the low intensity intervals evaporates, leaving additional solid components.

The end result of applying an axially oscillating plasma flow to bleeding tissue is the formation of a strong and robust sealing layer through the alternating process described above. In general, in a single axial oscillation of the plasma flow, spongy layer tissue is rapidly formed during the high intensity interval while compact layer is formed during the low intensity interval.

The discussion so far has focused on the coagulation of a single spot. In practice, the operator must coagulate an area of tissue greater than the spot diameter. To do this, the operator sweeps the surgical site with the plasma flow by moving the plasma-generating device parallel to the tissue surface. FIG. 33A shows surgical site 270 covered with blood 273. Blood 273 obscures the surgical site and the bleeding must be stopped before the operator can resume the surgical procedure. In a preferred embodiment, the operator sweeps across the surgical site 270 along an exemplary path 271 shown in FIG. 33B. As the plasma flow passes over any particular position, several oscillations of the plasma flow occur and form a sealing layer in the tissue as described with reference to FIGS. 30A-F.

FIG. 34A-C show the effect of such a plasma flow as it sweeps along exemplary path 271. Plasma flow 280 moves along tissue 281 at a rate slow enough to ensure that a sealing layer of appropriate thickness is generated at each position. As discussed above, spongy layer 282 is preferably 250 μm thick and compact layer 283 is preferably at least 200-500 μm thick. For a typical tissue with a pore diameter of 30 μm, a 250 μM thick spongy layer requires approximately 8 high intensity pulses (each pulse forms approximately one pore diameters of spongy tissue). Each spot of tissue 281 should therefore be subjected to 8 oscillations of the plasma flow in order to generate the appropriately thick spongy layer.

FIG. 35 shows a more realistic situation where the bleeding rate in the tissue varies over a single surgical site, indicated by the relative size of the arrows 290 and 291 in tissue 281. Spots with lower levels of bleeding can be coagulated with a thinner sealing layer. This is preferable because less healthy tissue is destroyed to form the sealing layer. In practice, the operator can sweep the plasma flow quickly over surgical site 270 to create a thin sealing layer. This thin sealing layer coagulates areas of low bleeding 290 but areas of high bleeding 291 continue to bleed. This quick sweep may result in, for example, 5 high intensity pulses per spot diameter. Once this thin sealing layer is established, the operator focuses on areas of high bleeding 291, where continued exposure to the plasma flow creates a thicker sealing layer. This alternative method ensures that the sealing layer is of the appropriate thickness at each spot of the treated surface. This variable thickness sealing layer is shown in FIG. 35, where spongy layer 282 and compact layer 283 are thick in areas of high bleeding 291 but are thin in areas of low bleeding 290.

The rate of sealing layer formation may vary with variations of the distance between the plasma-generating device and the tissue. Ideally, the operator holds the plasma-generating device at a constant distance from the tissue as he sweeps along exemplary path 271 shown in FIG. 33B. In reality, the operator may not be able to keep the plasma-generating device perfectly level throughout the procedure. Therefore, to account for operator hand movements, it is important that the coagulation effect does not change substantially with distance over a suitable range. FIG. 36 shows the temperature of a plasma flow along the plasma flow axis during both the high intensity portion and the low intensity portion of a volumetrically oscillating plasma flow. Region 313, where the temperatures of both the high and low intensity plasma are substantially constant, is ideal for performing coagulation. This region corresponds to approximately 10-30 mm when the high intensity plasma has an outlet temperature of 20,000-30,000 K and the low intensity plasma has an outlet temperature of about 11,000 K. During coagulation the operator maintains this distance, within the range of 10-30 mm, preferably 15-25 mm, ensuring that the coagulation effect does not vary significantly despite unavoidable movement.

The speed that an operator can coagulate an area of bleeding tissue also depends on the spot diameter. FIG. 37 shows the required path 272 that a plasma flow with a relatively small spot diameter would have to travel in order to achieve coagulation in tissue 270. If the spot diameter at the distance of 10-30 mm is relatively small, coagulation of a surgical site takes too long and is not feasible. For this reason, prior art coagulation devices had large outlet diameters, in the range of 0.8-1.2 mm. Such large diameters are acceptable, and may be even preferred, when the plasma-generating device is only intended to be used for coagulation, but are too large to be used for cutting. An axially oscillating plasma flow, however, has an increased width compared to a continuous plasma flow, as explained above with reference to FIGS. 22A-D. For an axial oscillation, disturbances in the airflow surrounding the plasma flow cause the plasma flow spot diameter to increase. This allows a plasma-generating device with a small outlet diameter to generate a volumetrically oscillating plasma flow with a relatively large spot diameter suitable for coagulation. For example, in a preferred embodiment with a 0.5 mm diameter outlet, at the preferred distance of 10-30 mm the spot diameter may reach 5-6 mm. To achieve the same spot diameter with a continuous plasma flow, an outlet diameter of 1.2 mm would be required.

In a preferred embodiment, when the plasma-generating device is programmed to operate in coagulation mode, the characteristics of an axially oscillating plasma flow (e.g. the duty cycle, frequency, and temperature) are optimized to achieve efficient coagulation. As shown in FIG. 20B, the plasma flow alternates between high intensity plasma and low intensity plasma. The characteristics of the high and low intensity plasma agree with mathematical models of the coagulation processes and were also confirmed experimentally.

Principal processes in tissue coagulation include spongy layer and compact layer formation. Spongy layer formation can be modeled with the following equation:

$$q_f = (u_f + u_b) \times \rho L,$$

where $q_f$ is the heat flux required at the fluid boundary in W/mm², $u_f$ is the velocity of the fluid boundary as it moves inward in mm/s, $u_{blood}$ is the blood flow rate in mm/s, $\rho_{tissue}$ is the density of the tissue in kg/mm³, and L is the energy required for vaporization in J/kg. The density $\rho_{tissue}$ and the vaporization energy L can be approximated with the density and vaporization energy of water (10³ kg/m³ and 2.26×10⁶ J/kg, respectively). The velocity $u_f$ can be rewritten as $$u_f = \frac{d}{t_H},$$

where d is the desired thickness of the spongy layer formed in one high intensity burst in mm, and $t_H$ is the high intensity interval in s. As discussed above, d is preferably one pore diameter $d_P$. The equation for the heat flux required at the fluid boundary can therefore be rewritten as $$q_v = \left(\frac{d_p}{t_H} + u_b\right) \times \rho L.$$

FIG. 38 shows the graph of vaporization heat flux $q_f$ plotted for three different bleeding rates as a function of $t_H$. As seen from FIG. 38, the bleeding rate has a much stronger influence on the required heat flux for longer high intensity pulses. For example, for a high intensity interval of 8 ms, the difference in vaporization heat flux $q_f$ is 40%, when the blood flow rate changes from 1 mm/s to 3 mm/s.

To ensure coagulation of tissues with different bleeding rates, the plasma flow must provide the heat flux required to stop the highest bleeding rate. Referring back to FIG. 38, the plasma flow must provide at least 16 W/mm² to stop bleeding with a rate of 3 mm/s when $t_H$ is 8 ms. If such a plasma flow is directed at tissue with a lower bleeding rate of 1 mm/s, there will be excessive heating of the spongy layer, which may result in significant undesired sublimation. Because, as mentioned above, the bleeding rate may vary significantly over the surgical site, this problem occurs as the operator is coagulating different spots on the same tissue. Keeping the high intensity interval short eliminates this problem. For example, if the high intensity plasma burst is only 1 ms long, the required heat flux varies only 5% between bleeding rates of 1 mm/s to 3 mm/s. Therefore $t_H$ is preferably kept low. Additionally, exposing tissue to shorter high intensity bursts, such as 1 ms, avoids pyrolysis and charring because such a short duration, while sufficient to vaporize fluids, is not sufficient for the pyrolysis reaction to begin.

FIG. 38 also shows that if $t_H$ is very short, i.e. less than 1 ms, the heat flux required to form one pore diameter of spongy tissue becomes extremely high. And because $q_f$ is the heat flux required at the fluid boundary, the corresponding heat flux at the surface $q_{surface}$ is even higher. Accordingly the high intensity interval is preferably about 1 ms.

The compact layer is formed by heat diffusion across the fluid boundary into the underlying tissue. Compact layer formation depends primarily on the duration of the applied low intensity plasma. This heat diffusion process can be modeled by the Bio-Heat diffusion differential equation:

$$\rho C \frac{\partial T}{\partial t} = k \nabla^2 T + h_m + h_b,$$

where $\rho$ is the tissue density in kg/mm³, C is the specific heat of the tissue in J/kg·K, $h_m$ is the rate of metabolic heat production per unit volume of tissue and $h_b$ is the rate of heat transfer between blood and tissue per unit volume of tissue in J/kg·s. The rate of metabolic heat production $h_m$ is so much lower than the heat flux from the plasma flow that it can be ignored, and the rate of heat transfer between blood and tissue $h_b$ can be expressed by:

$$h_b = \rho_{blood} C_{pb} \omega (T_a - T),$$

where $\rho_{blood}$ is the density of blood (approximately 1050 kg/m³), $C_{pb}$ is the heat capacity of blood (which is around 3,600 J/kg·K), $\omega$ is the blood perfusion (which is on the order of 1-10 s⁻¹), and $T_a$ is the temperature of the arterial blood flowing into the volume (which is approximately 36.6° C.).

Using this equation it is possible to calculate the thickness of the compact layer formed as a function of time. These calculations can provide guidance on the optimal duration of the low intensity interval of the plasma flow. For short times, the solution of the above equation yields the following analytical approximation:

$$h = 20 \times \sqrt{t_L},$$

where h is the thickness in μm and $t_L$ is the duration of the low intensity interval of an oscillation (in s). FIG. 39 shows this short time approximation plotted alongside the numerical simulation of compact layer formation as a function of $t_L$. It is clear from FIG. 39 that there is a substantial agreement between the two curves for times less than 70 ms. As mentioned above, preferably two to four pore diameters of compact layer are generated in a single period of oscillation. At the lower limit, it takes at least 10 ms to produce a compact layer of two pore diameters (assuming 30 μm pores).

The rate of compact layer creation drops off as time increases. This rate is expressed as a derivative of h:

$$h' = \frac{10}{\sqrt{t_L}}.$$

FIG. 40 shows the rate of compact layer formation as a function of $t_L$. As seen from FIG. 40, for $t_L$ greater than 60 ms the rate of compact layer formation is less than the minimum bleeding rate in tissue, which is assumed to be 1 mm/s. Accordingly, application of the low intensity plasma flow beyond 60 ms does not form additional compact layer. Therefore, the low intensity interval should be 10-60 ms, and is preferably 15-35 ms.

Based on these biological considerations as well as other requirements, it is possible to determine the optimal characteristics of an axially oscillating plasma flow generated with a low frequency biased pulse wave current. From device requirements, the preferred duty cycle D of 0.05-0.15 ensures that the average current remains low while still achieving a high peak current. The high current level $I_H$ is preferably 30 A and the preferred low current level is 6 A. Using such a current wave, the preferred volumetrically oscillating plasma flow oscillates between the preferred low temperature of at least 11,000 K and the preferred high temperature of 20,000-30,000 K.

To produce plasma flows suitable for multiple surgical tasks, such as coagulation cutting, and vaporization, the outlet diameter is preferably 0.5 mm. With this preferred outlet diameter, an axially oscillating plasma flow adapted for coagulation has a spot diameter of 5-6 mm when the device is held 15-25 mm from tissue. Under these circumstances coagulation in the affected spot is accomplished in 250-400 ms. The time of human reaction is approximately 200-300 ms. This means that the operator does not need to focus on coagulating a given spot. The operator can move the device without regard to the speed with which he does, while accomplishing reliable coagulation.

As determined above, when examining the formation of the spongy layer, each tissue spot requires 8 high intensity plasma bursts to form the minimum thickness of the spongy layer. To ensure the delivery of 8 pulses to a given spot, the frequency of at least 20 Hz, which is the preferred lower limit for longitudinal volumetrically oscillating plasma flows for coagulation, should be used. For a wave with a frequency of 20 Hz with a duty cycle D of 0.05-0.15, the period τ of 50 ms and a high intensity pulse interval $t_H$ of 2.5-7.5 ms. This is the minimum frequency at which coagulation is reliable with an axially oscillating plasma flow generated using a low frequency biased pulse wave current. In the preferred embodiment, the biased pulse wave current has a frequency of 40 Hz with a duty cycle D of 0.05-0.15, it has a period τ of 25 ms and a high intensity pulse interval $t_H$ of 1.25-3.75 ms.

An upper boundary on the frequency can be found by examining the amount of compact layer tissue formed in 8 oscillations of the plasma flow. FIG. 41 shows a plot of the compact layer thickness as a function of the number of oscillations for several different frequencies. The thickness of the compact layer should be 200-500 μm. Using the minimum thickness as a boundary condition, the frequency of plasma oscillations is preferably less than 70 Hz. A volumetrically oscillating plasma flow generated by a current wave with a frequency of 70 Hz with a duty cycle D of 0.05-0.15 has a period τ of 14 ms and a high intensity interval $t_H$ of 0.7-2.1 ms. If the frequency is increased above this preferable upper boundary, the thickness of the compact layer is insufficient for coagulation.

When coagulating tissue, severed blood vessels must also be sealed to fully stop bleeding. In some organs, vessel blood flow rate may approach 30 mm/s. FIG. 42 shows blood vessel 275 having blood vessel wall 274, which exposed through the process of coagulation. These blood vessels can be sealed by heating the inside walls of the exposed blood vessel, as disclosed in U.S. application Ser. No. 12/696,411 incorporated by reference herein for all purposes. This heating causes collagen in blood vessel wall 274 to denature and swell inward, closing off the blood vessel 275. For small blood vessels (less than approximately 1 mm in diameter) heating the tissue surface is sufficient to seal the blood vessels. Sealing larger blood vessels requires heating of the blood vessel walls to depth of 1-1.5 blood vessel diameters. Heating to this depth can only be accomplished using a plasma flow if the plasma flow has a high dynamic pressure directed into the blood vessel. A continuous or axially oscillating plasma flow with an outlet temperature greater than 11,000 K can provide a dynamic pressure along the plasma flow axis meeting this criteria. At this temperature, the plasma has enough energy and velocity to vaporize blood, penetrate into the blood vessel to the required depth, and heat the blood vessel walls from the inside. In a preferred embodiment, the volumetrically oscillating plasma flow, even during the low intensity interval, has an outlet temperature of over 11,000 K, and is therefore suitable for sealing large blood vessels, as disclosed in U.S. application Ser. No. 12/696,411.

FIGS. 43A-C show the application of an axially oscillating plasma flow to seal a blood vessel. In FIG. 43A plasma flow 320 has been directed into an exposed blood vessel. Blood 321 has been vaporized to a depth of 1-1.5 blood vessel diameters. Plasma flow 320 heats the exposed blood vessel walls 322 with which it comes in contact. FIG. 43B shows exposed blood vessel walls 322 swelling inwards toward each other. After enough swelling has occurred, walls 322 completely seal the blood vessel and stop blood 321 from flowing to surface. This swelling may not completely occlude the vessel, particularly if the diameter of the vessel is relatively large i.e., greater than 3 mm. In this case, the operator sweeps the tissue surrounding the contracted vessel with the plasma flow in a circular motion. This heats the surrounding tissue, which also swells and forces the blood vessel walls to completely occlude the vessel.

5.4.1.3 Coagulation with Modulated Plasma Flows

In another embodiment, high frequency oscillations are introduced during the high intensity interval of an axially oscillating plasma flow. This volumetrically oscillating plasma flow is generated by the modulated biased pulse current wave, an example of which is shown in FIG. 12. Like the embodiment using the low frequency biased pulse wave shown in FIG. 11, this plasma flow is also specially suitable for coagulation. By maintaining the same bias current level $I_L$, pulse current level $I_H$, low frequency, and low frequency duty cycle as the low frequency biased pulse wave, this embodiment also produces a plasma flow with axial oscillations that efficiently accomplish coagulation, as described above. The high frequency oscillations, which produce radial oscillations during the high intensity interval of the plasma flow, occur with a frequency greater than 2,000 Hz, preferably greater than 20,000 Hz. The duty cycle of high frequency oscillation is 0.35-0.65, preferably 0.5. For the high frequency oscillations of 2,000 Hz with a duty cycle D of 0.35-0.65 the period τ is 0.5 ms and a high intensity pulse interval $t_H$ of 175-325 μs. A high intensity pulse interval corresponding to 20,000 Hz and D of 0.35-0.65 is correspondingly 17.5-32.5 μs. The duty cycle D of 0.36-0.65 ensures that the length of the plasma does not decrease between high frequency bursts. In other words, the length of the plasma flow is kept at its expanded state during the high intensity interval. If the high frequency oscillations are ultrasonic, these high frequency oscillations improve the coagulation effect by additionally providing ultrasonic pressure waves to the tissue.

Ultrasonic pressure waves, such as those provided by a plasma flow operating at a high frequency, have at least two effects on tissue. These effects are observable when the frequency of oscillations is greater than 20 kHz. First, acoustic vibrations at this frequency generate heat. This vibration heat is, however, negligible compared to the heat provided by the plasma flow itself at outlet temperatures of 11,000 K and above. Second, and more important for coagulation, the nature of heat transfer to the compact layer changes in the presence of cavitation. Specifically, plasma that does not oscillate ultrasonically heats the compact layer by diffusing heat into the tissue from the fluid boundary. In contrast, plasma utilizing ultrasonic oscillations has an additional cavitation mechanism for heating the tissue. Cavitation refers to the action of the ultrasonic pressure waves on gas bubbles in a liquid. As explained above, the oscillations of the plasma flow result in acoustic oscillations, which are pressure waves. When pressure waves act on a liquid, bubbles of gas can form in the liquid when the pressure drops below the characteristic vapor pressure of that liquid. When the pressure waves are ultrasonic, these bubbles oscillate violently and then implode creating powerful localized shockwaves. These mechanisms rapidly heat the surrounding blood and tissue. Cavitation results in faster compact layer formation and improved coagulation.

FIG. 44 shows the effect of an ultrasonic pressure wave on the size of a bubble. FIG. 44 is a plot of the bubble size as a function of time. Interval 331 corresponds to the formation of the bubble during a low pressure wave front of the ultrasonic wave. The bubble expands when the pressure drops and contracts when the pressure increases. Interval 332 shows the bubble contracting during the following high pressure wave. The bubble alternates between expansion and contraction, but expands faster than it contracts. When the ultrasonic pressure wave is generated by high frequency oscillations of a plasma flow, the cycles of expansion and contraction follow the high frequency oscillations. The expansion and contraction of bubbles creates localized fluid flow. These localized fluid flows can have high velocities and shear stresses great enough to destroy cells and other cellular structures in a tissue.

At high ultrasonic intensities the bubble shown in FIG. 44 will implode after a few oscillation cycles. During implosion, very high shear stresses, shock waves, pressures, and temperatures are produced. The result of these explosions is the destruction and fragmentation of the local structure of the tissue. Additionally, the heat generated from the shear stresses and bubble collapses can denature protein and increase the rate of coagulation.

Because plasma is an ionized gas, there are important synergetic effects when ultrasonic energy is coupled with a plasma flow to achieve coagulation. As the plasma flow passes through the spongy layer of a tissue it impacts the fluid boundary. Some of the plasma passes into the tissue below the spongy layer as dissolved gas. This increased amount of dissolved gas then forms bubbles which act as receivers of ultrasonic energy and cavitate. The result of combining a high-temperature plasma with ultrasound is that the cavitation effect is greatly enhanced, which improves coagulation.

Morphological samples show that when ultrasonic oscillations are used during coagulation, the compact layer has two distinct sublayers. The sublayer adjacent to the spongy layer is a dense homogeneous layer with all cell structure destroyed due to cavitation. The sublayer below is the regular compact layer as described above. The resulting sublayer of the compact layer formed as a result of cavitation is a dense homogenous layer that shows improved sealing characteristics. Also, a spongy layer formed from tissue that has been disrupted by cavitation has a significantly reduced pore size, ranging from 20-25 µm rather than 30-70 µm.

The addition of ultrasound is also beneficial for sealing bleeding blood vessels. Cavitation occurring in the vessel walls and blood inside of the vessel accelerates the sealing process. Destruction and fragmentation of the vessel tissue greatly enhances the swelling process which forms the seal of the blood vessel. It has been observed that the addition of ultrasonic high frequency oscillations increase the swelling of blood vessel walls by up to five times and greatly speed up the sealing process. Accordingly, even large blood vessels with a high blood flow rate can be sealed rapidly without a need to direct the plasma flow into the blood vessel and then at the surrounding tissue for an extended period of time.

Accordingly, in this preferred embodiment, where a volumetrically oscillating plasma flow is generated by a modulated biased pulse current wave, the operator simply sweeps the tissue with the plasma flow without regard to the nature of the tissue and the presence of the blood vessels. The improved coagulation properties for such a plasma flow facilitate the rapid sealing of the blood vessels without spending extra time directing the plasma flow into the vessel. No special attention needs to be paid to blood vessels, as even large blood vessels with a blood flow rate of 30 mm/s are sealed rapidly by this sweeping process.

5.4.2 Cutting with Radially Oscillating Plasma

Beyond tissue coagulation, plasma flows can also be used to accomplish the surgical task of cutting. During this surgical task a small region of tissue is destroyed in order to separate the tissue. By separating the tissue, the operator can remove unwanted tissue or expose underlying tissues for further surgery. For coagulation as described above, certain thermal and mechanical effects were accomplished in the tissue while avoiding significant sublimation. When cutting using a plasma flow, however, sublimation of the tissue is intended. In the preferred embodiments sublimation is accompanied by the simultaneous coagulation of the just-separated tissue. This simultaneous coagulation is accomplished by the use of a volumetrically oscillating plasma flow. Using the preferred embodiments, even tissues with characteristically high bleeding rates can be cut without significant bleeding or without any bleeding.

As an overview, prior art continuous plasma flows have been used to accomplish cutting. A typical plasma flow suitable for cutting had a significant axial component of the dynamic pressure and provided a high heat flux. A thin cut was achieved by using a plasma-generating device with a small outlet diameter. By keeping the cut thin, tissue damage was limited to a very small region of the tissue and the precision of the cut was high. Coagulation effects, such as the formation of spongy and compact layers, were negligible. The result of using a continuous plasma flow for cutting was a thin, precise cut which bled significantly. The bleeding tissue exposed by this cut would typically be coagulated using a separate device.

FIGS. 45A-C illustrate the process of cutting with a typical prior art continuous plasma flow. Plasma-generating device 340 is placed at the surface 341 of the tissue. By keeping plasma-generating device 340 adjacent to the surface of the tissue, the surface of the tissue is in cutting region 311 as shown in FIG. 36. Referring back to FIG. 45A, plasma flow 342 vaporizes a portion of the tissue, forming a cut. The cut has walls 343 which are tissue exposed due to the destruction of adjacent tissue. Because the radial component of dynamic pressure in a continuous plasma flow is negligible, walls 343 are not coagulated by the continuous plasma flow and begin to bleed. At the bottom of the cut a thin sealing layer consisting of spongy layer 344 and compact layer 345 is formed. However, due to the very high heat flux provided by the plasma flow, this sealing layer translates inward rather than increasing in thickness.

To lengthen the cut, plasma-generating device 340 is moved along the surface of the tissue to form a groove. To cut to a greater depth or completely separate the tissue into separate pieces, plasma-generating device can be moved deeper into the cut to sublimate more tissue. This is shown in FIG. 45B. Additionally, during the cutting process blood vessels 346 are dissected by the plasma flow and their exposed ends open into the cut. Importantly, a continuous plasma flow used for cutting does not efficiently coagulate the tissue or blood vessels exposed along the walls of the cut. Tissue bleeding 347 and vessel bleeding 348, shown in FIG. 45C, must be coagulated in some other way, such as a separate plasma flow adapted for coagulation or by some other means.

By using a radially oscillating plasma flow, cutting can be accomplished while simultaneously coagulating tissue exposed by the cut, resulting in a cut with little to no bleeding. In the preferred embodiment, a high frequency biased pulse wave of current is used to generate a plasma flow with substantial radial oscillations. The frequency of the oscillations is greater than 2,000 Hz, and is preferably 20,000-30,000 Hz. In one embodiment, the biased pulse wave current has a frequency of 20,000 Hz with a duty cycle D of 0.05-0.15, it has a period $\tau$ of 50 µs and a high intensity pulse interval $t_H$ of 2.5-7.5 µs. An example of such a plasma flow is depicted in FIG. 20A. At such a high frequency, the scattering of plasma particles directs plasma both axially and radially. The radially directed plasma creates a substantial radial component of the dynamic pressure and heat flux. These substantial radial components, unique to volumetrically oscillating plasma flows, are used to coagulate the tissues along the walls of the cut as the cut is made. Additionally, because the high intensity interval of the high frequency pulses is not long enough for the plasma flow to extend to a significant length, the energy of the plasma flow, even during the high intensity interval, is concentrated in a volume near the outlet of the plasma-generating device.

This concentration of energy is apparent FIGS. 18A-B. The volume of active plasma tapers to a point on the plasma flow axis, which can be considered the "cutting tip" of the plasma flow. Because of the very focused cutting tip, the resulting cut formed by the radially oscillating plasma flow will be thin and minimize the amount of tissue destroyed. This cutting tip is present for both high and low intensity plasma.

A radially oscillating plasma flow accomplishes both the sublimation and coagulation of tissue simultaneously. FIGS.

46A-C illustrate the cutting process (both sublimation and coagulation of tissue) with a radially oscillating plasma flow. Turning first to the cutting aspect of the process, FIG. 46A shows a high intensity flow 350 is directed from plasma-generating device 351 during the high intensity interval of the high frequency biased pulse current wave. Plasma-generating device 32 is positioned at the tissue surface. The high intensity plasma, which has an outlet temperature of 20,000-30,000 K, sublimates tissue to form a cut. Because the high intensity plasma with the outlet temperature of 20,000-30,000 Hz is maintained for just a few μs, it does not cause extended damage to the tissue. The high intensity plasma has a heat flux directed both axially and radially, so that the width of the cut corresponds to the maximum width of the plasma flow, which is may be as high as 1.5 mm plasma is relatively wide of the outlet with the diameter of 0.5 mm.

FIG. 46B shows a subsequent low intensity interval of the plasma flow following the high intensity pulse shown in FIG. 46A. The low intensity plasma has the outlet temperature of at least 11,000 K and a heat flux a distribution with a significant axial component and a relatively small radial component. This ensures that during the low intensity interval, no radial sublimation of tissue occurs. The low intensity plasma advances the cut further in the axial direction, deepening it. Accordingly, both high intensity and low intensity plasma provide contribute the tissue cutting.

As to coagulation, as shown in FIG. 46A, the radial oscillations create a coagulation effect in all directions similar to the effect the axial oscillations have in the axial direction for tissue coagulation. Specifically, during a high intensity interval, the heat flux radial component of the plasma flow creates spongy layer 353 in the walls of the cut. At the same time, the heat flux axial component of the plasma flow creates spongy layer 353 along the bottom of the cut. Additionally, the high intensity plasma burst begin to forms compact layer 354 as heat defuses past spongy layer 353. By the end of the high intensity interval, compact layer 354 is relatively thin because the interval is short compared to the time required for significant heat diffusion from the fluid boundary 355. Accordingly, only a very small thickness of tissue below the spongy layer has a substantial amount of denatured protein.

As shown in FIG. 46B, during the subsequent low intensity interval, low intensity plasma 352 provides a lower heat flux to the tissue in the walls of the cut. This lower heat flux increases the thickness of compact layer 354 without causing further sublimation of spongy layer 353 in the walls of the cut. After a number of volumetric oscillations, the walls of the cut are completely coagulated. The result is shown in FIG. 46C, where the tissue has been completely separated while at the same time a thick sealing layer comprising spongy layer 353 and compact layer 354 completely prevents bleeding.

When the frequency of oscillations is ultrasonic, the coagulative effect of a volumetrically oscillating plasma flow on a tissue is improved by the addition of ultrasonic energy. As described in reference to the surgical task of coagulation, this ultrasonic energy acts as an extra source of heating and causes cavitation in the tissue. Cavitation which occurs at the tissue surface aids the surgical task of cutting by disrupting the tissue at the surface and causing fragmentation. This cavitation, in addition to the sublimation, results in an enhanced cutting efficiency.

To briefly review, in the surgical task of coagulation the addition of ultrasonic energy results in a greatly improved sealing layer. Likewise, ultrasonic energy dramatically improves coagulation during the surgical task of cutting. First, rapid heating of tissue below the fluid boundary via the cavitation mechanism speeds up the denaturation reaction that forms the compact layer. This means that compact layer formation, which is slow compared to spongy layer formation, is greatly sped up. Second, tissue disruption due to ultrasonic cavitation has many beneficial effects on the strength of the sealing layer. Spongy layer pore diameters, for example, are significantly decreased, which makes this layer denser and better at stopping blood flow. Cavitation also creates a sublayer of the compact layer in which the cells themselves have been disrupted, creating a more homogenous structure which is better at stopping blood flow. The result of these effects is that the sealing layer can be made significantly thinner while at the same time being significantly better at stopping bleeding.

With regards to blood vessels dissected during the cutting process, FIG. 47 shows how the radial heat flux component of a radially oscillating plasma flow can seal blood vessels. As discussed in the case of coagulation, penetration of plasma into blood vessels requires the plasma to have a low density and a high dynamic pressure directed into the blood vessel. Because high intensity plasma 360 has a large dynamic pressure with a significant radial component, it is able to provide a large dynamic pressure 361 into blood vessel 362. The high intensity plasma is capable of penetrating into blood vessel 361 and heating exposed blood vessel walls 363 to create the sealing effect described in reference to FIGS. 43A-C.

Cavitational effect due to ultrasonic waves generated as a result of radially oscillating are capable of completely occluding the severed vessel openings as the cutting continued to be performed to ultrasonic oscillations. Similar to the surrounding tissues, the blood vessel walls and blood are disrupted and coagulated by the ultrasonic acoustic wave. The cavitational effect works in conjunction with the penetration of the plasma into the vessel to accomplish vessel sealing.

Because of the benefits associated with ultrasonic acoustic waves, in the preferred embodiment for the surgical task of cutting the frequency of oscillations is ultrasonic. The volumetrically oscillating plasma flow is preferably generated using a high frequency biased pulse wave oscillating with a frequency of 20,000-30,000 Hz. In this preferred embodiment, the bias current level is 6 A, the pulse current level is 30 A, and the duty cycle is 0.05-0.15.

Results in animal testing have shown that effective coagulation can be coupled with the surgical task of cutting using the preferred embodiment. Tissues with very intensity characteristic bleeding rates have been cut without any significant, or any, bleeding. Additionally, vessels with diameters as large as 4 mm have been sealed as they were cut.

5.4.3 Vaporization with Radially Oscillating Plasma

In addition to the surgical tasks of coagulating and cutting, a plasma flow can also be used to accomplish the surgical task of vaporization. Like cutting, the primary goal of vaporization is the destruction of tissue. In cutting, a small amount of the tissue was destroyed to separate pieces of tissue from each other. In vaporization, on the other hand, a certain amount of unhealthy or otherwise undesirable surface tissue is destroyed. In such a situation, the goal is to completely destroy the undesirable tissue while causing as little collateral damage as possible. This collateral damage includes incidental vaporization of adjacent healthy tissue and bleeding from the tissues exposed during vaporization. For example, cancerous tumor nodules situated on a tissue that must be preserved such as on the spinal cord, brain, or ovaries may need to be vaporized rather than excised to protect the delicate tissue beneath.

An ideal plasma flow for vaporization should provide precise control of the depth of tissue vaporization while at the same time efficiently coagulating the tissue exposed during vaporization. A radially oscillating plasma flow can be used for this purpose. In fact, the same radially oscillating plasma flow preferred for the surgical task of cutting is also preferred for the task of vaporization. That is, the volumetrically oscillating plasma flow is generated using a high frequency biased pulse wave current having a frequency greater than 2,000 Hz, preferably 20,000-30,000 Hz. The duty cycle of the volumetrically oscillating plasma flow is preferably 0.05-0.15, the bias current is 6 A, and the pulse current is 30 A. A radially oscillating plasma flow generated with this high frequency biased pulse current wave was discussed with reference to FIG. 20A. In this case, short high intensity intervals limit the length of the plasma flow unlike concentrating energy close to the outlet of the plasma-generating device. Additionally, as described above with reference to cutting, such a volumetrically oscillating plasma flow is optimized to efficiently coagulate tissue exposed after vaporization of the surface. If the frequency of oscillations is ultrasonic, ultrasonic energy is also provided to the tissue, which improves both vaporization and coagulation, as described above with reference to cutting.

While the preferred volumetrically oscillating plasma flow is the same for cutting and vaporization, the procedure for performing the task differs. In cutting, the device is held at the surface of the tissue, i.e. 0 mm from the outlet to the tissue. This position maximizes the amount of tissue vaporization and speeds up the cutting process. In vaporization, on the other hand, precise control of the depth of destruction is required. FIG. 36 shows that the optimal distance for the task of vaporization is in region 312. Preferably, plasma-generating device 32 is held at a distance of 2-5 mm from the surface of the tissue. Because the temperature drops rapidly over this region, the operator has good control of the rate of vaporization by simply moving the device towards or away from the tissue surface.

Figure 48C:
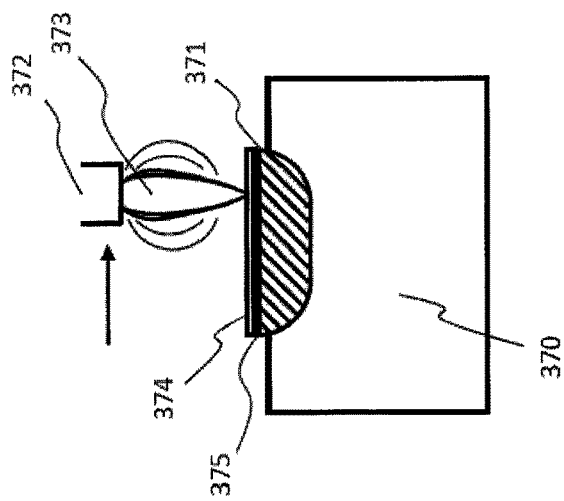
Figure 48B:
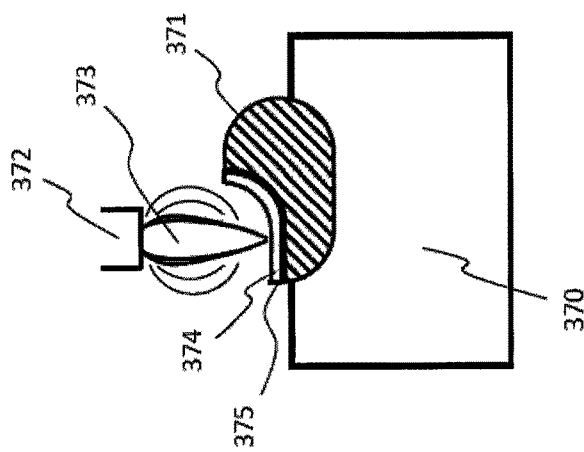
Figure 48A:
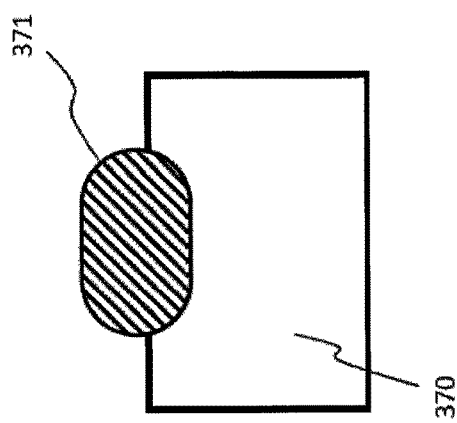

FIGS. 48A-E show the vaporization of a tumor according to the preferred embodiment. FIG. 48A shows tumor 371 growing on the surface of healthy tissue 370 before the application of the radially oscillating plasma flow. The goal of the procedure is to completely destroy all of the undesired tissue of tumor 371 while simultaneously coagulating the underlying tissue. In FIG. 48B, plasma-generating device 372 has produced radially oscillating plasma flow 373 and is directed at a part of tumor 371. Plasma-generating device 372 is held between 2-5 mm from the surface of tumor 371. The operator adjusts the distance of plasma-generating device 372 to maintain a controlled and steady rate of vaporization. While plasma flow 373 is directed at tumor 371, multiple oscillations of the plasma flow occur. During high intensity intervals, high intensity plasma accomplishes both sublimation of tumor tissue and rapid formation of spongy layer 374. During low intensity intervals, the low intensity plasma also accomplishes sublimation of tumor tissue. Due to its lower temperature and heat flux, the rate of sublimation achieved by the low intensity plasma is much lower than the rate achieved by the high intensity plasma. However, the low intensity plasma is applied for 8.5-20 times longer than the high intensity plasma, so significant sublimation may be accomplished even with the lower rate. So substantial sublimation occurs even during the low intensity interval. Besides sublimation, the low intensity plasma also provides heat to the compact layer through the process of heat diffusion from the fluid boundary. This alternating process of coagulation, where the high and low intensity plasma work together to efficiently form a sealing layer, was described above with respect to both coagulation and cutting. By the time the operator moves plasma-generating device 372 laterally to the position shown in FIG. 48C, the radially oscillating plasma flow has vaporized part of tumor 371 and simultaneously formed a sealing layer to prevent bleeding.

FIG. 48C shows tumor 371 after several oscillations of plasma flow 373 have been directed at another part of the tumor. Typically, the operator moves plasma-generating device in a circular motion parallel to the surface of tissue 370 so that the entire tumor is vaporized at a controlled and even rate. At this time, the top portion of tumor 371 has been destroyed, but some undesired tissue remains embedded in healthy tissue 370. At this point in the procedure, the operator may optionally remove plasma-generating device 372 and determine if tumor 370 has been completely destroyed. One way to determine if the tumor has been completely destroyed by visual or tactile examination. If the tumor is still present, it will have a noticeably different texture than healthy tissue 370.

Figure 48E:
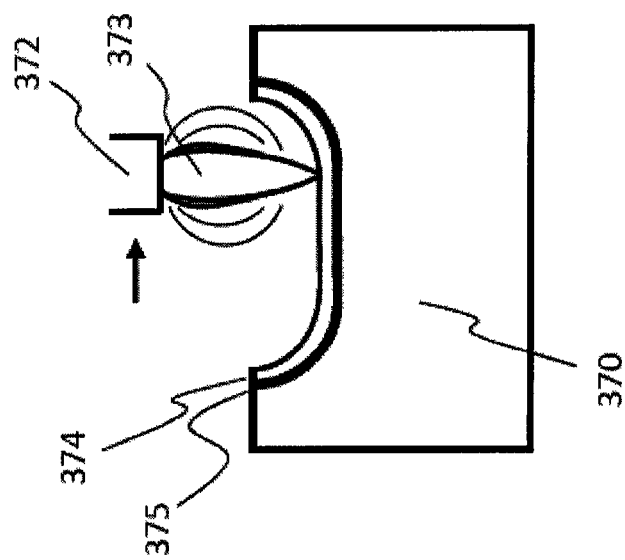
Figure 48D:
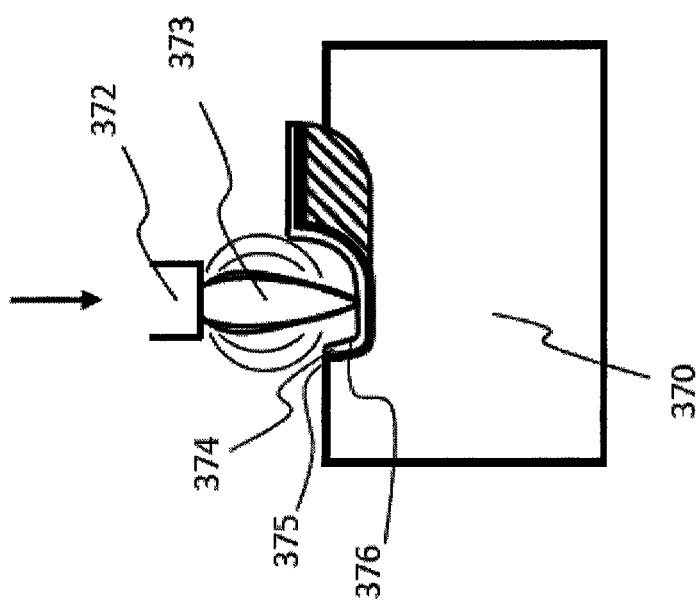

As shown in FIG. 48D, the operator again directs plasma-generating device 372 at tumor 371. To maintain the same rate of vaporization, the plasma-generating device is moved forward slightly, staying within 2-5 mm from the surface being vaporized. As a result, more undesired tumor tissue is vaporized. FIG. 48D shows that the plasma has vaporized past the bottom of tumor 371 and begun vaporizing healthy tissue 370. Because of the precise control the operator has over the depth of destruction, the operator will be able to consistently cease vaporization soon after reaching healthy tissue 370. Additionally, tissue underneath tumor 371 coagulated by the radially oscillating plasma flow, so bleeding does not occur. Vaporizing tissue below the surface of tissue 370 has formed a depression in the tissue which has walls 376. Because of the significant radial component of the dynamic pressure provided by a radially oscillating plasma flow, walls 376 will also be efficiently coagulated.

To finish the procedure, the plasma-generating device is again directed at other parts of tumor 371. This movement is shown in FIG. 48E, where plasma-generating device 372 has been moved substantially parallel to the surface of tissue 370. Continued application of radially oscillating plasma flow 373 has completely destroyed tumor 371. All that remains is healthy tissue 370, along with a sealing layer that completely stops even very intense bleeding. As explained above with reference to coagulation and cutting, the sealing layer has a morphology unique to volumetrically oscillating plasma flows which makes them preferred for stopping high levels of bleeding. Spongy layer 374, formed primarily by high velocity, low density plasma during the high intensity interval, has many sublayers corresponding to each high intensity interval. Also, compact layer 375 is relatively thick compared to spongy layer 375. This is possible because during the low intensity interval the low intensity plasma had the opportunity to heat the tissue in the compact layer without completely destroying the spongy layer formed during the high intensity interval.

The above discussion of vaporization applies to radially oscillating plasma flows with frequencies greater than 2,000 Hz. If the frequency is ultrasonic, the surgical task of vaporization is improved by the additional ultrasonic energy transferred to the tissue. In the preferred embodiment, the frequency of oscillations is 20,000-30,000 Hz. The benefits of ultrasonic energy for vaporization are very similar to the benefits observed in the surgical task of cutting. Specifically, cavitation at the surface of the tissue causes fragmentation, aiding in the destruction of the tumor. Cavitation within the tissue also improves the structure of the sealing layers. For example, the pore diameters of the spongy layer are reduced. Additionally, the compact layer has a sublayer composed of homogenized tissue where cavitation has destroyed the individual cell structure. This homogenized sublayer is particularly effective for coagulation. The end result is that the thickness of the sealing layer can be relatively thin without sacrificing the ability to stop very intense bleeding. This is particularly important for the surgical task of vaporization, where tissue must be destroyed while minimizing collateral damage.

In addition to coagulating tissue, a radially oscillating plasma flow used for vaporization can also simultaneously seal blood vessels exposed by the vaporization process. FIG. 49A-B show blood vessel 38 being sealed during vaporization. FIG. 49A shows tissue 370 near the end of the vaporization procedure. Blood vessel 378, which provided blood to the recently vaporized tissue, is now exposed. Unless blood vessel 378 is sealed, blood 379 will continue to flow out of the vessel. When such an exposed vessel is observed, the operator can use the same radially oscillating plasma flow used for vaporization to seal the exposed vessel. To do so, the operator directs radially oscillating plasma flow 373 at vessel 378. Due to the high dynamic pressure and heat flux, plasma flow 373 is able to evaporate blood 379 and penetrate deep into blood vessel 378. Because of this, blood vessel walls 377 will be heated to a depth of 1-1.5 vessel diameters. As walls 377 are heated they swell until they completely occlude blood vessel 378, forming a seal to stop blood flow. This is shown in FIG. 49B. While vessel 378 is shown at the bottom of the depression formed by the vaporization procedure, it is possible that the blood vessel could be exposed along wall 376 of the depression. Even though vessel 378 is not aligned with the plasma flow axis in this case, the radially oscillating plasma flow can still accomplish vessel sealing. This is due to a significant radial component of the dynamic pressure of plasma flow 373.

While the above discussion of FIG. 49A-B describes the vessel sealing process separately from vaporization, it should be noted that the process of vessel sealing is occurring simultaneously with the vaporization process. The operator does not significantly alter the vaporization procedure described in reference to FIGS. 48A-E. At most, the operator may need to spend slightly more time directing plasma flow 373 at a particular part of tumor 371 to seal a vessel, before proceeding to finish the vaporization procedure for the entire tumor.

In addition, in the preferred embodiment, with a frequency of oscillations in the range of 20,000-30,000 Hz, the cavitational effect due to the ultrasonic acoustic waves helps to seal the blood vessels. Experiments show that the thickness of blood vessel walls increase by a factor of 5, compared to the swelling accomplished without ultrasonic wave, facilitating rapid sealing of the vessel.

5.5 Non-Surgical Applications

Volumetrically oscillating plasma flows are also useful for a variety of non-surgical applications. These include medical applications outside of surgery as well as non-medical applications.

5.5.1 Wound Treatment, Cosmetics, and Pain Management

Volumetrically oscillating plasma flows can be used for non-surgical medical applications. For example, these plasma flows may be used in procedures for wound treatment, pain management, and plastic surgery. In these procedures, a volumetrically oscillating plasma flow is directed at a tissue. The goal of the procedure is to accomplish beneficial effects by generating and delivering certain chemicals deep into the tissue in the presence of heat and light. These chemicals, like NO or ozone, may be formed as reactants are introduced into the plasma flow. These reactants may be air, other gases, or conceivably other materials. Once introduced into the plasma flow, these reactants are heated and take part in chemical reactions which form the desired chemicals. These chemicals are then directed at the tissue surface. In these applications, the total heat provided to the tissue is preferably low. Therefore, in a preferred embodiment, the volumetrically oscillating plasma flow directed at the tissue is a volumetrically oscillating intermittent plasma flow.

A key benefit of using plasma flows to accomplish drug delivery in these applications is the high level of penetration of drugs into the tissue. Drug delivery has been shown to be significantly better when plasma flows were used compared to methods which deliver the drugs 'cold' to the surface of the tissue. By using a volumetrically oscillating plasma flow rather than a continuous plasma flow, this drug delivery is even more efficient. The benefit from volumetrically oscillating plasma flows is due to the bursts of high intensity plasma which reach higher temperatures than a continuous plasma can without damaging device components. These increased temperatures decrease the density and increase the dynamic pressure, which results in improved plasma and drug penetration.

Ultrasound has been shown to have a synergistic effect with some drugs, called chemopotentiation. Ultrasound effects cell membranes and temporarily increases their permeability. When combined with therapeutic drugs, more drug molecules diffuse into cells and produce an enhanced therapeutic effect. This synergetic effect makes treatment with these drugs more effective. In a preferred embodiment, the volumetrically oscillating plasma flow oscillates with an ultrasonic frequency, i.e. the frequency of oscillations is greater than 20,000 Hz

5.5.2 Plasma Waste Disposal

Volumetrically oscillating plasma flows can be used to efficiently destroy waste. The use of continuous plasma for waste disposal is well known, and the process is called plasma arc gasification. In gasification, one or more plasma flows are directed at waste inside a large furnace equipped to capture gaseous and solid byproducts. The plasma flows with a high temperature cause molecular dissociation in the waste and turn it into simple chemical components. This process safely destroys municipal, hazardous, and medical wastes rather than storing them in landfills. The resulting byproducts of the gasification process include valuable reclaimed metals and silicates, fuel and fuel intermediates such as syngas, and chemicals useful for industrial applications.

Volumetrically oscillating plasma flows and particularly the flows oscillating at ultrasonic frequencies can be used to improve the efficiency of plasma waste disposal. If oscillating at an ultrasonic frequency, the plasma flows supply ultrasonic energy to the waste in addition to the high temperatures of a typical plasma flow. This ultrasonic energy agitates the waste and fragments it into small pieces. This agitation preferably speeds up the chemical reactions which destroy the waste.

One current problem with plasma arc gasification systems is the rapid breakdown of components of the plasma waste disposal system exposed to the high temperatures of the plasma. For example, liners of the plasma furnaces in typical systems may have a service lifetime of one year or less. The short lifetimes of components increase maintenance costs of such systems. By using a volumetrically oscillating plasma flow, however, the average temperature can be kept relatively low while providing bursts of high intensity plasma at very high temperatures. This lower average temperature preferably reduces the strain on system components and increases their service lifetimes.

FIG. 50 shows an exemplary embodiment of a volumetrically oscillating plasma waste disposal system. Waste 401 enters furnace 402 through waste inlet 403. Plasma-generating devices 404 provide volumetrically oscillating plasma flows 405 which during operation destroy waste 401. Slag 406 comprised of molten solid byproduct accumulates at the bottom of furnace 402 and is collected for further processing. Gas byproducts are captured by vent system 407.

In some embodiments plasma-generating devices 404 may have dimensions much larger than the preferred dimensions for embodiments adopted for medical applications. For large scale waste processing, current levels, plasma-generating gas flow rates, and diameters of various portions of the heating channel may all be many times larger than the corresponding dimension of surgical embodiments described above.

5.5.3 Plasma Cleaning

Volumetrically oscillating plasma flows can also be used in improved systems and methods for plasma cleaning. In preferred embodiments, components of a plasma interact with a surface in several ways to remove contaminants and create an ultra-clean surface. First, the neutral plasma-generating gas atoms are directed with a high velocity at the surface being treated, removing and vaporizing contaminants. Second, other gases introduced into the plasma flow, such as oxygen, become energized and react with contaminants to form new compounds which are easily be removed from the surface. Third, photons generated by the plasma flow break down molecular bonds in the contaminants, facilitating their removal. For example, high molecular weight organic contaminants can be removed from a semiconductor substrate to create an ultra-clean surface appropriate for electronics fabrication.

Volumetrically oscillating plasma flows oscillating at an ultrasonic frequencies provide additional ultrasonic energy which preferably improves the cleaning process. Similar to the action of a sonicator, the addition of ultrasonic energy agitates the surface being treated and improves the efficiency of reactants in removing tightly adhering or embedded particles.

6 EQUIVALENTS

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed:

1. A system comprising:
   a. a power supply for generating a current wave having a low current level and pulses reaching a high current level according to a controlled pattern; and
   b. a plasma-generating device configured to:
      i. heat a plasma-generating gas to a first temperature with the current wave at the low current level, wherein the first temperature is at least 10,000 K,
      ii. heat the plasma-generating gas to a second temperature with the current wave at the high current level, wherein the second temperature is at least 10,000 K above the first temperature; and
      iii. discharge from an outlet the plasma-generating gas as a plasma flow that alternates between a high intensity plasma flow and a low intensity plasma flow according to the controlled pattern.

2. The system of claim 1, wherein the plasma-generating device comprises an anode forming a portion of a plasma channel, the plasma channel having the outlet with a diameter of 0.3-0.8 mm.

3. The system of claim 1, wherein the high current level is less than 50 A.

4. The system of claim 1, wherein the plasma-generating device is further configured to receive the plasma-generating gas at a flow rate of 0.1-0.6 L/min and at room temperature.

5. The system of claim 4, further comprising a control circuitry for monitoring the flow rate of the plasma-generating gas.

6. The system of claim 1, wherein the outlet is a first outlet, and the plasma-generating device comprises a cooling channel with a second outlet near the first outlet and for discharging a coolant.

7. The system of claim 1, wherein the plasma-generating device comprises a cathode assembly comprising multiple cathodes.

8. The system of claim 1, further comprising a control circuitry for causing the power supply to generate the current wave.

9. The system of claim 1, wherein:
   the current wave is a biased pulse wave with a pulse frequency of 20-100 Hz and a duty cycle of 0.05-0.15, and
   the low current level is in a range of 3-10 A and the high current level is in a range of 25-30 A.

10. The system of claim 1, wherein:
    the current wave is a biased pulse wave with a pulse frequency of above 2,000 Hz and a duty cycle of 0.05-0.15, and
    the low current level is in a range of 3-10 A and the high current level is in a range of 25-30 A.

11. The system of claim 1, wherein:
    the current wave is a modulated biased pulse wave produced by modulating a first biased pulse wave with a pulse frequency of above 20,000 Hz and a duty cycle of 0.35-0.65 with a second biased pulse wave with a pulse frequency of 20-100 Hz and a duty cycle of 0.05-0.15, and
    the low current level is in a range of 3-10 A and the high current level is in a range of 25-30 A.

12. The system of claim 1, wherein the current wave is a modulated biased pulse wave, in which a high frequency biased pulse wave is modulated by a low frequency biased pulse wave.

13. The system of claim 1, further comprising a processor and a user interface for programming a mode of operation of the system.

14. The system of claim 1, further comprising:
    a console including the power supply; and
    a connector to the plasma-generating device for providing to the plasma-generating device energy in the form of an electric current.

15. The system of claim 14, wherein the connector further supplies to the plasma-generating device the plasma-generating gas.

16. The system of claim 1, wherein the plasma flow has an active zone defined by plasma having a temperature above a threshold, the active zone expanding and contracting volumetrically upon discharge from the plasma-generating device according to a controlled pattern.

17. The system of claim 1, wherein the plasma-generating device is a hand-held surgical device.

18. The system of claim 1, wherein the plasma-generating device comprises an anode, a cathode, and a heating portion, and the plasma flow is formed with an electric current arc established between the anode and the cathode.

19. The system of claim 18, wherein a temperature of the plasma flow is proportional to a ratio of a current of the electric current arc to a diameter of the heating portion.

20. The system of claim 18, wherein the pulses have a ramp rate of at least 25 A per 10 µs.

* * * * *